US011701384B2

(12) United States Patent
Chen et al.

(10) Patent No.: US 11,701,384 B2
(45) Date of Patent: Jul. 18, 2023

(54) METHODS AND COMPOSITIONS INVOLVING INTERLEUKIN-6 RECEPTOR ALPHA-BINDING SINGLE CHAIN VARIABLE FRAGMENTS

(71) Applicant: THE REGENTS OF THE UNIVERSITY OF CALIFORNIA, Oakland, CA (US)

(72) Inventors: Yvonne Yu-Hsuan Chen, Los Angeles, CA (US); Meng-Yin Lin, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 573 days.

(21) Appl. No.: 16/329,367

(22) PCT Filed: Sep. 1, 2017

(86) PCT No.: PCT/IB2017/055281
§ 371 (c)(1),
(2) Date: Feb. 28, 2019

(87) PCT Pub. No.: WO2018/042385
PCT Pub. Date: Mar. 8, 2018

(65) Prior Publication Data
US 2020/0179448 A1  Jun. 11, 2020

Related U.S. Application Data

(60) Provisional application No. 62/443,509, filed on Jan. 6, 2017, provisional application No. 62/440,991, filed on Dec. 30, 2016, provisional application No. 62/383,237, filed on Sep. 2, 2016.

(51) Int. Cl.
A61K 35/17 (2015.01)
C07K 14/715 (2006.01)

(52) U.S. Cl.
CPC .......... A61K 35/17 (2013.01); C07K 14/7155 (2013.01); C07K 2317/24 (2013.01); C07K 2317/565 (2013.01); C07K 2317/622 (2013.01); C07K 2317/73 (2013.01); C07K 2317/76 (2013.01); C07K 2319/03 (2013.01)

(58) Field of Classification Search
None
See application file for complete search history.

(56) References Cited

U.S. PATENT DOCUMENTS

| 4,797,368 | A | 1/1989 | Carter et al. |
|---|---|---|---|
| 5,138,941 | A | 8/1992 | Strauss |
| 5,139,941 | A | 8/1992 | Muzyczka |
| 5,670,373 | A | 9/1997 | Kishimoto |
| 5,821,337 | A | 10/1998 | Carter et al. |
| 6,319,494 | B1 | 11/2001 | Capon et al. |
| 7,151,169 | B2 | 12/2006 | Thompson et al. |
| 7,276,477 | B2 | 10/2007 | Osslund et al. |
| 7,479,543 | B2* | 1/2009 | Tsuchiya ............ A61P 35/00 530/387.1 |
| 7,741,465 | B1 | 6/2010 | Eshhar et al. |
| 8,012,482 | B2 | 9/2011 | Adams et al. |
| 8,063,182 | B1 | 11/2011 | Brockhaus et al. |
| 8,236,541 | B2 | 8/2012 | Black |
| 8,399,645 | B2 | 3/2013 | Campana et al. |
| 8,580,264 | B2 | 11/2013 | Zhang et al. |
| 9,447,194 | B2 | 9/2016 | Jensen |
| 9,464,140 | B2 | 10/2016 | June et al. |
| 9,518,123 | B2 | 12/2016 | June et al. |
| 9,540,445 | B2 | 1/2017 | June et al. |
| 9,834,590 | B2 | 12/2017 | Campana et al. |
| 11,066,680 | B2* | 7/2021 | Yu ..................... C07K 14/7051 |
| 2004/0026871 | A1 | 2/2004 | Stephens et al. |
| 2004/0254774 | A1 | 12/2004 | Loh et al. |
| 2006/0135517 | A1 | 6/2006 | Lee et al. |
| 2006/0251658 | A1 | 11/2006 | Ledbetter et al. |
| 2007/0142376 | A1 | 6/2007 | Fleenor et al. |
| 2009/0068158 | A1 | 3/2009 | Medin et al. |
| 2010/0330676 | A1 | 12/2010 | Horowitz et al. |
| 2011/0008364 | A1 | 1/2011 | Ledbetter et al. |
| 2011/0286980 | A1 | 11/2011 | Brenner et al. |
| 2013/0071414 | A1 | 3/2013 | Dotti et al. |
| 2013/0280220 | A1 | 10/2013 | Ahmed et al. |
| 2014/0141000 | A1 | 5/2014 | Chiu et al. |
| 2014/0314760 | A1 | 10/2014 | Rosenblum et al. |

(Continued)

FOREIGN PATENT DOCUMENTS

| CN | 105837693 A | 8/2016 |
|---|---|---|
| CN | 107074957 A | 8/2016 |

(Continued)

OTHER PUBLICATIONS

Extended Search Report Issued in Corresponding European Patent Application No. EP 17845645.5, dated Mar. 24, 2020.
Patel, et al., "Cancer CARtography: Charting Out A New Approach to Cancer Immunotherapy," *Immunotherapy*, 6(6): 675-678, 2014.
Suarez, et al., "Chimeric Antigen Receptor T Cells Secreting Anti-PD-L1 Antibodies More Effectively Regress Renal Cell Carcinoma in a Humanized Mouse Model," *Oncotarget*, 7(23): 34341-34355, 2016.
Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression" *Cancer Res.*, 2011, 71(17):5697-5706.
International Search Report and Written Opinion issued in International Patent Application No. PCT/IB2017/055281, dated Mar. 8, 2018.

(Continued)

*Primary Examiner* — Patricia Duffy
(74) *Attorney, Agent, or Firm* — Norton Rose Fulbright US LLP

(57) ABSTRACT

Disclosed are compositions comprising an isolated chimeric interleukin 6 receptor alpha (IL-6Rα) binding protein or cells expressing an isolated chimeric IL-6Rα binding protein. The isolated IL-6Rα chimeric binding protein and cells expressing the protein may be used in methods of treating cancer and reducing the risk of cytokine release syndrome.

19 Claims, 8 Drawing Sheets
Specification includes a Sequence Listing.

(56) References Cited

U.S. PATENT DOCUMENTS

| | | | |
|---|---|---|---|
| 2015/0038684 | A1 | 2/2015 | Jensen |
| 2017/0333480 | A1 | 11/2017 | Cooper et al. |
| 2018/0022815 | A1 | 1/2018 | Chang |

FOREIGN PATENT DOCUMENTS

| | | |
|---|---|---|
| CN | 106414502 A | 2/2017 |
| EP | WO 2004/019990 | 3/2004 |
| EP | 1810980 | 7/2007 |
| EP | 2330193 | 6/2011 |
| EP | WO 2014/072233 | 5/2014 |
| EP | 3550020 | 10/2019 |
| WO | WO 1992/019759 | 11/1992 |
| WO | WO 1994/012520 | 6/1994 |
| WO | WO 98/50432 | 11/1998 |
| WO | WO 2017/075433 | 5/2001 |
| WO | WO 2006/046661 | 5/2006 |
| WO | WO 2011/140170 | 11/2011 |
| WO | WO 2013/123061 | 8/2013 |
| WO | WO 2014/164709 | 10/2014 |
| WO | WO 2015/121454 | 8/2015 |
| WO | WO 2016/094304 | 6/2016 |
| WO | WO 2017/096329 | 6/2017 |
| WO | WO 2017/172981 | 10/2017 |
| WO | 2017/222593 | 12/2017 |
| WO | 2018/102795 | 6/2018 |
| WO | WO 2018/103502 | 6/2018 |
| WO | 2018/237022 | 12/2018 |

OTHER PUBLICATIONS

Maude et al., "Managing Cytokine Release Syndrome Associated with Novel T Cell-Engaging Therapies" Cancer J., 2014, 20(2):119-122.

Ahmad et al., "ScFv Antibody: Principles and Clinical Application," Clin Dev Immunol, 2012:980250, (2012).

Ali, et al., "T Cells Expressing an Anti-B-Cell Maturation Antigen Chimeric Antigen Receptor Cause Remissions of Multiple Myeloma," Blood, 128:1688-1700, 2016.

Bendle et al., "Blockade of TGF-β signaling greatly enhances the efficacy of TCR gene therapy of cancer." J. Immunol, 191(6):3232-3239, (2013).

Berdeja, et al., "First-In-Human Multicenter Study of bb2121 Anti-BCMA CAR T-Cell Therapy for Relapsed/Refractory Multiple Myeloma: Updated Results.," Journal of Clinical Oncology, 35(15 suppl):3010-3010, 2017.

Birchenough, et al., "Equity Research: Deep Dive on Emerging Cell Therapies for Cancer," Research Report Online Wells Fargo Securities, LLC Apr. 19, 2017, retrieved on Nov. 22, 2019 from the internet https://cdn2.hubspot.net/hubfs/4625168/%5B2017%5D%20Wells%20Fargo%20-%20Deep%20Dive%20Dive%20on%20Emerging%20Cell%20Therapies.pdf 1-94, p. 37, 5th paragraph.

Blat et al., "Suppression of murine colitis and its associated cancer by carcinoembryonic antigen-specific regulatory T cells," Mol Ther, 22:1018-1028, (2014).

Boissel et al., "Retargeting NK-92 cells bty means of CD19-and CD20-specific chemieric antigen receptors compares favorably with antibody-dependent cellular cytotoxicity," OncoImmunology, 2(10):e26527, (2013).

Bollard et al., "Adapting a transforming growth factor β-related tumor protection strategy to enhance antitumor immunity." Blood, 99(9):3179-3187,(2002).

Bond, J.S. et al., "Intracellular Proteases," Annual Review of Biochemistry, 56:333-364, 1987.

Brentjens et al., "CD19-targeted T cells rapidly induce molecular remissions in adults with chemotherapy-refractory acute lymphoblastic leukemia", Sci. Transl. Med., 5:177ra138, (2013).

Brudno et al., "Toxicities of chimeric antigen receptor T cells: recognition and management," Blood, 127:3321-3330, (2016).

Brunstein et al., "Umbilical cord blood-derived T regulatory cells to prevent GVHD: kinetics, toxicity profile, and clinical effect," Blood, 127:1044-1051, (2016).

Brusko et al., "Human antigen-specific regulatory T cells generated by T cell receptor gene transfer", PLoS One, 5:e11726, (2010).

Budde et al., "Combining a CD20 chimeric antigen receptor and an inducible caspase 9 suicide switch to improve the efficacy and safety of T cell adoptive immunotherapy for lymphoma," PloS One, 8(12): e82742, 2013.

Carpenter, et al. B-cell Maturation Antigen Is a Promising Target for Adoptive Tcell Therapy of Multiple Myeloma, Clinical Cancer Research, 19(8): 2048-2060, 2013.

Chen et al, "Fusion protein linkers: Property, design and functionality", Advanced Drug Delivery Reviews, vol. 65, (2003), pp. 1357-1369.

Chen, et al., "A Unique Substrate Recognition Profile for Matrix Metalloproteinase-2," The Journal of Biological Chemistry, 277(6): 4485-4491, 2002.

Chen, et al., "A Compound Chimeric Antigen Receptor Strategy For Targeting Multiple Myyeloma," Leukemia, 32(2):402-412, 2018.

Chu, "Genetic Modification of T Cells Redirected toward CS1 Enhances Eradication of Myeloma Cells," Clinical Cancer Research, 20(15):3989-4000, 2014.

Chu, et al., "CS1-Specific Chimeric Antigen Receptor (CAR)-Engineered Natural Killer Cells Enhance In Vitro and In Vivo Antitumor Activity Against Human Multiple Myeloma," Leukemia, 28: 917-927, 2014.

Cohen, et al., "B-Cell Maturation Antigen (BCMA) Specific Chimeric Antigen Receptor T Cells (CART-BCMA) for Multiple Myeloma (MM): Initial Safety and Efficacy From a Phase I Study," Blood, 128:1147, 2016.

Dalken, et al., "Targeted Induction of Apoptosis by Chimeric Granzyme B Fusion Proteins Carrying Antibody and Growth Factor Domains for Cell Recognition," Cell Death Differentiation, 13, pp. 576-585. (2006).

Davila et al., "Efficacy and toxicity management of 19-28z Car T cell therapy in B cell acute lymphoblastic leukemia.", Sci. Transl. Med., 6:224ra225, (2014).

Dotti et al., "Design and development of therapies using chimeric antigen receptor-expressing T-cells", Immunological Reviews, 257:107-126, (2014).

Duebner, et al., "Reprogramming Control of an Allosteric Signaling Switch Through Modular Recombination," Science, 301(5641), pp. 1904-1908. (2003).

Duffy, M.J., "Proteases as Prognostic Markers in Cancer," Clinical Cancer Research, 2:613-618, 1996.

Dull et al., "A Third-Generataion Lentivirus Vector with a Conditional Packaging System," J. Virol, 72(11):8463-8471, (1998).

Ellebrecht et al., "Reengineering chimeric antigen receptor T cells for targeted therapy of autoimmune disease," Science, 353:179-184, (2016).

Extended European Search Report Issued in Corresponding European Application 15870819.8, dated Apr. 13, 2018.

Foster et al., "Antitumor activity of EBC-specific T lymphocytes transduced with a dominant negative TGF-β receptor," J. Immunother., 31(5):500-505,(2008).

Gogishvili, et al., "SLAMF7-CAR T Cells Eliminate Myeloma and Confer Selective Fratricide of SLAMF7+ Normal Lymphocytes," Blood, 130: 2838-2847, 2017.

Gorelik and Flavell, "Immune-mediated eradication of tumors through the blockade of transforming growth factor-β signaling in T cells" Nat. Med., 7:1118-1122 (2001).

Hay, "SUMO-Specific Proteases: A Twist in the Tail," Trends in Cell Biology, 17(8): 370-376, 2007.

Hillerdal et al., "Chimeric antigen receptor-engineered T cells for the treatment of metastatic prostate cancer," BioDrugs, 29:75-89, (2015).

Ho, et al., "Covert Cancer Therapeutics: Engineering T Cells to Interrogate Intracellular Tumor Antigens," 2015 AIChE Annual Meeting, Nov. 12, 2015, Salt Lake City, UT.

Ho, et al., "Modularly Constructed Synthetic Granzyme B Molecule Enables Interrogation of Intracellular Proteases for Targeted Cytotoxicity," ACS Synthetic Biology, 6, pp. 1484-1495. (2017).

(56) References Cited

OTHER PUBLICATIONS

International Preliminary Report on Patentability Issued in Corresponding PCT Patent Application No. PCT/US2019/036731, dated Dec. 15, 2020.
International Search Report and Written Opinion Issued in Corresponding PCT Application No. PCT/US2015/065623, dated Apr. 19, 2016.
International Search Report and Written Opinion Issued in Corresponding PCT Patent Application No. PCT/US2019/036731, dated Dec. 27, 2019.
International Search Report and Written Opinion Issued in International Application No. PCT/US2015/065620, dated Mar. 28, 2016.
International Search Report and Written Opinion issued in International Application No. PCT/US2016/059444, dated Feb. 14, 2017.
Kalos et al., "T cells with chimeric antigen receptors have potent antitumor effects and can establish memory in patients with advanced leukemia," *Sci. Transl. Med.*, 3(95):95ra73, (2011).
Kelchtermans et al., "Activated CD4+CD25+ regulatory T cells inhibit osteoclastogenesis and collagen-induced arthritis", *Ann. Rheum. Dis.*, 68:744-750, (2009).
Kelchtermans et al., "Defective CD4+CD25+ regulatory T cell functioning in collagen-induced arthritis: an important factor in pathogenesis, counter-regulated by endogenous IFN-gamma", *Arthritis Res. Ther.*, 7:R402-415, (2005).
Kessenbrock, et al., "Matrix Metalloproteinases: Regulators of the Tumor Microenvironment," *Cell*, 141(1): 52-67, 2010.
Kochenderfer et al., "B-cell depletion and remissions of malignancy along with cytokine-associated toxicity in a clinical trial of anti-CD19 chimeric-antigen-receptor-transduced T cells", *Blood*, 119:2709-2720, (2012).
Le Gall et al., "Effect of linker sequences between the antibody variable domains on the formation, stability and biological activity of a bispecific tandem diabody" *Protein Engineering, Design & Selection* 2004, 17(4), 357-366.
Le Gall et al., "Immunosuppressive properties of anti-CD3 single-chain Fv and diabody" *Journal of Immunological Methods* 2004, 285, 111-127.
Lee et al., "Current concepts in the diagnosis and management of cytokine release syndrome," *Blood*, 124:188-195, (2014).
Lee, et al., "An APRIL-Based Chimeric Antigen Receptor for Dual Targeting of BCMA and TACI in Multiple Myeloma," *Blood*, 131:746-758, 2018.
Lopez-Otin & Matrisian, "Emerging Roles of Proteases in Tumour Suppression," *Nature*, 7: 800-808, 2007.
Malakhov, et al., SUMO Fusions and SUMO-Specific Protease for Efficient Expression and Purification of Proteins, *Journal of Structural and Functional Genomics*, 5(1-2). (2004).
Morgan et al., "Effective treatment of collagen-induced arthritis by adoptive transfer of CD25+ regulatory T cells," *Arthritis Rheum*, 52:2212-2221, (2005).
Myasoedova et al., "Is the incidence of rheumatoid arthritis rising?: results from Olmsted County, Minnesota, 1955-2007", *Arthritis Rheum*, 62-1576-1582, (2010).
Nakamura et al., "TGF-beta 1 plays an important role in the mechanism of CD4+CD25+ regulatory T cell activity in both humans and mice," *J Immunol*, 164:183-190, (2004).
Pastan, et al., "Immunotoxin Treatment of Cancer," Annual Review of Medicine, 58, pp. 221-237. (2007).
Porter et al., "Chimeric antigen receptor-modified T cells in chronic lymphoid leukemia," *N. Engl. J. Med.*, 365:725-733, (2011).
Qin et al, "Preclinical Development of Bivalent Chimeric Antigen Receptors Targeting Both CD19 and CD22", *Molecular Therapy: Oncolytics*, vol. 11, Dec. 21, 2018, pp. 127-137.
Qin et al, "Supplemental Information. Preclinical Development of Bivalent Chimeric Antigen Receptors Targeting Both CD19 and CD22", *Molecular Therapy: Oncolytics*, vol. 11.

Quatromoni et al., "T cell receptor (TCR)-transgenic CD8 lymphocytes rendered insensitive to transforming growth factor beta (TGFβ) signaling mediate superior tumor regression in an animal model of adoptive cell therapy" *J. Transl. Med.*, 10:127, (2012).
Rosenberg, "Finding suitable targets is the major obstacle to cancer gene therapy", *Cancer Gene Ther.*, 21:45-47, (2017).
Rosenzweig, et al., "Preclinical Data Support Leveraging CS1 Chimeric Antigen Receptor T-Cell Therapy For Systemic Light Chain Amyloidosis," *Cytotherapy*, 19(7):861-866, 2017.
Stahnke, et al., "Granzyme B-H22 (scFv), a Human Immunotoxin Targeting CD64 in Acute Myeloid Leukemia in Monocytic Subtypes," *Molecular Cancer Therapeutics*, 7(9), pp. 2924-2932. (2008).
Stone et al., "A sensitivity scale for targeting T cells with chimeric antigen receptors (CARs) and bispecific T-cell engagers (BiTEs)" *Oncoimmunology*, 1(6):863-873, (2012).
Supplementary European Search Report issued in European Patent Application No. 15870818, dated Apr. 10, 2018.
Szymczak-Workman et al., "Design and construction of 2A peptide-linked multicistronic vectors," *Cold Spring Harb Protoc*, 2012(2):199-204, (2012).
Tang et al., "Regulatory T-cell therapy in transplantation: moving to the clinic", *Cold Spring Harb Perspect Med.*, 3:a015552, (2013).
Thornberry, et al., "A Combinatorial Approach Defines Specificities of Members of the Caspase Family and Granzyme B," *The Journal of Biological Chemistry*, 272(29): 17907-17911, 1997.
Thornton et al., "Suppressor effector function of CD4+CD25+ immunoregulatory T cells is antigen nonspecific", *J Immunol*, 164:183-190, (2000).
Wang, et al., "Lenalidomide Enhances the Function of CS1 Chimeric Antigen Receptor-Redirected T Cells Against Multiple Myeloma," *Clinical Cancer Research*, 24(1):106-119, 2018.
Widdifield et al., "The epidemiology of rheumatoid arthritis in Ontario, Canada." *Arthritis Rheumatol*, 66:786-793 (2014).
Wright et al., "Adoptive therapy with redirected primary regulatory T cells results in antigen-specific suppression of arthritis," *Proc. Natl. Acad. Sci. USA*, 106(45):19078-19083, (2009).
Wright et al., "Regulatory T-cell adoptive immunotherapy: potential for treatment of autoimmunity", *Expert Rev. Clin. Immunol.*, 7:213-225, (2011).
Wu et al., "FOXP3 controls regulatory T cell function through cooperation with NFAT", *Cell*, 126:375-387, (2006).
Wyatt, et al., "Human Telomerase Reverse Transcriptase (hTERT) Q169 Is Essential for Telomerase Function In Vitro and In Vivo," *PLoS One*, 4(9), pp. 1-14. (2009).
Yingling et al., "Development of TGF-β signalling inhibitors for cancer therapy" *Nat. Rev. Drug Discov.*, 3:1011-1022 (2004).
Zhang et al., "Adoptive Transfer of Tumor-Reactive Transforming Growth Factor-β-Insensitive CD8+ T Cells" *Cancer Res.* 65(5):1761-1769. (2005).
Zhang et al., "Inhibition of TGF-β signaling in genetically engineered tumor antigen-reactive T cells significantly enhances tumor treatment efficacy," *Gene Ther.*, 20:575-580, (2012).
Zhao, et al., "Secreted Antibody/Granzyme B Fusion Protein Stimulates Selective Killing of HER2-Overexpressing Tumor Cells," *The Journal of Biological Chemistry*, 279(20), pp. 21343-21348. (2004).
Extended European Search Report and Search Opinion dated Jan. 25, 2022 and issued in European Patent Application No. 19819799.8.
Zah, Eugenia et al., "Systematically optimized BCMA/CS1 bispecific CAR-T cells robustly control heterogeneous multiple myeloma," *Nature Communications*, vol. 11, No. 1, whole document, May 8, 2020.
Office Action and Search Report dated Oct. 12, 2022 in Chinese Application No. 201980053239.6.
Ramadoss, NS et al., An anti-B cell maturation antigen bispecific antibody for multiple myeloma. *J Am Chem Soc*; pp. 5288-5291; Apr. 15, 2015 (Abstract).

* cited by examiner

SEQUENCE LISTING

<160> NUMBER OF SEQ ID NOS: 89

<210> SEQ ID NO 1
<211> LENGTH: 715
<212> TYPE: PRT
<213> ORGANISM: Homo sapiens

<400> SEQUENCE: 1

Met Glu Thr Asp Thr Leu Leu Leu Trp Val Leu Leu Leu Trp Val Pro
1               5                   10                  15

Gly Ser Thr Gly Asp Gly Gly Ser Asp Tyr Lys Asp Asp Asp Lys
            20                  25                  30

Gly Gly Ser Asp Ile Gln Met Thr Gln Ser Pro Ser Ser Leu Ser Ala
        35                  40                  45

Ser Val Gly Asp Arg Val Thr Ile Thr Cys Arg Ala Ser Gln Asp Ile
    50                  55                  60

```
Ser Ser Tyr Leu Asn Trp Tyr Gln Gln Lys Pro Gly Lys Ala Pro Lys
 65                  70                  75                  80

Leu Leu Ile Tyr Tyr Thr Ser Arg Leu His Ser Gly Val Pro Ser Arg
                 85                  90                  95

Phe Ser Gly Ser Gly Ser Gly Thr Asp Phe Thr Phe Thr Ile Ser Ser
            100                 105                 110

Leu Gln Pro Glu Asp Ile Ala Thr Tyr Tyr Cys Gln Gln Gly Asn Thr
        115                 120                 125

Leu Pro Tyr Thr Phe Gly Gln Gly Thr Lys Val Glu Ile Lys Arg Thr
    130                 135                 140

Val Ala Ala Pro Ser Val Phe Ile Phe Pro Pro Ser Asp Glu Gln Leu
145                 150                 155                 160

Lys Ser Gly Thr Ala Ser Val Val Cys Leu Leu Asn Asn Phe Tyr Pro
                165                 170                 175

Arg Glu Ala Lys Val Gln Trp Lys Val Asp Asn Ala Leu Gln Ser Gly
            180                 185                 190

Asn Ser Gln Glu Ser Val Thr Glu Gln Asp Ser Lys Asp Ser Thr Tyr
        195                 200                 205

Ser Leu Ser Ser Thr Leu Thr Leu Ser Lys Ala Asp Tyr Glu Lys His
    210                 215                 220

Lys Val Tyr Ala Cys Glu Val Thr His Gln Gly Leu Ser Ser Pro Val
225                 230                 235                 240

Thr Lys Ser Phe Asn Arg Gly Glu Cys Gly Thr Ser Gly Ser Ser Gly
                245                 250                 255

Lys Pro Gly Ser Gly Glu Gly Ser Thr Lys Gly Glu Val Gln Leu Gln
            260                 265                 270

Glu Ser Gly Pro Gly Leu Val Arg Pro Ser Gln Thr Leu Ser Leu Thr
        275                 280                 285

Cys Thr Val Ser Gly Tyr Ser Ile Thr Ser Asp His Ala Trp Ser Trp
    290                 295                 300

Val Arg Gln Pro Pro Gly Arg Gly Leu Glu Trp Ile Gly Tyr Ile Ser
305                 310                 315                 320

Tyr Ser Gly Ile Thr Thr Tyr Asn Pro Ser Leu Lys Ser Arg Val Thr
                325                 330                 335

Met Leu Arg Asp Thr Ser Lys Asn Gln Phe Ser Leu Arg Leu Ser Ser
            340                 345                 350

Val Thr Ala Ala Asp Thr Ala Val Tyr Tyr Cys Ala Arg Ser Leu Ala
        355                 360                 365

Arg Thr Thr Ala Met Asp Tyr Trp Gly Gln Gly Ser Leu Val Thr Val
    370                 375                 380

Ser Ser Ala Ser Thr Lys Gly Pro Ser Val Phe Pro Leu Ala Pro Ser
385                 390                 395                 400

Ser Lys Ser Thr Ser Gly Gly Thr Ala Ala Leu Gly Cys Leu Val Lys
                405                 410                 415

Asp Tyr Phe Pro Glu Pro Val Thr Val Ser Trp Asn Ser Gly Ala Leu
            420                 425                 430

Thr Ser Gly Val His Thr Phe Pro Ala Val Leu Gln Ser Ser Gly Leu
        435                 440                 445

Tyr Ser Leu Ser Ser Val Val Thr Val Pro Ser Ser Ser Leu Gly Thr
    450                 455                 460

Gln Thr Tyr Ile Cys Asn Val Asn His Lys Pro Ser Asn Thr Lys Val
465                 470                 475                 480

Asp Lys Lys Val Glu Pro Lys Ser Cys Asp Lys Thr His Thr Cys Pro
```

```
            485                 490                 495
Pro Cys Pro Ala Pro Glu Leu Leu Gly Gly Pro Ser Val Phe Leu Phe
            500                 505                 510

Pro Pro Lys Pro Lys Asp Thr Leu Met Ile Ser Arg Thr Pro Glu Val
            515                 520                 525

Thr Cys Val Val Val Asp Val Ser His Glu Asp Pro Glu Val Lys Phe
            530                 535                 540

Asn Trp Tyr Val Asp Gly Val Glu Val His Asn Ala Lys Thr Lys Pro
545                 550                 555                 560

Arg Glu Glu Gln Tyr Asn Ser Thr Tyr Arg Val Val Ser Val Leu Thr
                565                 570                 575

Val Leu His Gln Asp Trp Leu Asn Gly Lys Glu Tyr Lys Cys Lys Val
            580                 585                 590

Ser Asn Lys Ala Leu Pro Ala Pro Ile Glu Lys Thr Ile Ser Lys Ala
            595                 600                 605

Lys Gly Gln Pro Arg Glu Pro Gln Val Tyr Thr Leu Pro Pro Ser Arg
            610                 615                 620

Asp Glu Leu Thr Lys Asn Gln Val Ser Leu Thr Cys Leu Val Lys Gly
625                 630                 635                 640

Phe Tyr Pro Ser Asp Ile Ala Val Glu Trp Glu Ser Asn Gly Gln Pro
                645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
            675                 680                 685

Gly Asn Val Phe Ser Cys Ser Val Met His Glu Ala Leu His Asn His
            690                 695                 700

Tyr Thr Gln Lys Ser Leu Ser Leu Ser Pro Gly
705                 710                 715

<210> SEQ ID NO 2
<211> LENGTH: 715
<212> TYPE: PRT
<213> ORGANISM: Homo sapiens

<400> SEQUENCE: 2

Met Glu Thr Asp Thr Leu Leu Leu Trp Val Leu Leu Leu Trp Val Pro
1               5                   10                  15

Gly Ser Thr Gly Asp Gly Gly Ser Asp Tyr Lys Asp Asp Asp Asp Lys
            20                  25                  30

Gly Gly Ser Glu Val Gln Leu Gln Glu Ser Gly Pro Gly Leu Val Arg
            35                  40                  45

Pro Ser Gln Thr Leu Ser Leu Thr Cys Thr Val Ser Gly Tyr Ser Ile
            50                  55                  60

Thr Ser Asp His Ala Trp Ser Trp Val Arg Gln Pro Pro Gly Arg Gly
65              70                  75                  80

Leu Glu Trp Ile Gly Tyr Ile Ser Tyr Ser Gly Ile Thr Thr Tyr Asn
                85                  90                  95

Pro Ser Leu Lys Ser Arg Val Thr Met Leu Arg Asp Thr Ser Lys Asn
            100                 105                 110

Gln Phe Ser Leu Arg Leu Ser Ser Val Thr Ala Ala Asp Thr Ala Val
            115                 120                 125

Tyr Tyr Cys Ala Arg Ser Leu Ala Arg Thr Thr Ala Met Asp Tyr Trp
            130                 135                 140
```

```
Gly Gln Gly Ser Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
450                 455                 460

Met His Glu Ala Leu His Asn His Tyr Thr Gln Lys Ser Leu Ser Leu
465                 470                 475                 480

Ser Pro Gly Gly Ser Thr Ser Gly Ser Gly Lys Pro Gly Ser Gly Glu
                485                 490                 495

Gly Ser Thr Lys Gly Asp Ile Gln Met Thr Gln Ser Pro Ser Ser Leu
            500                 505                 510

Ser Ala Ser Val Gly Asp Arg Val Thr Ile Thr Cys Arg Ala Ser Gln
        515                 520                 525

Asp Ile Ser Ser Tyr Leu Asn Trp Tyr Gln Gln Lys Pro Gly Lys Ala
            530                 535                 540

Pro Lys Leu Leu Ile Tyr Tyr Thr Ser Arg Leu His Ser Gly Val Pro
545                 550                 555                 560

Ser Arg Phe Ser Gly Ser Gly Ser Gly Thr Asp Phe Thr Phe Thr Ile
```

```
                565                 570                 575
Ser Ser Leu Gln Pro Glu Asp Ile Ala Thr Tyr Tyr Cys Gln Gln Gly
            580                 585                 590

Asn Thr Leu Pro Tyr Thr Phe Gly Gln Gly Thr Lys Val Glu Ile Lys
        595                 600                 605

Arg Thr Val Ala Ala Pro Ser Val Phe Ile Phe Pro Pro Ser Asp Glu
    610                 615                 620

Gln Leu Lys Ser Gly Thr Ala Ser Val Val Cys Leu Leu Asn Asn Phe
625                 630                 635                 640

Tyr Pro Arg Glu Ala Lys Val Gln Trp Lys Val Asp Asn Ala Leu Gln
            645                 650                 655

Ser Gly Asn Ser Gln Glu Ser Val Thr Glu Gln Asp Ser Lys Asp Ser
        660                 665                 670

Thr Tyr Ser Leu Ser Ser Thr Leu Thr Leu Ser Lys Ala Asp Tyr Glu
    675                 680                 685

Lys His Lys Val Tyr Ala Cys Glu Val Thr His Gln Gly Leu Ser Ser
690                 695                 700

Pro Val Thr Lys Ser Phe Asn Arg Gly Glu Cys
705                 710                 715

<210> SEQ ID NO 3
<211> LENGTH: 448
<212> TYPE: PRT
<213> ORGANISM: Homo sapiens

<400> SEQUENCE: 3

Glu Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 4
<211> LENGTH: 214
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 6
<212> TYPE: PRT
<213> ORGANISM: Homo sapiens

<400> SEQUENCE: 5

Ser Asp His Ala Trp Ser
1               5

<210> SEQ ID NO 6
<211> LENGTH: 16
<212> TYPE: PRT
<213> ORGANISM: Homo sapiens

<400> SEQUENCE: 6

Tyr Ile Ser Tyr Ser Gly Ile Thr Thr Tyr Asn Pro Ser Leu Lys Ser
1               5                   10                  15

<210> SEQ ID NO 7
<211> LENGTH: 10
<212> TYPE: PRT
<213> ORGANISM: Homo sapiens

<400> SEQUENCE: 7

Ser Leu Ala Arg Thr Thr Ala Met Asp Tyr
1               5                   10

<210> SEQ ID NO 8
<211> LENGTH: 11
<212> TYPE: PRT
<213> ORGANISM: Homo sapiens

<400> SEQUENCE: 8

Arg Ala Ser Gln Asp Ile Ser Ser Tyr Leu Asn
1               5                   10

<210> SEQ ID NO 9
<211> LENGTH: 7
<212> TYPE: PRT
<213> ORGANISM: Homo sapiens

<400> SEQUENCE: 9

Tyr Thr Ser Arg Leu His Ser
1               5

<210> SEQ ID NO 10
<211> LENGTH: 9
<212> TYPE: PRT
<213> ORGANISM: Homo sapiens

<400> SEQUENCE: 10

Gln Gln Gly Asn Thr Leu Pro Tyr Thr
1               5
```

<210> SEQ ID NO 11
<211> LENGTH: 18
<212> TYPE: PRT
<213> ORGANISM: Homo sapiens

<400> SEQUENCE: 11

Gly Ser Thr Ser Gly Ser Gly Lys Pro Gly Ser Gly Glu Gly Ser Thr
1               5                   10                  15

Lys Gly

<210> SEQ ID NO 12
<211> LENGTH: 246
<212> TYPE: PRT
<213> ORGANISM: Homo sapiens

<400> SEQUENCE: 12

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Gln Gln Ser Gly Ala Glu Leu Val Lys Pro Gly Ala Ser Val Lys Met
    130                 135                 140

Ser Cys Lys Ala Ser Gly Tyr Thr Phe Thr Ser Tyr Asn Met His Val
145                 150                 155                 160

Trp Lys Gln Thr Pro Gly Gln Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Thr Ala Tyr Met Gln Leu Ser
        195                 200                 205

Ser Leu Thr Ser Glu Asp Ser Ala Asp Tyr Tyr Cys Ala Arg Ser Asn
    210                 215                 220

Tyr Tyr Gly Ser Ser Tyr Trp Phe Phe Asp Val Trp Gly Ala Gly Thr
225                 230                 235                 240

Thr Val Thr Val Ser Ser
                245

<210> SEQ ID NO 13
<211> LENGTH: 245
<212> TYPE: PRT
<213> ORGANISM: Homo sapiens

<400> SEQUENCE: 13

Asp Ile Gln Met Thr Gln Thr Thr Ser Ser Leu Ser Ala Ser Leu Gly
1               5                   10                  15

```
Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 14
<211> LENGTH: 20
<212> TYPE: PRT
<213> ORGANISM: Homo sapiens

<400> SEQUENCE: 14

Met Glu Thr Asp Thr Leu Leu Leu Trp Val Leu Leu Leu Trp Val Pro
1               5                   10                  15

Gly Ser Thr Gly
            20

<210> SEQ ID NO 15
<211> LENGTH: 23
<212> TYPE: PRT
<213> ORGANISM: Homo sapiens

<400> SEQUENCE: 15

Met Leu Leu Val Thr Ser Leu Leu Leu Cys Glu Leu Pro His Pro Ala
1               5                   10                  15

Phe Leu Leu Ile Pro Asp Thr
            20

<210> SEQ ID NO 16
<211> LENGTH: 21
<212> TYPE: PRT
<213> ORGANISM: Homo sapiens
```

<400> SEQUENCE: 16

Met Gly Thr Ser Leu Leu Cys Trp Met Ala Leu Cys Leu Leu Gly Ala
1               5                   10                  15

Asp His Ala Asp Gly
            20

<210> SEQ ID NO 17
<211> LENGTH: 5
<212> TYPE: PRT
<213> ORGANISM: Homo sapiens

<400> SEQUENCE: 17

Asp Lys Thr His Thr
1               5

<210> SEQ ID NO 18
<211> LENGTH: 4
<212> TYPE: PRT
<213> ORGANISM: Homo sapiens

<400> SEQUENCE: 18

Cys Pro Pro Cys
1

<210> SEQ ID NO 19
<211> LENGTH: 15
<212> TYPE: PRT
<213> ORGANISM: Homo sapiens

<400> SEQUENCE: 19

Cys Pro Glu Pro Lys Ser Cys Asp Thr Pro Pro Pro Cys Pro Arg
1               5                   10                  15

<210> SEQ ID NO 20
<211> LENGTH: 12
<212> TYPE: PRT
<213> ORGANISM: Homo sapiens

<400> SEQUENCE: 20

Glu Leu Lys Thr Pro Leu Gly Asp Thr Thr His Thr
1               5                   10

<210> SEQ ID NO 21
<211> LENGTH: 10
<212> TYPE: PRT
<213> ORGANISM: Homo sapiens

<400> SEQUENCE: 21

Lys Ser Cys Asp Lys Thr His Thr Cys Pro
1               5                   10

<210> SEQ ID NO 22
<211> LENGTH: 7
<212> TYPE: PRT
<213> ORGANISM: Homo sapiens

<400> SEQUENCE: 22

Lys Cys Cys Val Asp Cys Pro
1               5

<210> SEQ ID NO 23
<211> LENGTH: 7
<212> TYPE: PRT

<213> ORGANISM: Homo sapiens

<400> SEQUENCE: 23

Lys Tyr Gly Pro Pro Cys Pro
1               5

<210> SEQ ID NO 24
<211> LENGTH: 15
<212> TYPE: PRT
<213> ORGANISM: Homo sapiens

<400> SEQUENCE: 24

Glu Pro Lys Ser Cys Asp Lys Thr His Thr Cys Pro Pro Cys Pro
1               5                   10                  15

<210> SEQ ID NO 25
<211> LENGTH: 12
<212> TYPE: PRT
<213> ORGANISM: Homo sapiens

<400> SEQUENCE: 25

Glu Arg Lys Cys Cys Val Glu Cys Pro Pro Cys Pro
1               5                   10

<210> SEQ ID NO 26
<211> LENGTH: 17
<212> TYPE: PRT
<213> ORGANISM: Homo sapiens

<400> SEQUENCE: 26

Glu Leu Lys Thr Pro Leu Gly Asp Thr Thr His Thr Cys Pro Arg Cys
1               5                   10                  15

Pro

<210> SEQ ID NO 27
<211> LENGTH: 12
<212> TYPE: PRT
<213> ORGANISM: Homo sapiens

<400> SEQUENCE: 27

Ser Pro Asn Met Val Pro His Ala His His Ala Gln
1               5                   10

<210> SEQ ID NO 28
<211> LENGTH: 12
<212> TYPE: PRT
<213> ORGANISM: Homo sapiens

<400> SEQUENCE: 28

Glu Ser Lys Tyr Gly Pro Pro Cys Pro Pro Cys Pro
1               5                   10

<210> SEQ ID NO 29
<211> LENGTH: 12
<212> TYPE: PRT
<213> ORGANISM: Homo sapiens

<400> SEQUENCE: 29

Glu Ser Lys Tyr Gly Pro Pro Cys Pro Ser Cys Pro
1               5                   10

<210> SEQ ID NO 30
<211> LENGTH: 15
<212> TYPE: PRT

<213> ORGANISM: Homo sapiens

<400> SEQUENCE: 30

Glu Pro Lys Ser Cys Asp Lys Thr Tyr Thr Cys Pro Pro Cys Pro
1               5                   10                  15

<210> SEQ ID NO 31
<211> LENGTH: 45
<212> TYPE: PRT
<213> ORGANISM: Homo sapiens

<400> SEQUENCE: 31

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 32
<211> LENGTH: 24
<212> TYPE: PRT
<213> ORGANISM: Homo sapiens

<400> SEQUENCE: 32

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 33
<211> LENGTH: 23
<212> TYPE: PRT
<213> ORGANISM: Homo sapiens

<400> SEQUENCE: 33

Leu Gly Leu Leu Val Ala Gly Val Leu Val Leu Val Ser Leu Gly
1               5                   10                  15

Val Ala Ile His Leu Cys Cys
            20

<210> SEQ ID NO 34
<211> LENGTH: 25
<212> TYPE: PRT
<213> ORGANISM: Homo sapiens

<400> SEQUENCE: 34

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25

<210> SEQ ID NO 35
<211> LENGTH: 23
<212> TYPE: PRT
<213> ORGANISM: Homo sapiens

<400> SEQUENCE: 35

Leu Cys Tyr Leu Leu Asp Gly Ile Leu Phe Ile Tyr Gly Val Ile Leu
1               5                   10                  15

Thr Ala Leu Phe Leu Arg Val
            20

<210> SEQ ID NO 36
<211> LENGTH: 26
<212> TYPE: PRT
<213> ORGANISM: Homo sapiens

<400> SEQUENCE: 36

Trp Val Leu Val Val Val Gly Gly Val Leu Ala Cys Tyr Ser Leu Leu
1               5                   10                  15

Val Thr Val Ala Phe Ile Ile Phe Trp Val
            20                  25

<210> SEQ ID NO 37
<211> LENGTH: 26
<212> TYPE: PRT
<213> ORGANISM: Homo sapiens

<400> SEQUENCE: 37

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 38
<211> LENGTH: 24
<212> TYPE: PRT
<213> ORGANISM: Homo sapiens

<400> SEQUENCE: 38

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 39
<211> LENGTH: 4
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X is L or I

<400> SEQUENCE: 39

Tyr Xaa Xaa Xaa
1

<210> SEQ ID NO 40
<211> LENGTH: 16
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X is I or L
<220> FEATURE:
<221> NAME/KEY: MISC_FEATURE
<222> LOCATION: (5)..(12)
<223> OTHER INFORMATION: X is any amino acid or absent

```
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: MISC_FEATURE
<222> LOCATION: (16)..(16)
<223> OTHER INFORMATION: X is I or L

<400> SEQUENCE: 40

Tyr Xaa Xaa Xaa Xaa Xaa Xaa Xaa Xaa Xaa Xaa Tyr Xaa Xaa Xaa
1               5                   10                  15

<210> SEQ ID NO 41
<211> LENGTH: 113
<212> TYPE: PRT
<213> ORGANISM: Homo sapiens
<220> FEATURE:
<221> NAME/KEY: MISC_FEATURE
<222> LOCATION: (82)..(82)
<223> OTHER INFORMATION: X is Pyrrolysine
<220> FEATURE:
<221> NAME/KEY: MISC_FEATURE
<222> LOCATION: (92)..(92)
<223> OTHER INFORMATION: X is Pyrrolysine
<220> FEATURE:
<221> NAME/KEY: MISC_FEATURE
<222> LOCATION: (95)..(95)
<223> OTHER INFORMATION: X is Pyrrolysine
<220> FEATURE:
<221> NAME/KEY: MISC_FEATURE
<222> LOCATION: (97)..(97)
<223> OTHER INFORMATION: X is Pyrrolysine

<400> SEQUENCE: 41

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Xaa Arg Ile Thr Glu Thr Glu Ser Pro Tyr Xaa Glu Leu Xaa Gly
                85                  90                  95

Xaa Arg Ser Asp Val Tyr Ser Asp Leu Asn Thr Gln Arg Pro Tyr Tyr
            100                 105                 110

Lys

<210> SEQ ID NO 42
<211> LENGTH: 112
<212> TYPE: PRT
<213> ORGANISM: Homo sapiens
<220> FEATURE:
<221> NAME/KEY: MISC_FEATURE
<222> LOCATION: (81)..(81)
<223> OTHER INFORMATION: X is Pyrrolysine
<220> FEATURE:
<221> NAME/KEY: MISC_FEATURE
<222> LOCATION: (91)..(91)
<223> OTHER INFORMATION: X is Pyrrolysine
<220> FEATURE:
<221> NAME/KEY: MISC_FEATURE
<222> LOCATION: (94)..(94)
<223> OTHER INFORMATION: X is Pyrrolysine
<220> FEATURE:
```

```
<221> NAME/KEY: MISC_FEATURE
<222> LOCATION: (96)..(96)
<223> OTHER INFORMATION: X is Pyrrolysine

<400> SEQUENCE: 42
```

Met Gly Gly Leu Glu Pro Cys Ser Arg Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
            35                  40                  45

Gly Asp Leu Val Leu Thr Val Leu Ile Ala Leu Ala Val Tyr Phe Leu
50                  55                  60

Gly Arg Leu Val Pro Arg Gly Arg Gly Ala Ala Glu Ala Thr Arg Lys
65                  70                  75                  80

Xaa Arg Ile Thr Glu Thr Glu Ser Pro Tyr Xaa Glu Leu Xaa Gly Xaa
                85                  90                  95

Arg Ser Asp Val Tyr Ser Asp Leu Asn Thr Gln Arg Pro Tyr Tyr Lys
            100                 105                 110

```
<210> SEQ ID NO 43
<211> LENGTH: 102
<212> TYPE: PRT
<213> ORGANISM: Homo sapiens
<220> FEATURE:
<221> NAME/KEY: MISC_FEATURE
<222> LOCATION: (71)..(71)
<223> OTHER INFORMATION: X is Pyrrolysine
<220> FEATURE:
<221> NAME/KEY: MISC_FEATURE
<222> LOCATION: (81)..(81)
<223> OTHER INFORMATION: X is Pyrrolysine
<220> FEATURE:
<221> NAME/KEY: MISC_FEATURE
<222> LOCATION: (84)..(84)
<223> OTHER INFORMATION: X is Pyrrolysine
<220> FEATURE:
<221> NAME/KEY: MISC_FEATURE
<222> LOCATION: (86)..(86)
<223> OTHER INFORMATION: X is Pyrrolysine

<400> SEQUENCE: 43
```

Met Gly Gly Leu Glu Pro Cys Ser Arg Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
            35                  40                  45

Ala Val Tyr Phe Leu Gly Arg Leu Val Pro Arg Gly Arg Gly Ala Ala
50                  55                  60

Glu Ala Ala Thr Arg Lys Xaa Arg Ile Thr Glu Thr Glu Ser Pro Tyr
65                  70                  75                  80

Xaa Glu Leu Xaa Gly Xaa Arg Ser Asp Val Tyr Ser Asp Leu Asn Thr
                85                  90                  95

Gln Arg Pro Tyr Tyr Lys
            100

```
<210> SEQ ID NO 44
<211> LENGTH: 101
<212> TYPE: PRT
<213> ORGANISM: Homo sapiens
<220> FEATURE:
<221> NAME/KEY: MISC_FEATURE
```

```
<222> LOCATION: (70)..(70)
<223> OTHER INFORMATION: X is Pyrrolysine
<220> FEATURE:
<221> NAME/KEY: MISC_FEATURE
<222> LOCATION: (80)..(80)
<223> OTHER INFORMATION: X is Pyrrolysine
<220> FEATURE:
<221> NAME/KEY: MISC_FEATURE
<222> LOCATION: (83)..(83)
<223> OTHER INFORMATION: X is Pyrrolysine
<220> FEATURE:
<221> NAME/KEY: MISC_FEATURE
<222> LOCATION: (85)..(85)
<223> OTHER INFORMATION: X is Pyrrolysine

<400> SEQUENCE: 44

Met Gly Gly Leu Glu Pro Cys Ser Arg Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Thr Arg Lys Xaa Arg Ile Thr Glu Thr Ser Pro Tyr Xaa
65                  70                  75                  80

Glu Leu Xaa Gly Xaa Arg Ser Asp Val Tyr Ser Asp Leu Asn Thr Gln
                85                  90                  95

Arg Pro Tyr Tyr Lys
            100

<210> SEQ ID NO 45
<211> LENGTH: 21
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is Pyrrolysine
<220> FEATURE:
<221> NAME/KEY: MISC_FEATURE
<222> LOCATION: (8)..(8)
<223> OTHER INFORMATION: X is Pyrrolysine
<220> FEATURE:
<221> NAME/KEY: MISC_FEATURE
<222> LOCATION: (10)..(10)
<223> OTHER INFORMATION: X is Pyrrolysine
<220> FEATURE:
<221> NAME/KEY: MISC_FEATURE
<222> LOCATION: (21)..(21)
<223> OTHER INFORMATION: X is Pyrrolysine

<400> SEQUENCE: 45

Glu Ser Pro Tyr Xaa Glu Leu Xaa Gly Xaa Arg Ser Asp Val Tyr Ser
1               5                   10                  15

Asp Leu Asn Thr Xaa
            20

<210> SEQ ID NO 46
<211> LENGTH: 86
<212> TYPE: PRT
<213> ORGANISM: Homo sapiens

<400> SEQUENCE: 46

Met Ile Pro Ala Val Val Leu Leu Leu Leu Leu Val Glu Gln Ala
1               5                   10                  15
```

-continued

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 47
<211> LENGTH: 21
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: X is Pyrrolysine

<400> SEQUENCE: 47

Asp Gly Val Tyr Thr Gly Leu Ser Thr Arg Asn Xaa Glu Thr Tyr Glu
1               5                   10                  15

Thr Leu Lys His Glu
            20

<210> SEQ ID NO 48
<211> LENGTH: 171
<212> TYPE: PRT
<213> ORGANISM: Homo sapiens
<220> FEATURE:
<221> NAME/KEY: MISC_FEATURE
<222> LOCATION: (140)..(140)
<223> OTHER INFORMATION: X is Pyrrolysine
<220> FEATURE:
<221> NAME/KEY: MISC_FEATURE
<222> LOCATION: (147)..(147)
<223> OTHER INFORMATION: X is Pyrrolysine
<220> FEATURE:
<221> NAME/KEY: MISC_FEATURE
<222> LOCATION: (150)..(150)
<223> OTHER INFORMATION: X is Pyrrolysine
<220> FEATURE:
<221> NAME/KEY: MISC_FEATURE
<222> LOCATION: (159)..(159)
<223> OTHER INFORMATION: X is Pyrrolysine

<400> SEQUENCE: 48

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His

```
                    115                 120                 125
Glu Thr Gly Arg Leu Ser Gly Ala Ala Asp Thr Xaa Ala Leu Leu Arg
            130                 135                 140

Asn Asp Xaa Val Tyr Xaa Pro Leu Arg Asp Arg Asp Asp Ala Xaa Tyr
145                 150                 155                 160

Ser His Leu Gly Gly Asn Trp Ala Arg Asn Lys
                165                 170
```

<210> SEQ ID NO 49
<211> LENGTH: 127
<212> TYPE: PRT
<213> ORGANISM: Homo sapiens
<220> FEATURE:
<221> NAME/KEY: MISC_FEATURE
<222> LOCATION: (87)..(87)
<223> OTHER INFORMATION: X is Pyrrolysine
<220> FEATURE:
<221> NAME/KEY: MISC_FEATURE
<222> LOCATION: (96)..(96)
<223> OTHER INFORMATION: X is Pyrrolysine
<220> FEATURE:
<221> NAME/KEY: MISC_FEATURE
<222> LOCATION: (103)..(103)
<223> OTHER INFORMATION: X is Pyrrolysine
<220> FEATURE:
<221> NAME/KEY: MISC_FEATURE
<222> LOCATION: (106)..(106)
<223> OTHER INFORMATION: X is Pyrrolysine

<400> SEQUENCE: 49

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Xaa Val His Tyr Arg Thr Ala Asp Thr Xaa
                85                  90                  95

Ala Leu Leu Arg Asn Asp Xaa Val Tyr Xaa Pro Leu Arg Asp Arg Asp
            100                 105                 110

Asp Ala Gln Tyr Ser His Leu Gly Gly Asn Trp Ala Arg Asn Lys
        115                 120                 125
```

<210> SEQ ID NO 50
<211> LENGTH: 21
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is Pyrrolysine
<220> FEATURE:
<221> NAME/KEY: MISC_FEATURE
<222> LOCATION: (5)..(5)
<223> OTHER INFORMATION: X is Pyrrolysine
<220> FEATURE:
<221> NAME/KEY: MISC_FEATURE
<222> LOCATION: (14)..(14)
<223> OTHER INFORMATION: X is Pyrrolysine

<400> SEQUENCE: 50

```
Asp Xaa Val Tyr Xaa Pro Leu Arg Asp Arg Asp Asp Ala Xaa Tyr Ser
1               5                   10                  15

His Leu Gly Gly Asn
            20

<210> SEQ ID NO 51
<211> LENGTH: 207
<212> TYPE: PRT
<213> ORGANISM: Homo sapiens

<400> SEQUENCE: 51

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 52
<211> LENGTH: 21
<212> TYPE: PRT
<213> ORGANISM: Homo sapiens

<400> SEQUENCE: 52

Asn Pro Asp Tyr Glu Pro Ile Arg Lys Gly Gln Arg Asp Leu Tyr Ser
1               5                   10                  15

Gly Leu Asn Gln Arg
            20

<210> SEQ ID NO 53
<211> LENGTH: 182
<212> TYPE: PRT
<213> ORGANISM: Homo sapiens
<220> FEATURE:
<221> NAME/KEY: MISC_FEATURE
<222> LOCATION: (139)..(139)
<223> OTHER INFORMATION: X is Pyrrolysine
<220> FEATURE:
<221> NAME/KEY: MISC_FEATURE
<222> LOCATION: (144)..(144)
```

<223> OTHER INFORMATION: X is Pyrrolysine
<220> FEATURE:
<221> NAME/KEY: MISC_FEATURE
<222> LOCATION: (151)..(151)
<223> OTHER INFORMATION: X is Pyrrolysine
<220> FEATURE:
<221> NAME/KEY: MISC_FEATURE
<222> LOCATION: (158)..(158)
<223> OTHER INFORMATION: X is Pyrrolysine
<220> FEATURE:
<221> NAME/KEY: MISC_FEATURE
<222> LOCATION: (161)..(161)
<223> OTHER INFORMATION: X is Pyrrolysine

<400> SEQUENCE: 53

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Xaa Asp Gly Val Arg Xaa
    130                 135                 140

Ser Arg Ala Ser Asp Lys Xaa Thr Leu Leu Pro Asn Asp Xaa Leu Tyr
145                 150                 155                 160

Xaa Pro Leu Lys Asp Arg Glu Asp Asp Gln Tyr Ser His Leu Gln Gly
                165                 170                 175

Asn Gln Leu Arg Arg Asn
            180
```

<210> SEQ ID NO 54
<211> LENGTH: 21
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is Pyrrolysine
<220> FEATURE:
<221> NAME/KEY: MISC_FEATURE
<222> LOCATION: (5)..(5)
<223> OTHER INFORMATION: X is Pyrrolysine
<220> FEATURE:
<221> NAME/KEY: MISC_FEATURE
<222> LOCATION: (14)..(14)
<223> OTHER INFORMATION: X is Pyrrolysine
<220> FEATURE:
<221> NAME/KEY: MISC_FEATURE
<222> LOCATION: (19)..(19)
<223> OTHER INFORMATION: X is Pyrrolysine

<400> SEQUENCE: 54

```
Asp Xaa Leu Tyr Xaa Pro Leu Lys Asp Arg Glu Asp Asp Xaa Tyr Ser
1               5                   10                  15
```

-continued

```
His Leu Xaa Gly Asn
            20
```

```
<210> SEQ ID NO 55
<211> LENGTH: 163
<212> TYPE: PRT
<213> ORGANISM: Homo sapiens
<220> FEATURE:
<221> NAME/KEY: MISC_FEATURE
<222> LOCATION: (114)..(114)
<223> OTHER INFORMATION: X is Pyrrolysine
<220> FEATURE:
<221> NAME/KEY: MISC_FEATURE
<222> LOCATION: (142)..(142)
<223> OTHER INFORMATION: X is Pyrrolysine

<400> SEQUENCE: 55

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Xaa Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Xaa Gly Leu
    130                 135                 140

Ser Thr Ala Thr Lys Asp Thr Tyr Asp Ala Leu His Met Gln Ala Leu
145                 150                 155                 160

Pro Pro Arg
```

```
<210> SEQ ID NO 56
<211> LENGTH: 164
<212> TYPE: PRT
<213> ORGANISM: Homo sapiens
<220> FEATURE:
<221> NAME/KEY: MISC_FEATURE
<222> LOCATION: (115)..(115)
<223> OTHER INFORMATION: X is Pyrrolysine
<220> FEATURE:
<221> NAME/KEY: MISC_FEATURE
<222> LOCATION: (143)..(143)
<223> OTHER INFORMATION: X is Pyrrolysine

<400> SEQUENCE: 56

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60
```

```
Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Arg Gly Arg Asp Pro Glu Met
                 85                  90                  95

Gly Gly Lys Pro Gln Arg Arg Lys Asn Pro Gln Glu Gly Leu Tyr Asn
            100                 105                 110

Glu Leu Xaa Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Xaa Gly
130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 57
<211> LENGTH: 21
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is Pyrrolysine

<400> SEQUENCE: 57

Asn Xaa Leu Tyr Asn Glu Leu Asn Leu Gly Arg Arg Glu Glu Tyr Asp
 1               5                  10                  15

Val Leu Asp Lys Arg
             20

<210> SEQ ID NO 58
<211> LENGTH: 22
<212> TYPE: PRT
<213> ORGANISM: Homo sapiens

<400> SEQUENCE: 58

Glu Gly Leu Tyr Asn Glu Leu Gln Lys Asp Lys Met Ala Glu Ala Tyr
 1               5                  10                  15

Ser Glu Ile Gly Met Lys
             20

<210> SEQ ID NO 59
<211> LENGTH: 21
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is Pyrrolysine
<220> FEATURE:
<221> NAME/KEY: MISC_FEATURE
<222> LOCATION: (21)..(21)
<223> OTHER INFORMATION: X is Pyrrolysine

<400> SEQUENCE: 59

Asp Gly Leu Tyr Xaa Gly Leu Ser Thr Ala Thr Lys Asp Thr Tyr Asp
 1               5                  10                  15

Ala Leu His Met Xaa
             20

<210> SEQ ID NO 60
<211> LENGTH: 226
<212> TYPE: PRT
<213> ORGANISM: Homo sapiens
```

```
<220> FEATURE:
<221> NAME/KEY: MISC_FEATURE
<222> LOCATION: (170)..(170)
<223> OTHER INFORMATION: X is Pyrrolysine
<220> FEATURE:
<221> NAME/KEY: MISC_FEATURE
<222> LOCATION: (207)..(207)
<223> OTHER INFORMATION: X is Pyrrolysine

<400> SEQUENCE: 60

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Xaa Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Xaa Gly
        195                 200                 205

Thr Tyr Gln Asp Val Gly Ser Leu Asn Ile Gly Asp Val Gln Leu Glu
    210                 215                 220

Lys Pro
225

<210> SEQ ID NO 61
<211> LENGTH: 188
<212> TYPE: PRT
<213> ORGANISM: Homo sapiens

<400> SEQUENCE: 61

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
    50                  55                  60

Thr Trp Trp Arg Val Leu His Gly Asn Tyr Thr Trp Pro Pro Glu Phe
65                  70                  75                  80
```

```
Leu Gly Pro Gly Glu Asp Pro Asn Glu Pro Pro Arg Pro Phe Leu
            85                  90                  95

Asp Met Gly Glu Gly Thr Lys Asn Arg Ile Ile Thr Ala Glu Gly Ile
        100                 105                 110

Ile Leu Leu Phe Cys Ala Val Val Pro Gly Thr Leu Leu Leu Phe Arg
            115                 120                 125

Lys Arg Trp Gln Asn Glu Lys Leu Gly Leu Asp Ala Gly Asp Glu Tyr
        130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185

<210> SEQ ID NO 62
<211> LENGTH: 21
<212> TYPE: PRT
<213> ORGANISM: Homo sapiens

<400> SEQUENCE: 62

Glu Asn Leu Tyr Glu Gly Leu Asn Leu Asp Asp Cys Ser Met Tyr Glu
1               5                   10                  15

Asp Ile Ser Arg Gly
            20

<210> SEQ ID NO 63
<211> LENGTH: 20
<212> TYPE: PRT
<213> ORGANISM: Homo sapiens

<400> SEQUENCE: 63

Arg Pro Arg Arg Ser Pro Ala Gln Asp Gly Lys Val Tyr Ile Asn Met
1               5                   10                  15

Pro Gly Arg Gly
            20

<210> SEQ ID NO 64
<211> LENGTH: 20
<212> TYPE: PRT
<213> ORGANISM: Homo sapiens

<400> SEQUENCE: 64

Arg Pro Arg Arg Ser Pro Ala Gln Asp Gly Lys Val Tyr Ile Asn Met
1               5                   10                  15

Pro Gly Arg Gly
            20

<210> SEQ ID NO 65
<211> LENGTH: 68
<212> TYPE: PRT
<213> ORGANISM: Homo sapiens

<400> SEQUENCE: 65

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45
```

-continued

```
Pro Thr Arg Lys His Tyr Gln Pro Tyr Ala Pro Pro Arg Asp Phe Ala
    50                  55                  60

Ala Tyr Arg Ser
65

<210> SEQ ID NO 66
<211> LENGTH: 68
<212> TYPE: PRT
<213> ORGANISM: Homo sapiens

<400> SEQUENCE: 66

Phe Trp Val Leu Val Val Gly Gly Val Leu Ala Cys Tyr Ser Leu
1               5                   10                  15

Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 67
<211> LENGTH: 619
<212> TYPE: PRT
<213> ORGANISM: Homo sapiens

<400> SEQUENCE: 67

Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220
```

```
Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
        260                 265                 270

His Pro Ser Thr Leu Thr His Pro Gln Arg Arg Ile Asp Thr Leu Asn
                275                 280                 285

Ser Asp Gly Tyr Thr Pro Glu Pro Ala Arg Ile Thr Ser Pro Asp Lys
290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
                340                 345                 350

Arg Gln Gly Val Tyr Arg Met Arg Lys Lys Gln Ile Asp Val Ala Ile
                355                 360                 365

Lys Val Leu Lys Gln Gly Thr Glu Lys Ala Asp Thr Glu Glu Met Met
370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
                420                 425                 430

Ile Pro Val Ser Asn Val Ala Glu Leu Leu His Gln Val Ser Met Gly
                435                 440                 445

Met Lys Tyr Leu Glu Glu Lys Asn Phe Val His Arg Asp Leu Ala Ala
450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
                500                 505                 510

Phe Arg Lys Phe Ser Ser Arg Ser Asp Val Trp Ser Tyr Gly Val Thr
                515                 520                 525

Met Trp Glu Ala Leu Ser Tyr Gly Gln Lys Pro Tyr Lys Lys Met Lys
530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
                580                 585                 590

Met Arg Ala Cys Tyr Tyr Ser Leu Ala Ser Lys Val Glu Gly Pro Pro
                595                 600                 605

Gly Ser Thr Gln Lys Ala Glu Ala Cys Ala
                610                 615

<210> SEQ ID NO 68
<211> LENGTH: 9
```

```
<212> TYPE: PRT
<213> ORGANISM: Homo sapiens

<400> SEQUENCE: 68

Tyr Pro Tyr Asp Val Pro Asp Tyr Ala
1               5

<210> SEQ ID NO 69
<211> LENGTH: 8
<212> TYPE: PRT
<213> ORGANISM: Homo sapiens

<400> SEQUENCE: 69

Asp Tyr Lys Asp Asp Asp Asp Lys
1               5

<210> SEQ ID NO 70
<211> LENGTH: 10
<212> TYPE: PRT
<213> ORGANISM: Homo sapiens

<400> SEQUENCE: 70

Glu Gln Lys Leu Ile Ser Glu Glu Asp Leu
1               5                   10

<210> SEQ ID NO 71
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Sequence may repeat n times

<400> SEQUENCE: 71

Gly Ser Gly Gly Ser
1               5

<210> SEQ ID NO 72
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Sequence may repeat n times

<400> SEQUENCE: 72

Gly Gly Gly Ser
1

<210> SEQ ID NO 73
<211> LENGTH: 4
<212> TYPE: PRT
<213> ORGANISM: Homo sapiens

<400> SEQUENCE: 73

Gly Gly Ser Gly
1

<210> SEQ ID NO 74
<211> LENGTH: 5
<212> TYPE: PRT
<213> ORGANISM: Homo sapiens

<400> SEQUENCE: 74
```

```
Gly Gly Ser Gly Gly
1               5

<210> SEQ ID NO 75
<211> LENGTH: 5
<212> TYPE: PRT
<213> ORGANISM: Homo sapiens

<400> SEQUENCE: 75

Gly Ser Gly Ser Gly
1               5

<210> SEQ ID NO 76
<211> LENGTH: 5
<212> TYPE: PRT
<213> ORGANISM: Homo sapiens

<400> SEQUENCE: 76

Gly Ser Gly Gly Gly
1               5

<210> SEQ ID NO 77
<211> LENGTH: 5
<212> TYPE: PRT
<213> ORGANISM: Homo sapiens

<400> SEQUENCE: 77

Gly Gly Gly Ser Gly
1               5

<210> SEQ ID NO 78
<211> LENGTH: 5
<212> TYPE: PRT
<213> ORGANISM: Homo sapiens

<400> SEQUENCE: 78

Gly Ser Ser Ser Gly
1               5

<210> SEQ ID NO 79
<211> LENGTH: 42
<212> TYPE: PRT
<213> ORGANISM: Homo sapiens

<400> SEQUENCE: 79

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 80
<211> LENGTH: 44
<212> TYPE: PRT
<213> ORGANISM: Homo sapiens

<400> SEQUENCE: 80

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
```

```
            35                  40
```

<210> SEQ ID NO 81
<211> LENGTH: 35
<212> TYPE: PRT
<213> ORGANISM: Homo sapiens

<400> SEQUENCE: 81

```
Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35
```

<210> SEQ ID NO 82
<211> LENGTH: 37
<212> TYPE: PRT
<213> ORGANISM: Homo sapiens

<400> SEQUENCE: 82

```
Arg Arg Asp Gln Arg Leu Pro Pro Asp Ala His Lys Pro Gly Gly Gly
1               5                   10                  15

Gly Ser Phe Arg Thr Pro Ile Gln Glu Gln Ala Asp Ala His Ser
            20                  25                  30

Thr Leu Ala Lys Ile
        35
```

<210> SEQ ID NO 83
<211> LENGTH: 114
<212> TYPE: PRT
<213> ORGANISM: Homo sapiens

<400> SEQUENCE: 83

```
Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45

Gly Ile Tyr Asp Asn Asp Pro Asp Leu Cys Phe Arg Met Gln Glu Gly
    50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser
```

<210> SEQ ID NO 84
<211> LENGTH: 49
<212> TYPE: PRT
<213> ORGANISM: Homo sapiens

<400> SEQUENCE: 84

```
His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
```

```
            20                  25                  30

Thr Ile Pro Ile Gln Glu Asp Tyr Arg Lys Pro Glu Pro Ala Cys Ser
        35                  40                  45

Pro

<210> SEQ ID NO 85
<211> LENGTH: 187
<212> TYPE: PRT
<213> ORGANISM: Homo sapiens

<400> SEQUENCE: 85

Arg Arg Ala Cys Arg Lys Arg Ile Arg Gln Lys Leu His Leu Cys Tyr
1               5                  10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
    50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
        115                 120                 125

Gly Arg Gly Leu Ala Gly Pro Ala Glu Pro Glu Leu Glu Glu Glu Leu
    130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Glu Gly Lys
                165                 170                 175

Glu Asp Pro Leu Pro Thr Ala Ala Ser Gly Lys
            180                 185

<210> SEQ ID NO 86
<211> LENGTH: 54
<212> TYPE: PRT
<213> ORGANISM: Homo sapiens

<400> SEQUENCE: 86

His Ile Trp Gln Leu Arg Ser Gln Cys Met Trp Pro Arg Glu Thr Gln
1               5                  10                  15

Leu Leu Leu Glu Val Pro Pro Ser Thr Glu Asp Ala Arg Ser Cys Gln
            20                  25                  30

Phe Pro Glu Glu Arg Gly Glu Arg Ser Ala Glu Glu Lys Gly Arg
        35                  40                  45

Leu Gly Asp Leu Trp Val
    50

<210> SEQ ID NO 87
<211> LENGTH: 60
<212> TYPE: PRT
<213> ORGANISM: Homo sapiens

<400> SEQUENCE: 87
```

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 88
<211> LENGTH: 1422
<212> TYPE: DNA
<213> ORGANISM: Homo sapiens

<400> SEQUENCE: 88

| | | | | |
|---|---|---|---|---|
| atgctgctgc | tggtgaccag | cctgctgctg | tgcgagctgc | cccaccccgc | ctttctgctg |   60 |
| atccccggcg | aagttaccc | atatgacgtt | cccgactacg | ctggcgacat | ccagatgacc |  120 |
| cagaccacct | ccagcctgag | cgccagcctg | ggcgaccggg | tgaccatcag | ctgccgggcc |  180 |
| agccaggaca | tcagcaagta | cctgaactgg | tatcagcaga | agcccgacgg | caccgtcaag |  240 |
| ctgctgatct | accacaccag | ccggctgcac | agcggcgtgc | ccagccggtt | tagcggcagc |  300 |
| ggctccggca | ccgactacag | cctgaccatc | tccaacctgg | aacaggaaga | tatcgccacc |  360 |
| tactttgcc | agcagggcaa | cacactgccc | tacacctttg | gcggcggaac | aaagctggaa |  420 |
| atcaccggca | gcacctccgg | cagcggcaag | cctggcagcg | gcgagggcag | caccaagggc |  480 |
| gaggtgaagc | tgcaggaaag | cggccctggc | ctggtggccc | ccagccagag | cctgagcgtg |  540 |
| acctgcaccg | tgagcggcgt | gagcctgccc | gactacggcg | tgagctggat | ccggcagccc |  600 |
| cccaggaagg | gcctggaatg | gctgggcgtg | atctggggca | gcgagaccac | ctactacaac |  660 |
| agcgccctga | agagccggct | gaccatcatc | aaggacaaca | gcaagagcca | ggtgttcctg |  720 |
| aagatgaaca | gcctgcagac | cgacgacacc | gccatctact | actgcgccaa | gcactactac |  780 |
| tacggcggca | gctacgccat | ggactactgg | ggccagggca | ccagcgtgac | cgtgagcagc |  840 |
| gaatctaagt | acggaccgcc | ctgccccct | tgccctatgt | tctgggtgct | ggtggtggtc |  900 |
| ggaggcgtgc | tggcctgcta | cagcctgctg | gtcaccgtgg | ccttcatcat | cttttgggtg |  960 |
| aaacggggca | gaaagaaact | cctgtatata | ttcaaacaac | catttatgag | accagtacaa |  1020 |
| actactcaag | aggaagatgg | ctgtagctgc | cgatttccag | aagaagaaga | aggaggatgt |  1080 |
| gaactgcggg | tgaagttcag | cagaagcgcc | gacgccctg | cctaccagca | gggccagaat |  1140 |
| cagctgtaca | acgagctgaa | cctgggcaga | agggaagagt | acgacgtcct | ggataagcgg |  1200 |
| agaggccggg | accctgagat | gggcggcaag | cctcggcgga | agaaccccca | ggaaggcctg |  1260 |
| tataacgaac | tgcagaaaga | caagatggcc | gaggcctaca | gcgagatcgg | catgaagggc |  1320 |
| gagcggaggc | ggggcaaggg | ccacgacggc | ctgtatcagg | cctgtccac | cgccaccaag |  1380 |
| gatacctacg | acgccctgca | catgcaggcc | ctgccccaa | gg |  1422 |

<210> SEQ ID NO 89
<211> LENGTH: 2145
<212> TYPE: DNA
<213> ORGANISM: Homo sapiens

<400> SEQUENCE: 89

| | | | | |
|---|---|---|---|---|
| atggagacag | acacactcct | gctatgggtg | ctgctgctct | gggttccagg | ttccacaggt |   60 |
| gacggaggca | gcgactataa | agatgacgat | gacaaggag | gtagcgatat | acaaatgact |  120 |

```
caatcacctt cctcactttc cgccagcgtg ggtgatcgag tgaccatcac atgccgcgct    180
tcacaggaca tctcctctta cctgaactgg taccagcaga aacccgggaa agccccaaag    240
ctgttgatct actatacatc aagactgcac tctggcgtcc cctctaggtt cagtggatct    300
ggctcaggta ctgacttcac gttcactatt tccagcctgc agccggaaga tattgctacc    360
tactattgtc agcagggaaa taccctccca tataccttg ggcaggggac aaaggtggaa     420
atcaagcgga cggtagctgc tccgtcagtg ttcatctttc caccttcaga tgagcagctg    480
aagtccggaa ccgccagtgt ggtgtgcctc ctgaataact tttatccacg agaagccaag    540
gtgcagtgga aagtggataa cgctttgcaa agtggcaatt ctcaagagag cgtaactgag    600
caagatagca aggacagtac ttacagcttg agcagcacgc tgaccctgag caaggccgat    660
tacgagaaac acaaggtgta tgcctgcgag gtgacccacc agggccttag ctcacctgtg    720
accaagtcct tcaacagagg cgagtgtggc agcacctccg gcagcggcaa gcctggcagc    780
ggcgagggca gcaccaaggg cgaggtccaa ctgcaggaaa gcggtccagg cttggtgaga    840
ccatcccaga ccctgagcct cacctgtacc gtgtccgggt acagtatcac ctccgaccat    900
gcatggtcct gggtgcgcca gcctcccgga agaggtctgg aatggatcgg gtatatctcc    960
tactcaggaa tcaccaccta caatccctcc cttaagtcaa gggtgactat gctccgcgat   1020
acatccaaaa atcagttctc ccttcggttg tcaagtgtta cagccgccga caccgcagtc   1080
tactactgtg caaggagcct cgccaggacg actgcaatgg attattgggg ccagggctcc   1140
ctggtgactg tcagcagcgc ctcaacaaag gcccatctg ttttccact tgccccaagc     1200
tctaaaagta cctcaggagg aaccgctgcc ctcgggtgcc tcgtcaaaga ttactttcca   1260
gaacccgtta cagtgtcctg gaactccgga gctcttacct ccggggtgca tacattcccg   1320
gccgttcttc aaagctctgg actctactcc ctgagctccg ttgtgacagt tcctagcagc   1380
agcctcggca cccagacata catctgcaac gtaaaccaca agccttcaaa cactaaagtg   1440
gacaaaaaag tggaaccgaa gtcctgtgac aaaactcaca catgcccctcc gtgccctgcc   1500
ccagagctgc tgggcgggcc atccgtattt ctcttccctc caaagccaaa ggataccctc   1560
atgatcagcc ggacgcccga agtgacctgc gtcgtagtgg atgtgagtca cgaggaccca   1620
gaggtaaagt tcaactggta cgtagacggc gtggaggtcc ataatgcgaa gacgaaaccc   1680
agagaggagc agtacaactc aacttacaga gtggtcagcg tgctcactgt cctccaccag   1740
gactggttga acggcaaaga atataagtgt aaggtgagca ataaggccct ccccgcccct   1800
atcgagaaaa ctatttccaa ggctaaaggc cagcctcgag aacctcaggt ttacacactg    1860
cctcctagcc gcgatgaact gacaaaaaat caggtgagtc tcacctgcct cgttaaaggt    1920
ttctacccctt cagatatcgc agtcgagtgg gagagcaacg ggcagccgga aaataactat    1980
aagaccaccc ccccagtcct tgacagtgac ggctctttct tcctgtactc caaactgacc   2040
gtggacaaat ctaggtggca gcaaggaaat gtttttagtt gttctgtaat gcacgaggct   2100
ctgcataatc attataccca aaagtctttg tccctctccc ccggc                    2145
```

METHODS AND COMPOSITIONS INVOLVING INTERLEUKIN-6 RECEPTOR ALPHA-BINDING SINGLE CHAIN VARIABLE FRAGMENTS

CROSS-REFERENCE TO RELATED APPLICATIONS

This application is a national phase application under 35 U.S.C. § 371 of International Application No. PCT/IB2017/055281, filed Sep. 1, 2017, which claims the benefit of U.S. Provisional Patent Application No. 62/383,237, filed Sep. 2, 2016, U.S. Provisional Patent Application No. 62/440,991, filed Dec. 30, 2016, and U.S. Provisional Patent Application No. 62/443,509, filed Jan. 6, 2017. The entire contents of each of these applications are incorporated herein by reference.

SEQUENCE LISTING

The instant application contains a Sequence Listing which has been submitted electronically in ASCII format and is hereby incorporated by reference in its entirety. Said ASCII copy, created on May 19, 2023, is named UCLAP0043US_ST25.txt and is 77,824 bytes in size.

CROSS-REFERENCE TO RELATED APPLICATIONS

This application claims the benefit of U.S. Provisional Patent Application No. 62/383,237, filed Sep. 2, 2016, U.S. Provisional Patent Application No. 62/440,991, filed Dec. 30, 2016, and U.S. Provisional Patent Application No. 62/443,509, filed Jan. 6, 2017. The entire contents of which applications are incorporated herein by reference.

BACKGROUND OF THE INVENTION

The prospects of using antibodies that interact with T-cells for employing new and effective therapies for the treatment of a variety of diseases and conditions, including cancer, microbial infections, and autoimmune diseases, continue to develop. However, there are side effects and toxicities that can result, including cytokine release syndrome (CRS). CRS can cause a patient to experience hypotension, pyrexia, and rigors (a sudden feeling of cold with shivering accompanied by a rise in temperature) similar to the onset of a high fever. Treatments are needed that will prevent or alleviate the side effects and toxicities from T-cell engaging therapies.

SUMMARY OF THE INVENTION

Embodiments are provided in the form of methods, compositions, medical devices, and kits involving an isolated and engineered chimeric interleukin 6 receptor alpha (IL-6Rα) binding protein.

Compositions, medical devices, and kits include therapeutic compositions or a kit that has at least one therapeutic composition that comprises one or more of the following: an isolated chimeric interleukin 6 receptor alpha (IL-6Rα) binding protein, a nucleic acid encoding a chimeric IL-6Rα binding protein, one or more cells expressing a chimeric IL-6Rα binding protein, or one or more cells that have a nucleic acid encoding a chimeric IL-6Rα binding protein.

In some embodiments, there is a chimeric interleukin 6 receptor alpha (IL-6Rα) binding protein comprising a heavy chain variable region comprising CDR1 (SEQ ID NO:5), CDR2 (SEQ ID NO:6), and CDR3 (SEQ ID NO:7) attached by a heterologous linker to a light chain variable region comprising CDR4 (SEQ ID NO:8), CDR5 (SEQ ID NO:9), and CDR6 (SEQ ID NO:10). In some embodiments, a chimeric IL-6Rα binding protein has at least or at most 1, 2, 3, 4, 5, or 6 amino acid substitutions, deletions, or additions in one or more of CDR1, CDR2, CDR3, CDR4, CDR5, and/or CDR6. In other embodiments, a chimeric IL-6Rα binding protein has 60, 65, 70, 75, 80, 81, 82, 83, 84, 85, 86, 87, 88, 89, 90, 91, 92, 93, 94, 95, 96, 97, 98, 99 or 100% (or any range derivable therein) sequence identity with the amino acid sequence of CDR1, CDR2, CDR3, CDR4, CDR5, and/or CDR6 or with the heavy chain variable domain (SEQ ID NO:3) or with light chain variable domain (SEQ ID NO:4) or with the $V_L$-$V_H$ single chain variable fragment (scFv) (SEQ ID NO:1) or with the $V_H$-$V_L$ scFv (SEQ ID NO:2). In certain embodiments the chimeric IL-6Rα binding protein is isolated and/or purified. In some embodiments, the IL6Rα binding protein comprises SEQ ID NO:1 or SEQ ID NO:2. Further embodiments concern an scFv that is essentially or comprises SEQ ID NO:1 or SEQ ID NO:2.

In some embodiments, the chimeric IL-6Rα binding protein is an scFv, (scFv)$_2$, scFvFc, Fab, Fab', or F(ab)$_2$. In some cases, the scFv portion comprises all or part of SEQ ID NOs:1-10. In certain embodiments, the protein is 1, 2, 3, 4 or more polypeptides. In specific embodiments, the IL-6Rα binding protein is one polypeptide. In other specific embodiments, the chimeric chimeric IL-6Rα binding protein is a fusion protein. In some embodiments, the fusion protein is one polypeptide.

Certain embodiments concern a chimeric IL-6Rα binding protein that is a single chain variable fragment (scFv). In embodiments involving a single polypeptide containing both a heavy chain variable region and a light chain variable region, both orientations of these variable regions are contemplated. In some cases, the heavy chain variable region is on the N-terminal side of the light chain variable region, which means the heavy chain variable region is closer to the N-terminus of the polypeptide. SEQ ID NO:2 is an example of this configuration. In other cases, the light chain variable region is on the N-terminal side of the heavy chain variable region, which means the light chain variable region is closer to the N-terminus of the polypeptide than the heavy chain variable region. SEQ ID NO:1 is an example of this structure.

In some embodiments, a chimeric IL-6Rα binding protein comprises a linker. In some cases, the linker is between the heavy chain variable region and the light chain variable region (or vice versa). The linker comprises the amino acid sequence GSTSGSGKPGSGEGSTKG (SEQ ID NO:11) in some embodiments or has 10, 11, 12, 13, 14, 15, 16, 17, or 18 contiguous amino acids from the sequence of SEQ ID NO:11. In other embodiments, the linker is 80, 81, 82, 83, 84, 85, 86, 87, 88, 89, 90, 91, 92, 93, 94, 95, 96, 97, 98, 99 or 100% identical in amino acid sequence to SEQ ID NO:11.

Some chimeric IL-6Rα binding proteins also have a leader or signal peptide at or toward the N-terminus of a polypeptide. The leader or signal peptide refers to a short (5-30 amino acids long) peptide present at the N-terminus of a polypeptide to promote or allow for secretion of that polypeptide.

In particular embodiments, a chimeric IL-6Rα binding protein may include an isolation tag, which refers to a peptide tag that is used to isolate or purify the protein or polypeptide. The tag may or may not be removable, such as by cleavage. The tag may be a chitin binding protein (CBP), a maltose binding protein (MBP), glutathione-S-transferase (GST), a His tag (such as Hisx6). In some instances, the isolation tag is a chromatography tag that is used to alter chromatographic properties of the protein to afford different resolution across a particular separation technique. An example of this is a FLAG tag such as DYKDDDDK (SEQ ID NO:69), which is a series of polyanionic amino acids. Another isolation tag may be an epitope tag, which refers to a short peptide sequence can be used in conjunction with an antibody. Epitope tags include, but are not limited to, a V5 tag, a c-myc tag, an HA tag, or an NE tag.

Some embodiments involve an isolated chimeric interleukin 6 receptor alpha (IL-6Rα) binding protein comprising a leader peptide, heavy chain variable region comprising CDR1 (SEQ ID NO:5), CDR2 (SEQ ID NO:6), and CDR3 (SEQ ID NO:7) attached by a heterologous linker to a light chain variable region comprising CDR4 (SEQ ID NO:8), CDR5 (SEQ ID NO:9), and CDR6 (SEQ ID NO:10), wherein the heterologous linker comprises the amino acid sequence GSTSGSGKPGSGEGSTKG (SEQ ID NO:11) and the IL-6Rα binding protein is a single-chain variable fragment (scFv). Embodiments do not involve tocilizumab (also known as atlizumab), which is sold under the trade names of Actemra and RoActemra and is a humanized monoclonal antibody unless specifically included. In specific embodiments, the IL-6Rα binding protein reduces the expression of one or more cytokines from a T cell. In some embodiments, the T cell expresses a chimeric antigen receptor or another protein that activates T cells. In certain embodiments, the IL-6Rα binding protein reduces the expression of any of the following cytokines: TNF-α, IL-6, IL-2, IL-4, and GM-CSF (or any combination thereof). In some instances, an IL-6Rα binding protein reduces the expression of one or more of those cytokines by, by at least, or by at most 10%, 20%, 30%, 40%, or 50% (or any range derivable therein) as compared to a cell not exposed to the IL-6Rα binding protein. In some embodiments, a IL-6Rα scFv reduces the expression of any of the following cytokines: TNF-α, IL-6, IL-2, IL-4, and GM-CSF (or any combination thereof). In some instances, an IL-6Rα scFv reduces the expression of one or more of those cytokines by, by at least, or by at most 10%, 20%, 30%, 40%, or 50% (or any range derivable therein) as compared to a cell exposed to tocilizumab. In other embodiments, an IL-6Rα scFv reduces the expression of one or more cytokines greater than tocilizumab. Methods similarly may involve an IL-6Rα scFv that reduces the expression of one or more cytokines greater than tocilizumab. In certain embodiments, methods involve an IL-6Rα scFv that reduces the expression of TNF-α, IL-6, IL-2, IL-4, and/or GM-CSF greater than tocilizumab. In some embodiments, the IL-6 receptor alpha single chain variable fragment that reduces expression of one or more cytokines comprises a heavy chain variable region comprising CDR1 (SEQ ID NO:5), CDR2 (SEQ ID NO:6), and CDR3 (SEQ ID NO:7) attached by a heterologous linker to a light chain variable region comprising CDR4 (SEQ ID NO:8), CDR5 (SEQ ID NO:9), and CDR6 (SEQ ID NO:10). Other IL-6Rα scFvs discussed in other paragraphs can reduce the expression of a cytokine as described herein.

A "chimeric interleukin 6 receptor alpha (IL-6Rα) binding protein" refers to a protein that specifically binds to IL-6 receptor alpha and that contains at least two amino acid regions (each region is at least 10 contiguous amino acids), each region being from a different gene, and wherein the chimeric protein is not found in nature. In some embodiments, the chimeric IL-6Rα protein is a single polypeptide. A chimeric IL-6Rα binding protein does not refer to an IL-6Rα antibody that is found in nature. "Isolated" refers to the separation or purification of the protein from either other proteins or one or more other components of a cell.

Other aspects concern a cell or cells that express a chimeric IL-6Rα binding protein. The cells may express the chimeric IL-6Rα binding protein on its surface or they may express and secrete the chimeric IL-6Rα binding protein. In certain embodiments, T cells express the chimeric IL-6Rα binding protein. The T cells may be among other blood cells or they may be in a pool of enriched T cells. The T cells may be conventional T cells of naïve, central memory, effector memory, or effector phenotypes; or they may be regulatory T cells of natural or induced phenotypes. In some cases, the T cells express one or more of the following markers: CD4, CD8, CD25, CD27, CD28, CD45RA, CD45RO, CD57, CD62L, CD69, CD95, CD127, CCR7, IL-7Ra, or Foxp3. In some embodiments the T cell is a CD4+ T cell. In some embodiments, the T cell is a CD8+ T cell.

In some embodiments, there is a nucleic acid molecule encoding the chimeric IL-6Rα binding protein. Certain embodiments involve a nucleic acid molecule that also comprises a promoter controlling expression of the chimeric IL-6R binding protein. In some embodiments, the promoter is constitutive. In other embodiments, the promoter responds positively to at least one cytokine or is responsive to one or more transcription factors that are upregulated in expression or activity when cytokines are upregulated. Promoters may respond positively to one or more of the following cytokines: IL-6, TNF-α, IFN-γ, IL-1β, IL-2, IL-8, or IL-10. In other embodiments, a promoter responsive to a transcription factor that is increased when T cells are activated; NFAT-1 is such a transcription factor, as is NF-κB.

In further embodiments, there is an expression construct comprising the nucleic acid molecule encoding an IL-6Rα binding protein. Some embodiments concern an expression construct that is a viral vector while others involve an expression construct that is a plasmid.

Certain embodiments concern one or more cells that contain a nucleic acid construct encoding an IL-6Rα binding protein. In some embodiments, the cell is a T cell. In specific embodiments, the cells have been transfected or infected with the expression construct, which may or may not integrate into the genome of one or more host cells. In some cases, there is a T cell comprising a heterologous expression construct encoding an IL-6Rα scFv comprising a leader peptide, a heavy chain variable region comprising CDR1 (SEQ ID NO:5), CDR2 (SEQ ID NO:6), and CDR3 (SEQ ID NO:7) attached by a heterologous linker to a light chain variable region comprising CDR4 (SEQ ID NO:8), CDR5 (SEQ ID NO:9), and CDR6 (SEQ ID NO:10), wherein the heterologous linker comprises the amino acid sequence GSTSGSGKPGSGEGSTKG (SEQ ID NO:11). In some embodiments, the IL-6Rα binding protein is a single chain antibody fragment (scFv). In some embodiments, the expression construct comprises a cytokine-responsive promoter, meaning the promoter has increased expression when cytokines are increased. In some embodiments, cytokines are increased when T cells are activated. In some embodiments, cytokines are increased when T-cell activation triggers a systemic immune response. In some embodiments, cytokines are increased when tumor-cell lysis triggers a systemic immune response.

Other embodiments concerns methods of making or using the IL-6Rα binding proteins, nucleic acid molecules encoding such proteins, or cells expressing such proteins. In certain embodiments, there are methods for reducing the risk of cytokine release syndrome (CRS), methods for inhibiting IL-6Rα, methods for treating cancer, methods for treating an autoimmune disease, methods for reducing the toxicity of one or more cytokines, methods for reducing toxicity of T-cell activation, and methods for manufacturing an IL-6Rα therapeutic composition. Embodiments also concern use of a chimeric IL-6Rα binding protein for the treatment of the cytokine release syndrome, for the treatment of cancer, and/or for the treatment of an autoimmune disease.

In some embodiments, methods comprise administering to a patient at risk for cytokine release syndrome a composition comprising an isolated IL-6 receptor alpha (IL-6Rα) binding protein or cells comprising a heterologous nucleic acid molecule encoding the IL-6Rα binding protein. In some cases, the patient has cancer and/or an autoimmune disease. In some circumstances, the patient has or will receive adoptive T-cell therapy. In some instances, the patient is administered the composition after adoptive T-cell transfer. In some instances, the patient is administered the composition along with adoptive T-cell transfer. In some cases, the patient has or will receive lymphodepletion. The patient may receive or may have received adoptive T cell therapy within 1, 2, 3, 4, 5, 6, 7, 8, 9, 10, 11, 12, 13, 14, 15, 16, 17, 18, 19, 20, 21, 22, 23, or 24 hours or 1, 2, 3, 4, 5, 6, 7, 8, 9, 10, 11, 12, 13, 14, 15, 16, 17, 18, 19, 20, 21, 22, 23, or 24 days (or any range derivable within) of receiving a therapeutic composition involving an IL-6Rα binding protein. In other embodiments, the patient has an autoimmune disease.

In some embodiments, the patient is administered T cells comprising a heterologous nucleic acid molecule encoding an IL-6Rα binding protein. In further embodiments, the patient is administered T cells that are autologous.

In further embodiments, methods include also administering to the patient an antihistamine, a corticosteroid, a steroid, acetaminophen, furosemide, and/or intravenous fluids or any other treatment used for cytokine release syndrome or other toxicity or side effects associated with T-cell engaging therapies. In some cases, the patient has one or more symptoms of cytokine release syndrome.

In some embodiments, there are methods for reducing the toxicity of adoptive cell therapy in a cancer patient comprising administering to the patient a composition comprising an isolated IL-6 receptor alpha (IL-6Rα) binding protein or cells comprising a heterologous nucleic acid molecule encoding the IL-6Rα binding protein. Additional embodiments include methods for treating an autoimmune disease in a patient comprising administering to the patient a composition comprising a composition comprising an isolated IL-6 receptor alpha (IL-6Rα) binding protein or cells comprising a heterologous nucleic acid molecule encoding the IL-6Rα binding protein. Other embodiments concern methods for treating a cancer patient comprising administering to the patient a composition comprising an isolated IL-6 receptor alpha (IL-6Rα) binding protein or cells comprising a heterologous nucleic acid molecule encoding the IL-6Rα binding protein, wherein the patient has been or will be treated with immunotherapy. In some embodiments, the patient has been or will be treated with an anti-T cell antibody. Non-limiting examples of anti-T cell antibodies include anti-thymocyte globulin, Muromonab-CD3, TGN1412, anti-CD20, anti-CD19, rituximab, and tisagenlecleucel. In some embodiments, the immunotherapy is adoptive cell therapy. In some embodiments, the methods of the disclosure comprise administering to the patient a composition comprising cells comprising a heterologous nucleic acid molecule encoding the IL-6Rα binding protein and a tumor-targeting receptor. Other embodiments concern methods for reducing the toxicity of one or more cytokines comprising administering to a patient with an autoimmune disease or condition or a patient being treated with immunotherapy an effective amount of a composition comprising a single chain variable fragment comprising the isolated IL-6Rα binding protein comprises a heavy chain variable region comprising CDR1 (SEQ ID NO:5), CDR2 (SEQ ID NO:6), and CDR3 (SEQ ID NO:7) attached by a heterologous linker to a light chain variable region comprising CDR4 (SEQ ID NO:8), CDR5 (SEQ ID NO:9), and CDR6 (SEQ ID NO:10).

The polypeptides described herein may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of any of SEQ ID NOs: 1-11.

In one embodiment of the methods described herein, the subject is a human subject. The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is specifically contemplated that embodiments described herein may be excluded. It is further contemplated that, when a range is described, certain ranges may be excluded.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects. Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
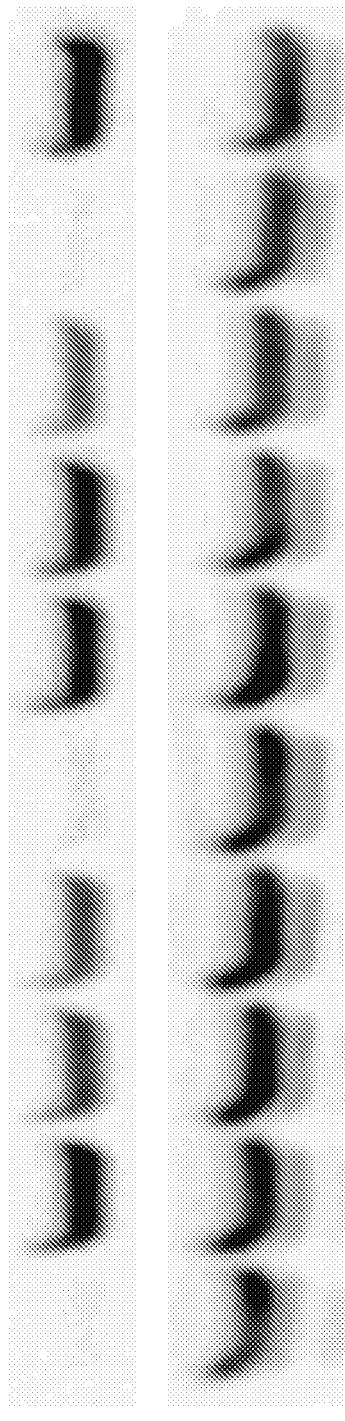
FIG. 1. Anti-IL-6Rα scFvs inhibit IL-6 signaling in HepG2 cells. HepG2 human hepatocarcinoma cells were seeded in a 12-well plate and incubated with indicated amounts of scFv for 3 hours. The indicated wells were subsequently treated with 4 ng/ml of IL-6 and incubated for another 30 minutes before cell harvest. The presence of phosphorylated STAT3 (pSTAT3), a major signaling molecule in the IL-6 signaling pathway, was probed by western blot, along with GAPDH (loading control).

Embodiments disclosed herein include polypeptides that bind to IL-6Rα, which modulates the inflammatory effects of IL-6. Further embodiments include cells that express IL-6Rα-binding polypeptides, as well as methods of using the cells and polypeptides in cancer therapy, autoimmune therapy, and anti-inflammatory therapy, among others. These and other non-limiting aspects of the present invention are discussed in further detail in the following sections.

I. DEFINITIONS

Embodiments disclosed herein may include chimeric antigen receptors (CARs), which may be expressed by T cells or other immune cell types. CARs are engineered receptors, which graft an arbitrary specificity onto an immune effector cell. Typically, these receptors are used to graft the specificity of a monoclonal antibody onto a T cell. The receptors are called chimeric because they are composed of parts from different sources.

The terms "protein," "polypeptide," and "peptide" are used interchangeably herein when referring to a gene product.

"Homology," "identity," or "similarity" refers to sequence similarity between two peptides or between two nucleic acid molecules. Identity can be determined by comparing a position in each sequence which may be aligned for purposes of comparison. When a position in the compared sequence is occupied by the same base or amino acid, then the molecules share sequence identity at that position. A degree of identity between sequences is a function of the number of matching or homologous positions shared by the sequences. An "unrelated" or "non-homologous" sequence shares less than 40% identity, or less than 25% identity, with one of the sequences of the current disclosure.

The terms "amino portion," "N-terminus," "amino terminus," and the like as used herein are used to refer to order of the regions of the polypeptide. Furthermore, when something is N-terminal to a region it is not necessarily at the terminus (or end) of the entire polypeptide, but just at the terminus of the region or domain. Similarly, the terms "carboxy portion," "C-terminus," "carboxy terminus," and the like as used herein is used to refer to order of the regions of the polypeptide, and when something is C-terminal to a region it is not necessarily at the terminus (or end) of the entire polypeptide, but just at the terminus of the region or domain.

The terms "subject," "individual," or "patient" are used interchangeably herein and refer to a vertebrate, for example a primate, a mammal or preferably a human. Mammals include, but are not limited to equines, canines, bovines, ovines, murines, rats, simians, humans, farm animals, sport animals and pets.

The term "xeno-free (XF)" or "animal component-free (ACF)" or "animal free," when used in relation to a medium, an extracellular matrix, or a culture condition, refers to a medium, an extracellular matrix, or a culture condition which is essentially free from heterogeneous animal-derived components. For culturing human cells, any proteins of a non-human animal, such as mouse, would be xeno components. In certain aspects, the xeno-free matrix may be essentially free of any non-human animal-derived components, therefore excluding mouse feeder cells or Matrigel™. Matrigel™ is a solubilized basement membrane preparation extracted from the Engelbreth-Holm-Swarm (EHS) mouse sarcoma, a tumor rich in extracellular matrix proteins to include laminin (a major component), collagen IV, heparin sulfate proteoglycans, and entactin/nidogen. In some embodiments, the compositions described herein or cells of the disclosure are cultured in and/or prepared in/with xeno-free or animal component-free or animal free medium.

Cells are "substantially free" of certain reagents or elements, such as serum, signaling inhibitors, animal components or feeder cells, exogenous genetic elements or vector elements, as used herein, when they have less than 10% of the element(s), and are "essentially free" of certain reagents or elements when they have less than 1% of the element(s). However, even more desirable are cell populations wherein less than 0.5% or less than 0.1% of the total cell population comprise exogenous genetic elements or vector elements.

A culture, matrix or medium are "essentially free" of certain reagents or elements, such as serum, signaling inhibitors, animal components or feeder cells, when the culture, matrix or medium respectively have a level of these reagents lower than a detectable level using conventional detection methods known to a person of ordinary skill in the art or these agents have not been extrinsically added to the culture, matrix or medium. The serum-free medium may be essentially free of serum.

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "cell" is herein used in its broadest sense in the art and refers to a living body which is a structural unit of tissue of a multicellular organism, is surrounded by a membrane structure which isolates it from the outside, has the capability of self-replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self-replication and pluripotency or multipotency. Typically, stem cells can regenerate an injured tissue. Stem cells herein may be, but are not limited to, embryonic stem (ES) cells, induced pluripotent stem cells or tissue stem cells (also called tissue-specific stem cell, or somatic stem cell).

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing certain factors, referred to as reprogramming factors.

"Pluripotency" refers to a stem cell that has the potential to differentiate into all cells constituting one or more tissues or organs, or particularly, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells or induced pluripotent cells.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

In some embodiments, the methods are useful for reducing the size and/or cell number of a solid tumor. In some embodiments, the method of the disclosure are useful for inhibiting the growth of tumors, such as solid tumors, in a subject.

The term "antigen" refers to any substance that causes an immune system to produce antibodies against it, or to which a T cell responds. In some embodiments, an antigen is a peptide that is 5-50 amino acids in length or is at least, at most, or exactly 5, 10, 15, 20, 25, 30, 35, 40, 45, 50, 55, 60, 65, 70, 75, 80, 85, 90, 95, 100, 125, 150, 175, 200, 250, or 300 amino acids, or any derivable range therein.

The term "antibody" includes monoclonal antibodies, polyclonal antibodies, dimers, multimers, multispecific antibodies and antibody fragments that may be human, mouse, humanized, chimeric, or derived from another species. A "monoclonal antibody" is an antibody obtained from a population of substantially homogeneous antibodies that is being directed against a specific antigenic site.

"Antibody or functional fragment thereof" means an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments of antibodies, including e.g., Fab', F(ab')$_2$, Fab, Fv, rIgG, and scFv fragments. The term scFv refers to a single chain Fv antibody in which the variable domains of the heavy chain and of the light chain of a traditional two chain antibody have been joined to form one chain.

The use of a single chain variable fragment (scFv) is of particular interest. scFvs are recombinant molecules in which the variable regions of light and heavy immunoglobulin chains encoding antigen-binding domains are engineered into a single polypeptide. Generally, the $V_H$ and $V_L$ sequences are joined by a linker sequence. See, for example, Ahmad (2012) Clinical and Developmental Immunology Article ID 980250, herein specifically incorporated by reference.

A "therapeutically effective amount" or "efficacious amount" refers to the amount of an agent, or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

II. POLYPEPTIDES

A. IL-6Rα-binding Polypeptides

Some embodiments disclosed herein include polypeptides that bind to IL-6Rα, including human IL-6Rα. The IL-6Rα-binding proteins can be administered in a pharmaceutical formulation or can be expressed from cells that are administered to a subject. In either case, the IL-6Rα-binding proteins affect immune processes involving IL-6. When an IL-6Rα-binding protein is expressed by a cell, such as a T cell, the IL-6Rα may modulate the immune function of the cell itself and/or other cells in the vicinity. In some embodiments, the IL-6Rα-binding protein reduces the secretion of pro-inflammatory cytokines by a cell that expresses the IL-6Rα binding protein or by other cells in the vicinity. Such pro-inflammatory cytokines may include TNF-α, IL-6, IL-2, IL-4, GM-CSF, and IL-10. The reduction in cytokine secretion by a cell expressing an IL-6Rα-binding protein can make the cell more effective and safe for use in therapies, such as adoptive T cell therapy. Cells that express an IL-6Rα-binding protein can self-modulate IL-6 signaling levels to prevent and/or ameliorate adverse inflammatory events such as cytokine release syndrome.

IL-6Rα-binding proteins can also be used in treating autoimmune conditions. In some embodiments, this may be accomplished by expressing an IL-6Rα-binding protein in a regulatory T cell, which will suppress undesirable inflammatory responses and ameliorate the severity of autoimmune attacks. This may also be accomplished by administering an IL-6Rα-binding protein itself to modulate signaling through IL-6Rα.

In some embodiments, the IL-6Rα-binding polypeptide is a single chain Fv (scFv), which comprise the $V_H$ and $V_L$ domains of an antibody, wherein these domains are present in a single polypeptide chain. In some embodiments, the antigen-binding domain further comprises a peptide linker between the $V_H$ and $V_L$ domains, which can enable the scFv to form the desired structure for antigen binding. Two different scFv constructs are used in the Examples section below: (1) the $V_L$-$V_H$ scFv and (2) the $V_H$-$V_L$ scFv. These two constructs differ only in the order of the sequences. The $V_L$-$V_H$ scFv configuration is N-terminus-$V_L$-linker-$V_H$-C-terminus, and the $V_H$-$V_L$ scFv configuration is N-terminus-$V_H$-linker-$V_L$-C-terminus, where $V_L$ refers to the light chain variable fragment and $V_H$ refers to the heavy chain variable fragment. The amino acid sequences for these scFv constructs are set forth in the table below:

| Single Chain Variable Fragment | Amino Acid Sequence (Single Letter Abbreviations) |
| --- | --- |
| anti-IL-6Rα $V_L$-$V_H$ scFv | METDTLLLWVLLLWVPGSTGDGGSDYKDDDDKGGSDI QMTQSPSSLSASVGDRVTITCRASQDISSYLNWYQQK PGKAPKLLIYYTSRLHSGVPSRFSGSGSGTDFTFTIS SLQPEDIATYYCQQGNTLPYTFGQGTKVEIKRTVAAP SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGECGSTSGSGKPG SGEGSTKGEVQLQESGPGLVRPSQTLSLTCTVSGYSI TSDHAWSWVRQPPGRGLEWIGYISYSGITTYNPSLKS RVTMLRDTSKNQFSLRLSSVTAADTAVYYCARSLART TAMDYWGQGSLVTVSSASTKGPSVFPLAPSSKSTSGG TAALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPELLGGPSVFLFPPKPKD TLMISRTPEVTCVVVDVSHEDPEVKFNWYVDGVEVHN AKTKPREEQYNSTYRVVSVLTVLHQDWLNGKEYKCKV SNKALPAPIEKTISKAKGQPREPQVYTLPPSRDELTK NQVSLTCLVKGFYPSDIAVEWESNGQPENNYKTTPPV LDSDGSFFLYSKLTVDKSRWQQGNVFSCSVMHEALHN HYTQKSLSLSPG (SEQ ID NO: 1) |
| anti-IL-6Rα $V_H$-$V_L$ scFv | METDTLLLWVLLLWVPGSTGDGGSDYKDDDDKGGSEV QLQESGPGLVRPSQTLSLTCTVSGYSITSDHAWSWVR QPPGRGLEWIGYISYSGITTYNPSLKSRVTMLRDTSK NQFSLRLSSVTAADTAVYYCARSLARTTAMDYWGQGS LVTVSSASTKGPSVFPLAPSSKSTSGGTAALGCLVKD YFPEPVTVSWNSGALTSGVHTFPAVLQSSGLYSLSSV VTVPSSSLGTQTYICNVNHKPSNTKVDKKVEPKSCDK THTCPPCPAPELLGGPSVFLFPPKPKDTLMISRTPEV TCVVVDVSHEDPEVFNWYVDGVEVHNAKTKPREEQYN STYRVVSVLTVLHQDWLNGKEYKCKVSNKALPAPIEK TISKAKGQPREPQVYTLPPSRDELTKNQVSLTCLVKG FYPSDIAVEWESNGQPENNYKTTPPVLDSDGSFFLYS KLTVDKSRWQQGNVFSCSVMHEALHNHYTQKSLSLSP GGSTSGSGKPGSGEGSTKGDIQMTQSPSSLSASVGDR VTITCRASQDISSYLNWYQQKPGKAPKLLIYYTSRLH SGVPSRFSGSGSGTFTFTISSLQPEDIATYYCQQGNT LPYTFGQGTKVEIKRTVAAPSVFIFPPSDEQLKSGTA SVVCLLNNFYPREAKVQWKVDNALQSGNSQESVTEQD SKDSTYSLSSTLTLSKADYEKHKVYACEVTHQGLSSP VTKSFNRGEC (SEQ ID NO: 2) |

The $V_H$ and $V_L$ sequences of the anti-IL-6Rα scFvs of SEQ ID NOs:1 and 2, along with the sequences for the CDRs within these sequences and the linker sequence between the $V_H$ and $V_L$ sequences in the scFvs are set forth in the following table:

| Sequence name | Amino Acid Sequence (Single Letter Abbreviations) |
| --- | --- |
| $V_H$ of the anti-IL-6Rα scFvs | EVQLQESGPGLVRPSQTLSLTCTVSGYSITSDHAWSWVR QPPGRGLEWIGYISYSGITTYNPSLKSRVTMLRDTSKNQ FSLRLSSVTAADTAVYYCARSLARTTAMDYWGQGSLVTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSCDKTHTCPPCPAP ELLGGPSVFLFPPKPKDTLMISRTPEVTCVVVDVSHEDP EVKFNWYVDGVEVHNAKTKPREEQYNSTYRVVSVLTVLH QDWLNGKEYKCKVSNKALPAPIEKTISKAKGQPREPQVY TLPPSRDELTKNQVSLTCLVKGFYPSDIAVEWESNGQPE NNYKTTPPVLDSDGSFFLYSKLTVDKSRWQQGNVFSCSV MHEALHNHYTQKSLSLSPG (SEQ ID NO: 3) |
| $V_L$ of the anti-IL-6Rα scFvs | DIQMTQSPSSLSASVGDRVTITCRASQDISSYLNWYQQK PGKAPKLLIYYTSRLHSGVPSRFSGSGSGTDFTFTISSL QPEDIATYYCQQGNTLPYTFGQGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC (SEQ ID NO: 4) |
| CDR1 ($V_H$) | SDHAWS (SEQ ID NO: 5) |
| CDR2 ($V_H$) | YISYSGITTYNPSLKS (SEQ ID NO: 6) |
| CDR3 ($V_H$) | SLARTTAMDY (SEQ ID NO: 7) |
| CDR4 ($V_L$) | RASQDISSYLN (SEQ ID NO: 8) |
| CDR5 ($V_L$) | YTSRLHS (SEQ ID NO: 9) |
| CDR6 ($V_L$) | QQGNTLPYT (SEQ ID NO: 10) |
| Linker | GSTSGSGKPGSGEGSTKG (SEQ ID NO: 11) |

The scFvs of SEQ ID NOs:1 and 2 are constructed from tocilizumab (WO 1992019759 A1, U.S. Pat. Nos. 5,670,373, 7,479,543, 8,580,264), and previously developed anti-IL-6Rα monoclonal antibody, by connecting the $V_H$ domain to the $V_L$ domain with the linker of SEQ ID NO: 11.

Besides scFvs, the IL-6Rα-binding protein can take a variety of forms that may incorporate one or more of the $V_H$ (SEQ ID NO:3), $V_L$, or CDR (SEQ ID NOs:5-11) sequences disclosed herein or derivatives or variations thereof. For example, the binding protein can be an antibody-like molecule that has an antigen binding region, including antibody fragments such as Fab', Fab, F(ab')$_2$, F(ab)$_2$, (scFv)$_2$, single domain antibodies (DABs), Fv, and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region. Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate IL-6Rα-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as target binding molecules. Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibiters of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. In order to describe antibodies of some embodiments, the strength with which an antibody molecule binds an epitope, known as affinity, can be measured. The affinity of an antibody may be determined by measuring an association constant ($K_a$) or dissociation constant ($K_d$). Antibodies deemed useful in certain embodiments may have an association constant of about, at least about, or at most about $10^6$, $10^7$, $10^8$, $10^9$ or $10^{10}$ M or any range derivable therein. Similarly, in some embodiments antibodies may have a dissoaciation constant of about, at least about or at most about $10^{-6}$, $10^{-7}$, $10^{-8}$ $10^{-9}$ or $10^{-10}$ M or any range derivable therein.

In certain embodiments, a polypeptide that specifically binds to IL-6Rα is able to neutralize IL-6Rα and/or prevent binding of IL-6 to IL-6Rα or prevent signaling through IL-6Rα.

B. Modifications to IL-6Rα-Binding Polypeptides

1. Signal Peptides

Any IL-6Rα-binding protein can be tagged with the leader (i.e. signal) peptide. A "signal peptide" refers to a peptide sequence that directs the transport and localization of the protein within a cell, e.g. to a certain cell organelle (such as the endoplasmic reticulum) and/or the cell surface. A signal peptide directs the nascent protein into the endoplasmic reticulum. Generally, the signal peptide natively attached to the amino-terminal most component is used (e.g. in a scFv with orientation light chain—linker—heavy chain, the native signal of the light-chain is used). In some embodiments the signal peptide from the murine kappa light chain is used so that the proteins are secreted from the expressing cells. This also allows the expressed protein to be directly collected from the media in which the producer cells are cultured. Other leader/signal peptides known to those in the art can also be used.

In some embodiments, the signal peptide is cleaved after passage of the endoplasmic reticulum (ER), i.e., is a cleavable signal peptide. In some embodiments, a restriction site is at the carboxy end of the signal peptide to facilitate cleavage.

2. Markers and Epitope Tags

The IL-6Rα-binding proteins can also be tagged with markers such as the DYKDDDDK (SEQ ID NO:69) (FLAG) epitope, HA tag, or cMyc tag or other epitope tags, markers, and affinity tags known in the art. This can facilitate isolation, purification, localization, and targeted binding of the IL-6Rα-binding protein. In some embodiments, the marker is flanked by GGS linkers.

3. Linkers

In some embodiments, the polypeptides of the disclosure include peptide linkers (sometimes referred to as a linker). A peptide linker may be separating any of the peptide domain/regions described herein. As an example, a linker may be between the signal peptide and the antigen binding domain, between a $V_H$ and $V_L$ of an antigen binding domain, between an antigen binding domain and a peptide spacer, between a peptide spacer and a transmembrane domain. A peptide linker may have any of a variety of amino acid sequences. Domains and regions can be joined by a peptide linker that is generally of a flexible nature, although other chemical linkages are not excluded. A linker can be a peptide of between about 6 and about 40 amino acids in length, or between about 6 and about 25 amino acids in length. These linkers can be produced by using synthetic, linker-encoding oligonucleotides to couple the proteins.

Peptide linkers with a degree of flexibility can be used. The peptide linkers may have virtually any amino acid sequence, bearing in mind that suitable peptide linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ and $(GGGS)_n$, where n is an integer of at least one, glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains. Exemplary spacers can comprise amino acid sequences including, but not limited to, GGSG, GGSGG, GSGSG, GSGGG, GGGSG, GSSSG, and the like.

4. Modifications to Antigen-Binding Domains

The variable regions of antigen-binding domains of IL-6Rα-binding proteins of the disclosure can be modified by mutating amino acid residues within $V_H$ and/or $V_L$ CDR regions to improve one or more binding properties (e.g., affinity) of the protein. The term "CDR" refers to a complementarity-determining region that is based on a part of the variable chains in immunoglobulins (antibodies) and T-cell receptors, generated by B cells and T cells respectively, where these molecules bind to their specific antigen. Since most sequence variation associated with immunoglobulins and T-cell receptors are found in the CDRs, these regions are sometimes referred to as hypervariable regions. Mutations may be introduced by site-directed mutagenesis or PCR-mediated mutagenesis and the effect on antibody binding, or other functional property of interest, can be evaluated in appropriate in vitro or in vivo assays. Preferably conservative modifications are introduced and typically no more than one, two, three, four or five residues within a CDR region are altered. The mutations may be amino acid substitutions, additions or deletions.

Framework modifications can be made to IL-6Rα-binding proteins to decrease immunogenicity, for example, by "backmutating" one or more framework residues to a corresponding germline sequence.

It is also contemplated that the antigen binding domain may be multi-specific or multivalent by multimerizing the antigen binding domain with $V_H$ and $V_L$ region pairs that bind either the same antigen (multi-valent) or a different antigen (multi-specific).

As used herein, the term "affinity" refers to the equilibrium constant for the reversible binding of two agents and is expressed as a dissociation constant ($K_d$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more (or any derivable range therein), than the affinity of an antibody for unrelated amino acid sequences. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges.

5. Chemical Modifications

Additionally, the polypeptides of the disclosure may be chemically modified. Glycosylation of the polypeptides can be altered, for example, by modifying one or more sites of glycosylation within the polypeptide sequence to increase the affinity of the polypeptide for antigen (U.S. Pat. Nos. 5,714,350 and 6,350,861).

The polypeptides of the invention can be pegylated to increase biological half-life by reacting the polypeptide with polyethylene glycol (PEG) or a reactive ester or aldehyde derivative of PEG, under conditions in which one or more PEG groups become attached to the polypeptide. Polypeptide pegylation may be carried out by an acylation reaction or an alkylation reaction with a reactive PEG molecule (or an analogous reactive watersoluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. Methods for pegylating proteins are known in the art and can be applied to the polypeptides of the invention (EP 0 154 316 and EP 0 401 384).

Additionally, polypeptides may be chemically modified by conjugating or fusing the polypeptide to serum protein, such as human serum albumin, to increase half-life of the resulting molecule. Such approach is for example described in EP 0322094 and EP 0 486 525.

The polypeptides of the disclosure may be conjugated to a diagnostic or therapeutic agent and used diagnostically, for example, to monitor the development or progression of a disease and determine the efficacy of a given treatment regimen. The polypeptides may also be conjugated to a therapeutic agent to provide a therapy in combination with the therapeutic effect of the polypeptide. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the polypeptide, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include .sup.125I, .sup.131I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Ithenium-188, Rhenium-189, Lead-212, Radium-223, Actinium-225, Iron-59, Selenium-75, Arsenic-77, Strontium-89, Molybdenum-99, Rhodium-1105, Palladium-$10^9$, Praseodymium-143, Promethium-149, Erbium-169, Iridium-194, Gold-198, Gold-199, and Lead-211. Chelating agents may be attached through amities (Meares et al., 1984 Anal. Biochem. 142: 68-78); sulfhydral groups (Koyama 1994 Chem. Abstr. 120: 217262t) of amino acid residues and carbohydrate groups (Rodwell et al. 1986 PNAS USA 83: 2632-2636; Quadri et al. 1993 Nucl. Med. Biol. 20: 559-570).

The polypeptides may also be conjugated to a therapeutic agent to provide a therapy in combination with the therapeutic effect of the polypeptide.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stern-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependant on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

C. Expression of IL-6Rα-Binding Proteins

IL-6Rα-binding proteins can be expressed in a variety of cell types. An expression construct encoding an IL-6Rα-binding protein can be transfected into cells according to a variety of methods known in the art. In some embodiments, the IL-6Rα-binding protein expression construct can be under control of a constitutive promoter. In some embodiments, it can be under control of a regulatable promoter that drives expression only under certain conditions. This can provide for expression of a IL-6Rα-binding protein only when necessary to respond to a potentially harmful situation or a situation in which it is desirable to reduce signaling through IL-6Rα, such as, for example, when there are increased levels of cytokines present. To accomplish this, the IL-6Rα-binding protein expression construct may be placed under control of a promoter that is responsive to cytokines such as IL-6, TNF-α, IFN-γ, IL-1β, IL-2, IL-8, and IL-10. The IL-6Rα-binding protein expression construct can also be placed under control of a promoter that is linked to T-cell activation, such as one that is controlled by NFAT-1 or NF-κB, both of which are transcription factors that can be activated upon T-cell activation. Control of IL-6Rα-binding protein expression allows T cells, such as tumor-targeting T cells, to sense their surroundings and perform real-time modulation of cytokine signaling, both in the T cells themselves and in surrounding endogenous immune cells.

III. NUCLEIC ACIDS

In certain embodiments, there are recombinant polynucleotides encoding the proteins, polypeptides, or peptides described herein. Polynucleotide sequences contemplated include those encoding IL-6Rα-binding proteins and CARs.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein.

In particular embodiments, there are isolated nucleic acid segments and recombinant vectors incorporating nucleic acid sequences that encode a polypeptide (e.g., an antibody or fragment thereof) that binds to IL-6Rα. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody that binds IL-6Rα.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

D. Methods of Gene Transfer

Suitable methods for nucleic acid delivery to effect expression of compositions are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Through the application of techniques such as these, organelle(s), cell(s), tissue(s) or organism(s) may be stably or transiently transformed. Other methods include viral transduction, such as gene transfer by lentiviral or retroviral transduction.

E. IL-6Rα-Binding Protein Expression Construct

In some embodiments, an IL-6Rα-binding protein is encoded by an expression construct that has the following structure: murine 5'-IgG kappa leader sequence-FLAG tag-$V_L$-scFv linker-$V_H$-3'. The following DNA sequence encodes such a construct (underlined sequences are the murine IgG kappa leader and the scFv linker sequences):

```
                                            (SEQ ID NO: 89)
ATGGAGACAGACACACTCCTGCTATGGGTGCTGCTGCTCTGGGTTCCAGG

TTCCACAGGTGACGGAGGCAGCGACTATAAAGATGACGATGACAAAGGAG

GTAGCGATATACAAATGACTCAATCACCTTCCTCACTTTCCGCCAGCGTG

GGTGATCGAGTGACCATCACATGCCGCGCTTCACAGGACATCTCCTCTTA

CCTGAACTGGTACCAGCAGAAACCCGGGAAAGCCCCAAAGCTGTTGATCT

ACTATACATCAAGACTGCACTCTGGCGTCCCCTCTAGGTTCAGTGGATCT

GGCTCAGGTACTGACTTCACGTTCACTATTTCCAGCCTGCAGCCGGAAGA

TATTGCTACCTACTATTGTCAGCAGGGAAATACCCTCCCATATACCTTTG

GGCAGGGGACAAAGGTGGAAATCAAGCGGACGGTAGCTGCTCCGTCAGTG

TTCATCTTTCCACCTTCAGATGAGCAGCTGAAGTCCGGAACCGCCAGTGT

GGTGTGCCTCCTGAATAACTTTTATCCACGAGAAGCCAAGGTGCAGTGGA

AAGTGGATAACGCTTTGCAAAGTGGCAATTCTCAAGAGAGCGTAACTGAG

CAAGATAGCAAGGACAGTACTTACAGCTTGAGCAGCACGCTGACCCTGAG

CAAGGCCGATTACGAGAAACACAAGGTGTATGCCTGCGAGGTGACCCACC

AGGGCCTTAGCTCACCTGTGACCAAGTCCTTCAACAGAGGCGAGTGTGGC

AGCACCTCCGGCAGCGGCAAGCCTGGCAGCGGCGAGGGCAGCACCAAGGG

CGAGGTCCAACTGCAGGAAAGCGGTCCAGGCTTGGTGAGACCATCCCAGA

CCCTGAGCCTCACCTGTACCGTGTCCGGGTACAGTATCACCTCCGACCAT

GCATGGTCCTGGGTGCGCCAGCCTCCCGGAAGAGGTCTGGAATGGATCGG

GTATATCTCCTACTCAGGAATCACCACCTACAATCCCTCCCTTAAGTCAA

GGGTGACTATGCTCCGCGATACATCCAAAAATCAGTTCTCCCTTCGGTTG

TCAAGTGTTACAGCCGCCGACACCGCAGTCTACTACTGTGCAAGGAGCCT

CGCCAGGACGACTGCAATGGATTATTGGGGCCAGGGCTCCCTGGTGACTG

TCAGCAGCGCCTCAACAAAGGGCCCATCTGTTTTTCCACTTGCCCCAAGC

TCTAAAAGTACCTCAGGAGGAACCGCTGCCCTCGGGTGCCTCGTCAAAGA
```

-continued
```
TTACTTTCCAGAACCCGTTACAGTGTCCTGGAACTCCGGAGCTCTTACCT

CCGGGGTGCATACATTCCCGGCCGTTCTTCAAAGCTCTGGACTCTACTCC

CTGAGCTCCGTTGTGACAGTTCCTAGCAGCAGCCTCGGCACCCAGACATA

CATCTGCAACGTAAACCACAAGCCTTCAAACACTAAAGTGGACAAAAAAG

TGGAACCGAAGTCCTGTGACAAAACTCACACATGCCCTCCGTGCCCTGCC

CCAGAGCTGCTGGGCGGGCCATCCGTATTTCTCTTCCCTCCAAAGCCAAA

GGATACCCTCATGATCAGCCGGACGCCCGAAGTGACCTGCGTCGTAGTGG

ATGTGAGTCACGAGGACCCAGAGGTAAAGTTCAACTGGTACGTAGACGGC

GTGGAGGTCCATAATGCGAAGACGAAACCCAGAGAGGAGCAGTACAACTC

AACTTACAGAGTGGTCAGCGTGCTCACTGTCCTCCACCAGGACTGGTTGA

ACGGCAAAGAATATAAGTGTAAGGTGAGCAATAAGGCCCTCCCCGCCCCT

ATCGAGAAACTATTTCCAAGGCTAAAGGCCAGCCTCGAGAACCTCAGGT

TTACACACTGCCTCCTAGCCGCGATGAACTGACAAAAAATCAGGTGAGTC

TCACCTGCCTCGTTAAAGGTTTCTACCCTTCAGATATCGCAGTCGAGTGG

GAGAGCAACGGGCAGCCGGAAAATAACTATAAGACCACCCCCCCAGTCCT

TGACAGTGACGGCTCTTTCTTCCTGTACTCCAAACTGACCGTGGACAAAT

CTAGGTGGCAGCAAGGAAATGTTTTTAGTTGTTCTGTAATGCACGAGGCT

CTGCATAATCATTATACCCAAAAGTCTTTGTCCCTCTCCCCGGC
```

IV. CELLS

A. Cell Types

Certain embodiments relate to cells comprising polypeptides or nucleic acids of the disclosure. In some embodiments the cell is an immune cell or a T cell. "T cell" includes all types of immune cells expressing CD3 including T-helper cells ($CD4^+$ cells), cytotoxic T-cells ($CD8^+$ cells), T-regulatory cells ($T_{reg}$), suppressor T cells, and gamma-delta T cells. A "cytotoxic cell" includes $CD8^+$ T cells, natural-killer (NK) cells, and neutrophils, which cells are capable of mediating cytotoxicity responses. In some embodiments, the cell is a progenitor cell or stem cell. In some embodiments, the progenitor or stem cell is in vitro differentiated into an immune cell. In some embodiments, the cell is ex vivo. The term immune cells includes cells of the immune system that are involved in defending the body against both infectious disease and foreign materials. Immune cells may include, for example, neutrophils, eosinophils, basophils, natural killer cells, lymphocytes such as B cells and T cells, and monocytes.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), human embryonic kidney (HEK) 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RATI cells, mouse L cells (ATCC No. CCLl.3), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell or progenitor cell obtained from an individual.

B. Adoptive Cell Therapy

In some embodiments, cells disclosed herein are used in adoptive cell therapy or adoptive cell transfer, which involves administration of therapeutic cells to subjects. This therapy can involve administration of tumor-infiltrating lymphocytes, cytotoxic T lymphotytes (CTLs), helper T (Th) cells, and Treg cells, and other immune cells and other types of cells. The therapeutic cells may originate from a patient or from a donor. In some embodiments, cells are extracted from a patient, genetically modified and cultured in vitro and returned to the same patient.

Cells disclosed herein can be administered to a subject to treat, for example, cancer, autoimmune diseases, infections, and inflammatory disorders. In some embodiments, expression of IL-6Rα binding proteins by cells used in adoptive T cell therapy can reduce or eliminate side effects that may occur as a result of adoptive T cell therapy, such as cytokine release syndrome and other inflammatory or autoimmune conditions that involve IL-6 signaling through IL-6Rα. In addition, administration of IL-6Rα-binding proteins in conjunction with therapeutic T cells can eliminate, reduce, or mitigate the side effects of adoptive T cell therapy.

1. Chimeric Antigen Receptors
a. Use in Adoptive Cell Therapies

In some embodiments, therapeutic cells used in adoptive cell therapies express chimeric antigen receptors (CARs). CARs are fusion proteins that are commonly composed of an extracellular antigen-binding domain (which may be an scFv), an extracellular spacer, a transmembrane domain, costimulatory signaling regions (the number of which varies depending on the specific CAR design), and a CD3-zeta signaling domain/endodomain. Immune cells, including T cells and natural killer (NK) cells, can be engineered to express CARs by a variety of methods known in the art, including viral transduction, DNA nucleofection, and RNA nucleofection. CAR binding to the antigen target can activate human T cells expressing the CAR, which may result in killing of the cell bearing the antigen or some other immunological response.

In some embodiments, the cells comprise a cancer-specific CAR. The term "cancer-specific" in the context of CARs refers to CARs that have an antigen binding specificity for a cancer-specific molecule, such as a cancer-specific antigen. In some embodiments, the cancer specific CAR is in a cell with a CAR specific for another target, such as a TGF-β CAR. In some embodiments, the cancer-specific CAR and another CAR are on separate polypeptides. In some embodiments, the CAR is a bi-specific CAR that has antigen binding for a cancer-specific molecule and for another antigen, such as TGF-β. For example, a bi-specific CAR may have a signaling peptide, a cancer molecule-specific scFv, optionally a peptide linker/spacer, followed by an scFv that binds another antigen, followed by a spacer, a transmembrane domain, and a costimulatory domain. In some embodiments, the bi-specific CAR comprises one or more additional peptide segments described herein.

In some embodiments, CARs of the disclosure may comprise a CD20 scFv. An exemplary CD20 scFv comprises the following:

```
                                                  (SEQ ID NO: 12)
DIVLTQSPAILSASPGEKVTMTCRASSSVNYMDWYQKKPGSSPKPWIYAT

SNLASGVPARFSGSGSGTSYSLTISRVEAEDAATYYCQQWSFNPPTFGGG

TKLEIKGSTSGGGSGGGSGGGGSSEVQLQQSGAELVKPGASVKMSCKASG

YTFTSYNMHVWKQTPGQGLEWIGAIYPGNGDTSYNQKFKGKATLTADKSS

STAYMQLSSLTSEDSADYYCARSNYYGSSYWFFDVWGAGTTVTVSS.
```

In some embodiments, CARs of the disclosure may comprise a CD19 scFv. An exemplary CD19 scFv comprises the following:

```
                                                  (SEQ ID NO: 13)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGSTSGSGKPGSGEGSTKGEVKLQESGPGLVAPSQSLSVTCTVS

GVSLPDYGVSWIRQPPRKGLEWLGVIWGSETTYYNSALKSRLTIIKDNSK

SQVFLKMNSLQTDDTAIYYCAKHYYYGGSYAMD YWGQGTSVTVSS.
```

In some embodiments, as anti-CD19 CAR is encoded by a DNA construct with the following structure: GM-CSF signal peptide-HA tag-CD19 scFv-IgG4 hinge-CD28 tm-4-1BB co-stimulatory domain-CD3 zeta. This construct has the following sequence:

```
                                                  (SEQ ID NO: 88)
ATGCTGCTGCTGGTGACCAGCCTGCTGCTGTGCGAGCTGCCCCACCCCGC

CTTTCTGCTGATCCCCGGCGGAAGTTACCCATATGACGTTCCCGACTACG

CTGGCGACATCCAGATGACCCAGACCACCTCCAGCCTGAGCGCCAGCCTG

GGCGACCGGGTGACCATCAGCTGCCGGGCCAGCCAGGACATCAGCAAGTA

CCTGAACTGGTATCAGCAGAAGCCCGACGGCACCGTCAAGCTGCTGATCT

ACCACACCAGCCGGCTGCACAGCGGCGTGCCCAGCCGGTTTAGCGGCAGC

GGCTCCGGCACCGACTACAGCCTGACCATCTCCAACCTGGAACAGGAAGA

TATCGCCACCTACTTTTGCCAGCAGGGCAACACACTGCCCTACACCTTTG

GCGGCGGAACAAAGCTGGAAATCACCGGCAGCACCTCCGGCAGCGGCAAG

CCTGGCAGCGGCGAGGGCAGCACCAAGGGCGAGGTGAAGCTGCAGGAAAG

CGGCCCTGGCCTGGTGGCCCCCAGCCAGAGCCTGAGCGTGACCTGCACCG

TGAGCGGCGTGAGCCTGCCCGACTACGGCGTGAGCTGGATCCGGCAGCCC

CCCAGGAAGGGCCTGGAATGGCTGGGCGTGATCTGGGGCAGCGAGACCAC

CTACTACAACAGCGCCCTGAAGAGCCGGCTGACCATCATCAAGGACAACA

GCAAGAGCCAGGTGTTCCTGAAGATGAACAGCCTGCAGACCGACGACACC

GCCATCTACTACTGCGCCAAGCACTACTACTACGGCGGCAGCTACGCCAT

GGACTACTGGGGCCAGGGCACCAGCGTGACCGTGAGCAGCGAATCTAAGT

ACGGACCGCCCTGCCCCCCTTGCCCTATGTTCTGGGTGCTGGTGGTGGTC

GGAGGCGTGCTGGCCTGCTACAGCCTGCTGGTCACCGTGGCCTTCATCAT

CTTTTGGGTGAAACGGGGCAGAAAGAAACTCCTGTATATATTCAAACAAC

CATTTATGAGACCAGTACAAACTACTCAAGAGGAAGATGGCTGTAGCTGC

CGATTTCCAGAAGAAGAAGAAGGAGGATGTGAACTGCGGGTGAAGTTCAG
```

```
-continued
CAGAAGCGCCGACGCCCCTGCCTACCAGCAGGGCCAGAATCAGCTGTACA

ACGAGCTGAACCTGGGCAGAAGGGAAGAGTACGACGTCCTGGATAAGCGG

AGAGGCCGGGACCCTGAGATGGGCGGCAAGCCTCGGCGGAAGAACCCCCA

GGAAGGCCTGTATAACGAACTGCAGAAAGACAAGATGGCCGAGGCCTACA

GCGAGATCGGCATGAAGGGCGAGCGGAGGCGGGGCAAGGGCCACGACGGC

CTGTATCAGGGCCTGTCCACCGCCACCAAGGATACCTACGACGCCCTGCA

CATGCAGGCCCTGCCCCCAAGG.
```

Other cancer-specific molecules (in addition to CD19 and CD20) that can be targeted by CARs can include CAIX, CD33, CD44v7/8, CEA, EGP-2, EGP-40, erb-B2, erb-B3, erb-B4, FBP, fetal acetycholine receptor, GD2, GD3, Her2/neu, IL-13R-a2, KDR, k-light chain, LeY, L1 cell adhesion molecule, MAGE-A1, mesothelin, MUC1, NKG2D ligands, oncofetal antigen (h5T4), PSCA, PSMA, TAA targeted by mAb IgE, TAG-72, and VEGF-R2. In some embodiments, the cancer-specific molecule comprises Her2.

b. Signal Peptides

In some embodimetns, CARs include a signal peptide directs the transport and localization of the protein within a cell, e.g. to a certain cell organelle (such as the endoplasmic reticulum) and/or the cell surface. A signal peptide directs the nascent protein into the endoplasmic reticulum. This is essential if the receptor is to be glycosylated and anchored in the cell membrane. Generally, the signal peptide natively attached to the amino-terminal most component is used (e.g. in a scFv with orientation light chain—linker—heavy chain, the native signal of the light-chain is used). In some embodiments the signal peptide has the sequence METDTLLL-WVLLLWVPGSTG (SEQ ID NO:14), MLLVTSLLLCEL-PHPAFLLIPDT (SEQ ID NO:15), or MGTSLLCWMALCLLGADHADG (SEQ ID NO:16). In some embodiments, the signal peptide is cleaved after passage of the endoplasmic reticulum (ER), i.e. is a cleavable signal peptide. In some embodiments, a restriction site is at the carboxy end of the signal peptide to facilitate cleavage.

c. Antigen-binding Domain

The antigen-binding domain of a CAR is an antigen-binding protein, such as a single-chain variable fragment (scFv) based on antibodies against the target antigen. Framework modifications can be made to the antigen-binding domain to decrease immunogenicity, for example, by "back-mutating" one or more framework residues to the corresponding germline sequence. It is also contemplated that the antigen binding domain may be multi-specific or multivalent by multimerizing the antigen binding domain with $V_H$ and $V_L$ region pairs that bind either the same antigen (multivalent) or a different antigen (multi-specific).

d. Peptide Spacer

A spacer region links the antigen-binding domain to the transmembrane domain of a CAR. It should be flexible enough to allow the antigen-binding domain to orient in different directions to facilitate antigen recognition. The simplest form is the hinge region from IgG. Alternatives include the $CH_2CH_3$ region of immunoglobulin and portions of CD3. In some embodiments, the $CH_2CH_3$ region may have L235E/N297Q or L235D/N297Q modifications, or at least 75%, at least 80%, at least 85%, at least 90%, at least 95%, at least 98%, or 100% amino acid sequence identity of the $CH_2CH_3$ region. For most scFv-based constructs, the IgG hinge suffices. However the best spacer often has to be determined empirically. In some embodiments, the spacer is from IgG4.

As used herein, the term "hinge" refers to a flexible polypeptide connector region (also referred to herein as "hinge region" or "spacer") providing structural flexibility and spacing to flanking polypeptide regions and can consist of natural or synthetic polypeptides. A "hinge" derived from an immunoglobulin (e.g., IgG1) is generally defined as stretching from Glu216 to Pro230 of human IgG1 (Burton (1985) Molec. Immunol., 22: 161-206). Hinge regions of other IgG isotypes may be aligned with the IgG1 sequence by placing the first and last cysteine residues forming inter-heavy chain disulfide (S—S) bonds in the same positions. The hinge region may be of natural occurrence or non-natural occurrence, including but not limited to an altered hinge region as described in U.S. Pat. No. 5,677,425. The hinge region can include complete hinge region derived from an antibody of a different class or subclass from that of the $CH_1$ domain. The term "hinge" can also include regions derived from CD8 and other receptors that provide a similar function in providing flexibility and spacing to flanking regions.

The peptide spacer can have a length of at least, at most, or exactly 4, 5, 6, 7, 8, 9, 10, 15, 16, 17, 18, 19, 20, 20, 25, 30, 35, 40, 45, 50, 75, 100, 110, 120, 130, 140, 150, 160, 170, 180, 190, 200, 201, 202, 203, 204, 205, 206, 207, 208, 209, 210, 211, 212, 213, 214, 215, 216, 217, 218, 219, 220, 225, 226, 227, 228, 229, 230, 231, 232, 233, 234, 235, 236, 237, 238, 239, 240, 241, 242, 243, 244, 245, 246, 247, 248, 249, 250, 260, 270, 280, 290, 300, 325, 350, or 400 amino acids (or any derivable range therein). In some embodiments, the peptide spacer consists of or comprises a hinge region from an immunoglobulin. Immunoglobulin hinge region amino acid sequences are known in the art; see, e.g., Tan et al. (1990) Proc. Natl. Acad. Sci. USA 87: 162; and Huck et al. (1986) Nucl. Acids Res.

The length of a peptide spacer may have effects on the response to the target antigen and/or expansion properties. In some embodiments, a shorter spacer such as less than 50, 45, 40, 30, 35, 30, 25, 20, 15, or 10 amino acids may have the advantage of a decrease in the concentration of target antigen required for an effective activation response. In some embodiments, a longer spacer, such as one that is at least 50, 60, 70, 80, 90, 100, 110, 120, 130, 140, 150, 200, 201, 202, 203, 204, 205, 206, 207, 208, 209, 210, 211, 212, 213, 214, 215, 216, 217, 218, 219, 220, 225, 226, 227, 228, 229, 230, 231, 232, 233, 234, 235, 236, 237, 238, 239, 240, 241, 242, 243, 244, 245, 246, 247, 248, 249, 250, 260, 270, 280, or 290 amino acids may have the advantage of increased expansion in vivo or in vitro.

As non-limiting examples, an immunoglobulin hinge region can include one of the following amino acid sequences: DKTHT (SEQ ID NO:17); CPPC (SEQ ID NO:18); CPEPKSCDTPPPCPR (SEQ ID NO:19); ELKTPLGDTTHT (SEQ ID NO:20); KSCDKTHTCP (SEQ ID NO:21); KCCVDCP (SEQ ID NO:22); KYGPPCP (SEQ ID NO:23); EPKSCDKTHTCPPCP (SEQ ID NO:24) (human IgG1 hinge); ERKCCVECPPCP (SEQ ID NO:25) (human IgG2 hinge); ELKTPLGDTTHTCPRCP (SEQ ID NO:26) (human IgG3 hinge); SPNMVPHAHHAQ (SEQ ID NO:27); ESKYGPPCPPCP (SEQ ID NO:28) or ESKYGPPCPSCP (SEQ ID NO:29) (human IgG4 hinge-based) and the like.

The hinge region can comprise an amino acid sequence of a human IgG1, IgG2, IgG3, or IgG4, hinge region. The hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:30).

The hinge region can comprise an amino acid sequence derived from human CD8; e.g., the hinge region can comprise the amino acid sequence: TTTPAPRPPTPAPTIASQPLSLRPEACRPAAGGAVHTRGLDFACD (SEQ ID NO:31), or a variant thereof.

e. Transmembrane Domain

The transmembrane domain of the CAR is a hydrophobic alpha helix that spans the membrane. Generally, the transmembrane domain from the most membrane proximal component of the endodomain is used. Different transmembrane domains result in different receptor stability.

The transmembrane domain is interposed between the peptide spacer and the endodomain. In some embodiments, the transmembrane domain is interposed between the peptide spacer and a co-stimulatory region. In some embodiments, a linker is between the transmembrane domain and a co-stimulatory region or endodomain.

Any transmembrane domain that provides for insertion of a polypeptide into the cell membrane of a eukaryotic (e.g., mammalian) cell is suitable for use. As one non-limiting example, the transmembrane sequence IYIWAPLAGTCGVLLLSLVITLYC (SEQ ID NO:32) can be used. In some embodiments, the transmembrane domain is CD8 beta derived: LGLLVAGVLVLLVSLGVAIHLCC (SEQ ID NO:33); CD4 derived: ALIVLGGVAGLLLFIGLGIFFCVRC (SEQ ID NO:34); CD3 zeta derived: LCYLLDGILFIYGVILTALFLRV (SEQ ID NO:35); CD28 derived: WVLVVVGGVLACYSLLVTVAFIIFWV (SEQ ID NO:36); CD134 (OX40) derived: VAAILGLGLVLGLLGPLAILLALYLL (SEQ ID NO:37); or CD7 derived: ALPAALAVISFLLGLGLGVACVLA (SEQ ID NO:38).

f. Endodomain

After antigen recognition, receptors cluster and a signal is transmitted to the cell through the endodomain and/or co-stimulatory domain. In some embodiments, the co-stimulatory domains described herein are part of the endodomain. The most commonly used endodomain component is CD3-zeta, which contains 3 ITAMs. This transmits an activation signal to the T cell after antigen is bound. CD3-zeta may not provide a fully competent activation signal and additional co-stimulatory signaling is needed. For example, chimeric CD28 and OX40 can be used with CD3-Zeta to transmit a proliferative/survival signal, or all three can be used together.

Further endodomains suitable for use in CARs include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation by way of binding of the antigen to the antigen binding domain. In some embodiments, the endodomain includes at least one (e.g., one, two, three, four, five, six, etc.) ITAM motif as described herein. In some embodiments, the endodomain includes DAP10/CD28 type signaling chains.

Endodomains suitable for use in CARs include immunoreceptor tyrosine-based activation motif (ITAM)-containing intracellular signaling polypeptides. An ITAM motif is $YX_1X_2(L/I)$, where $X_1$ and $X_2$ are independently any amino acid (SEQ ID NO:39). In some cases, the endodomain comprises 1, 2, 3, 4, or 5 ITAM motifs. In some cases, an ITAM motif is repeated twice in an endodomain, where the first and second instances of the ITAM motif are separated from one another by 6 to 8 amino acids, e.g., (YX$_1$X$_2$(L/I))(X$_3$)$_n$(YX$_1$X$_2$(L/I)), where n is an integer from 6 to 8, and each of the 6-8 X$_3$ can be any amino acid (SEQ ID NO:40).

A suitable endodomain may be an ITAM motif-containing portion that is derived from a polypeptide that contains an ITAM motif. For example, a suitable endodomain can be an ITAM motif-containing domain from any ITAM motif-containing protein. Thus, a suitable endodomain need not contain the entire sequence of the entire protein from which it is derived. Examples of suitable ITAM motif-containing polypeptides include, but are not limited to: DAP12; FCER1G (Fc epsilon receptor I gamma chain); CD3D (CD3 delta); CD3E (CD3 epsilon); CD3G (CD3 gamma); CD3Z (CD3 zeta); and CD79A (antigen receptor complex-associated protein alpha chain).

In some cases, the endodomain is derived from DAP12 (also known as TYROBP; TYRO protein tyrosine kinase binding protein; KARAP; PLOSL; DNAX—activation protein 12; KAR-associated protein; TYRO protein tyrosine kinase-binding protein; killer activating receptor associated protein; killer-activating receptor-associated protein; etc.). For example, a suitable endodomain polypeptide can comprise an amino acid sequence having at least 75%, at least 80%, at least 85%, at least 90%, at least 95%, at least 98%, or 100%, amino acid sequence identity to (SEQ ID NO: 41)
MGGLEPCSRLLLLPLLLAVSGLRPVQAQAQSDCSCSTVSPGVLAGIVMGD

LVLTVLIALAVYFLGRLVPRGRGAAEAATRKORITETESPYOELOGORSD

VYSDLNTQRPYYK;

(SEQ ID NO: 42)
MGGLEPCSRLLLLPLLLAVSGLRPVQAQAQSDCSCSTVSPGVLAGIVMGD

LVLTVLIALAVYFLGRLVPRGRGAAEATRKORITETESPYOELOGORSDV

YSDLNTQRPYYK;

(SEQ ID NO: 43)
MGGLEPCSRLLLLPLLLAVSDCSCSTVSPGVLAGIVMGDLVLTVLIALAV

YFLGRLVPRGRGAAEAATRKORITETESPYOELOGORSDVYSDLNTQRPY

YK;
or (SEQ ID NO: 44)
MGGLEPCSRLLLLPLLLAVSDCSCSTVSPGVLAGIVMGDLVLTVLIALAV

YFLGRLVPRGRGAAEATRKORITETESPYOELOGORSDVYSDLNTQRPYY

K.

In some embodiments, a suitable endodomain polypeptide can comprise an ITAM motif-containing portion of the full length DAP12 amino acid sequence. Thus, a suitable endodomain polypeptide can comprise an amino acid sequence having at least 75%, at least 80%, at least 85%, at least 90%, at least 95%, at least 98%, or 100%, amino acid sequence identity to (SEQ ID NO: 45)
ESPYOELOGORSDVYSDLNTO.

In some embodiments, the endodomain is derived from FCER1G (also known as FCRG; Fc epsilon receptor I gamma chain; Fc receptor gamma-chain; fc-epsilon R1-gamma; fcRgamma; fceRI gamma; high affinity immunoglobulin epsilon receptor subunit gamma; immunoglobulin E receptor, high affinity, gamma chain; etc.). For example, a suitable endodomain polypeptide can comprise an amino acid sequence having at least 75%, at least 80%, at least 85%, at least 90%, at least 95%, at least 98%, or 100% amino acid sequence identity to (SEQ ID NO: 46)
MIPAVVLLLLLLVEQAAALGEPQLCYILDAILFLYGIVLTLLYCRLKIQV

RKAAITSYEKSDGVYTGLSTRNQETYETLKHEKPPQ.

In some embodiments, a suitable endodomain polypeptide can comprise an ITAM motif-containing portion of the full length FCER1G amino acid sequence. Thus, a suitable endodomain polypeptide can comprise an amino acid sequence having at least 75%, at least 80%, at least 85%, at least 90%, at least 95%, at least 98%, or 100%, amino acid sequence identity to (SEQ ID NO: 47)
DGVYTGLSTRNOETYETLKHE.

In some embodiments, the endodomain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 170 aa, of either of the following amino acid sequences (2 isoforms):

(SEQ ID NO: 48)
MEHSTFLSGLVLATLLSQVSPFKIPIEELEDRVFVNCNTSITWVEGTVGT

LLSDITRLDLGKRILDPRGIYRCNGTDIYKDKESTVQVHYRMCQSCVELD

PATVAGIIVTDVIATLLLALGVFCFAGHETGRLSGAADTOALLRNDOVYO

PLRDRDDAOYSHLGGNWARNK
or (SEQ ID NO: 49)
MEHSTFLSGLVLATLLSQVSPFKIPIEELEDRVFVNCNTSITWVEGTVGT

LLSDITRLDLGKRILDPRGIYRCNGTDIYKDKESTVOVHYRTADTOALLR

NDOVYOPLRDRDDAQYSHLGGNWARNK.

In some embodiments, a suitable endodomain polypeptide can comprise an ITAM motif-containing portion of the full length CD3 delta amino acid sequence. Thus, a suitable endodomain polypeptide can comprise an amino acid sequence having at least 75%, at least 80%, at least 85%, at least 90%, at least 95%, at least 98%, or 100%, amino acid sequence identity to (SEQ ID NO: 50)
DOVYOPLRDRDDAOYSHLGGN.

In some embodiments, the endodomain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 205 aa, of the following amino acid sequence:

(SEQ ID NO: 51)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI.

In some embodiments, a suitable endodomain polypeptide can comprise an ITAM motif-containing portion of the full length CD3 epsilon amino acid sequence. Thus, a suitable endodomain polypeptide can comprise an amino acid sequence having at least 75%, at least 80%, at least 85%, at least 90%, at least 95%, at least 98%, or 100%, amino acid sequence identity to (SEQ ID NO: 52)
NPDYEPIRKGQRDLYSGLNQR.

In some embodiments, the endodomain is derived from T-cell surface glycoprotein CD3 gamma chain (also known as CD3G, T-cell receptor T3 gamma chain, CD3-GAMMA, T3G, gamma polypeptide (TiT3 complex), etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 180 aa, of the following amino acid sequence:

(SEQ ID NO: 53)
MEQGKGLAVLILAIILLQGTLAQSIKGNHLVKVYDYQEDGSVLLTCDAEA

KNITWFKDGKMIGFLTEDKKKWNLGSNAKDPRGMYQCKGSQNKSKPLQVY

YRMCQNCIELNAATISGFLFAEIVSIFVLAVGVYFIAGQDGVROSRASDK

QTLLPNDQLYOPLKDREDDQYSHLQGNQLRRN.

In some embodiments, a suitable endodomain polypeptide can comprise an ITAM motif-containing portion of the full length CD3 gamma amino acid sequence. Thus, a suitable endodomain polypeptide can comprise an amino acid sequence having at least 75%, at least 80%, at least 85%, at least 90%, at least 95%, at least 98%, or 100%, amino acid sequence identity to (SEQ ID NO: 54)
DQLYOPLKDREDDQYSHLQGN.

In some embodiments, the endodomain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). For example, a suitable intracellular signaling domain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms):

(SEQ ID NO: 55)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR or (SEQ ID NO: 56)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR.

In some embodiments, a suitable endodomain polypeptide can comprise an ITAM motif-containing portion of the full length CD3 zeta amino acid sequence. Thus, a suitable endodomain polypeptide can comprise an amino acid sequence having at least 75%, at least 80%, at least 85%, at least 90%, at least 95%, at least 98%, or 100%, amino acid sequence identity to any of the following amino acid sequences:

(SEQ ID NO: 90)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR;

(SEQ ID NO: 57)
NQLYNELNLGRREEYDVLDKR;

(SEQ ID NO: 58)
EGLYNELQKDKMAEAYSEIGMK;

or (SEQ ID NO: 59)
DGLYQGLSTATKDTYDALHMQ.

In some embodiments, the endodomain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). For example, a suitable endodomain polypeptide can comprise an amino acid sequence having at least 75%, at least 80%, at least 85%, at least 90%, at least 95%, at least 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 150 aa, from about 150 aa to about 200 aa, or from about 200 aa to about 220 aa, of either of the following amino acid sequences (2 isoforms):

(SEQ ID NO: 60)
MPGGPGVLQALPATIFLLFLLSAVYLGPGCQALWMHKVPASLMVSLGEDA

HFQCPHNSSNNANVTWWRVLHGNYTWPPEFLGPGEDPNGTLIIQNVNKSH

GGIYVCRVQEGNESYQQSCGTYLRVRQPPPRPFLDMGEGTKNRIITAEGI

ILLFCAVVPGTLLLFRKRWONEKLGLDAGDEYEDENLYEGLNLDDCSMYE

DISRGLOGTYQDVGSLNIGDVQLEKP;
or (SEQ ID NO: 61)
MPGGPGVLQALPATIFLLFLLSAVYLGPGCQALWMHKVPASLMVSLGEDA

HFQCPHNSSNNANVTWWRVLHGNYTWPPEFLGPGEDPNEPPPRPFLDMGE

GTKNRIITAEGIILLFCAVVPGTLLLFRKRWQNEKLGLDAGDEYEDENLY

EGLNLDDCSMYEDISRGLQGTYQDVGSLNIGDVQLEKP.

In some embodiments, a suitable endodomain polypeptide can comprise an ITAM motif-containing portion of the full length CD79A amino acid sequence. Thus, a suitable endodomain polypeptide can comprise an amino acid sequence having at least 75%, at least 80%, at least 85%, at least 90%, at least 95%, at least 98%, or 100%, amino acid sequence identity to the following amino acid sequence:

(SEQ ID NO: 62)
ENLYEGLNLDDCSMYEDISRG.

In some embodiments, suitable endodomains can comprise a DAP10/CD28 type signaling chain. An example of a DAP 10 signaling chain is the amino acid sequence:

(SEQ ID NO: 63)
RPRRSPAQDGKVYINMPGRG.

In some embodiments, a suitable endodomain comprises an amino acid sequence having at least 85%, at least 90%, at least 95%, at least 98%, or at least 99%, amino acid sequence identity to the entire length of the amino acid sequence (SEQ ID NO: 64)
RPRRSPAQDGKVYINMPGRG.

An example of a CD28 signaling chain is the amino acid sequence (SEQ ID NO: 65)
FWVLVVVGGVLACYSLLVTVAFIIFWVRSKRSRLLHSDYMNMTPRRPGPT

RKHYQPYAPPRDFAAYRS.

In some embodiments, a suitable endodomain comprises an amino acid sequence having at least 85%, at least 90%, at least 95%, at least 98%, or at least 99%, amino acid sequence identity to the entire length of the amino acid sequence (SEQ ID NO: 66)
FWVLVVVGGVLACYSLLVTVAFIIFWVRSKRSRLLHSDYMNMTPRRPGPT

RKHYQPYAPPRDFAAYRS.

Further endodomains suitable for use in the polypeptides of the disclosure include a ZAP70 polypeptide, e.g., a polypeptide comprising an amino acid sequence having at least 85%, at least 90%, at least 95%, at least 98%, at least 99%, or 100%, amino acid sequence identity to a contiguous stretch of from about 300 amino acids to about 400 amino acids, from about 400 amino acids to about 500 amino acids, or from about 500 amino acids to 619 amino acids, of the following amino acid sequence:

(SEQ ID NO: 67)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPQRRIDTLNSDGYTPEPARIT

SPDKPRPMPMDTSVYESPYSDPEELKDKKLFLKRDNLLIADIELGCGNFG

SVRQGVYRMRKKQIDVAIKVLKQGTEKADTEEMMREAQIMHQLDNPYIVR

LIGVCQAEALMLVMEMAGGGPLHKFLVGKREEIPVSNVAELLHQVSMGMK

YLEEKNFVHRDLAARNVLLVNRHYAKISDFGLSKALGADDSYYTARSAGK

WPLKWYAPECINFRKFSSRSDVWSYGVTMWEALSYGQKPYKKMKGPEVMA

FIEQGKRMECPPECPPELYALMSDCWIYKWEDRPDFLTVEQRMRACYYSL

ASKVEGPPGSTQKAEAACA.

g. Detection Peptides

CARs can include detection peptides. Suitable detection peptides include hemagglutinin (HA; e.g., YPYDVPDYA (SEQ ID NO:68); FLAG (e.g., DYKDDDDK (SEQ ID NO:69); c-myc (e.g., EQKLISEEDL; SEQ ID NO:70), and the like. Other suitable detection peptides are known in the art.

h. Peptide Linkers

In some embodiments, CARs may also include peptide linkers (sometimes referred to as a linker). A peptide linker may be separating any of the peptide domain/regions described herein. As an example, a linker may be between the signal peptide and the antigen binding domain, between the $V_H$ and $V_L$ of the antigen binding domain, between the antigen binding domain and the peptide spacer, between the peptide spacer and the transmembrane domain, flanking the co-stimulatory region or on the N- or C-region of the co-stimulatory region, and/or between the transmembrane domain and the endodomain. The peptide linker may have any of a variety of amino acid sequences. Domains and regions can be joined by a peptide linker that is generally of a flexible nature, although other chemical linkages are not excluded. A linker can be a peptide of between about 6 and about 40 amino acids in length, or between about 6 and about 25 amino acids in length. These linkers can be produced by using synthetic, linker-encoding oligonucleotides to couple the proteins.

Peptide linkers with a degree of flexibility can be used. The peptide linkers may have virtually any amino acid sequence, bearing in mind that suitable peptide linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO:71) and $(GGGS)_n$ (SEQ ID NO:72), where n is an integer of at least one, glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains. Exemplary spacers can comprise amino acid sequences including, but not limited to, GGSG (SEQ ID NO:73), GGSGG (SEQ ID NO:74), GSGSG (SEQ ID NO:75), GSGGG (SEQ ID NO:76), GGGSG (SEQ ID NO:77), GSSSG (SEQ ID NO:78), and the like.

i. Co-Stimulatory Region

Non-limiting examples of suitable co-stimulatory regions in CARs include, but are not limited to, polpeptides from 4-1BB (CD137), CD28, ICOS, OX-40, BTLA, CD27, CD30, GITR, and HVEM.

A co-stimulatory region may have a length of at least, at most, or exactly 20, 25, 30, 35, 40, 50, 60, 70, 80, 90, 100, 150, 200, or 300 amino acids or any range derivable therein. In some embodiments, the co-stimulatory region is derived from an intracellular portion of the transmembrane protein 4-1BB (also known as TNFRSF9; CD137; 4-1BB; CDw137; ILA; etc.). For example, a suitable co-stimulatory region can comprise an amino acid sequence having at least 75%, at least 80%, at least 85%, at least 90%, at least 95%, at least 98%, or 100% amino (SEQ ID NO: 79)
KRGRKKLLYIFKQPFMRPVQTTQEEDGCSCRFPEEEEGGCEL.

In some embodiments, the co-stimulatory region is derived from an intracellular portion of the transmembrane protein CD28 (also known as Tp44). For example, a suitable co-stimulatory region can comprise an amino acid sequence having at least 75%, at least 80%, at least 85%, at least 90%, at least 95%, at least 98%, or 100% amino acid sequence identity to (SEQ ID NO: 80)
FWVRSKRSRLLHSDYMNMTPRRPGPTRKHYQPYAPPRDFAAYRS.

In some embodiments, the co-stimulatory region is derived from an intracellular portion of the transmembrane protein ICOS (also known as AILIM, CD278, and CVID1). For example, a suitable co-stimulatory region can comprise an amino acid sequence having at least 75%, at least 80%, at least 85%, at least 90%, at least 95%, at least 98%, or 100% amino acid sequence identity to (SEQ ID NO: 81)
TKKKYSSSVHDPNGEYMFMRAVNTAKKSRLTDVTL.

In some embodiments, the co-stimulatory region is derived from an intracellular portion of the transmembrane protein OX-40 (also known as TNFRSF4, RP5-902P8.3, ACT35, CD134, OX40, TXGP1L). For example, a suitable co-stimulatory region can comprise an amino acid sequence having at least 75%, at least 80%, at least 85%, at least 90%, at least 95%, at least 98%, or 100% amino acid sequence identity to (SEQ ID NO: 82)
RRDQRLPPDAHKPPGGGSFRTPIQEEQADAHSTLAKI.

In some embodiments, the co-stimulatory region is derived from an intracellular portion of the transmembrane protein BTLA (also known as BTLA1 and CD272). For example, a suitable co-stimulatory region can comprise an amino acid sequence having at least 75%, at least 80%, at least 85%, at least 90%, at least 95%, at least 98%, or 100% amino acid sequence identity to (SEQ ID NO: 83)
CCLRRHQGKQNELSDTAGREINLVDAHLKSEQTEASTRQNSQVLLSETGI
YDNDPDLCFRMQEGSEVYSNPCLEENKPGIVYASLNHSVIGPNSRLARNV
KEAPTEYASICVRS.

In some embodiments, the co-stimulatory region is derived from an intracellular portion of the transmembrane protein CD27 (also known as S 152, T14, TNFRSF7, and Tp55). For example, a suitable co-stimulatory region can comprise an amino acid sequence having at least 75%, at least 80%, at least 85%, at least 90%, at least 95%, at least 98%, or 100% amino acid sequence identity to (SEQ ID NO: 84)
HQRRKYRSNKGESPVEPAEPCRYSCPREEEGSTIPIQEDYRKPEPACSP.

In some embodiments, the co-stimulatory region is derived from an intracellular portion of the transmembrane protein CD30 (also known as TNFRSF8, D1S166E, and Ki-1). For example, a suitable co-stimulatory region can comprise an amino acid sequence having at least 75%, at least 80%, at least 85%, at least 90%, at least 95%, at least 98%, or 100% amino acid sequence identity to (SEQ ID NO: 85)
RRACRKRIRQKLHLCYPVQTSQPKLELVDSRPRRSSTQLRSGASVTEPVA
EERGLMSQPLMETCHSVGAAYLESLPLQDASPAGGPSSPRDLPEPRVSTE
HTNNKIEKIYIMKADTVIVGTVKAELPEGRGLAGPAEPELEEELEADHTP
HYPEQETEPPLGSCSDVMLSVEEEGKEDPLPTAASGK.

In some embodiments, the co-stimulatory region is derived from an intracellular portion of the transmembrane protein GITR (also known as TNFRSF18, RP5-902P8.2, AITR, CD357, and GITR-D). For example, a suitable co-stimulatory region can comprise an amino acid sequence having at least 75%, at least 80%, at least 85%, at least 90%, at least 95%, at least 98%, or 100% amino acid sequence identity to

HIWQLRSQCMWPRETQLLLEVPPSTEDARSCQFPEEERGERSAEEKGRLG DLWV. (SEQ ID NO: 86)

In some embodiments, the co-stimulatory region derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory region can comprise an amino acid sequence having at least 75%, at least 80%, at least 85%, at least 90%, at least 95%, at least 98%, or 100% amino acid sequence identity to

CVKRRKPRGDVVKVIVSVQRKRQEAEGEATVIEALQAPPDVTTVAVEETI PSFTGRSPNH. (SEQ ID NO: 87)

V. METHODS

Aspects of the current disclosure relate to methods of treating a condition, for stimulating an immune response, for regulating an immune response, for suppressing an immune response, and for reducing the risk of an adverse immune response, such as cytokine release syndrome. These actions may be done in vitro, in vivo, or ex vivo. In some embodiments, the methods relate to cells capable of stimulating an immune response in the presence of a cancer cell. The method generally involves genetically modifying a mammalian cell with an expression vector, or an RNA (e.g., in vitro transcribed RNA), comprising nucleotide sequences encoding a polypeptide of the disclosure or directly transferring the polypeptide to the cell. The cell can be an immune cell (e.g., a T lymphocyte or NK cell), a stem cell, a progenitor cell, etc. In some embodiments, the cell is a cell described herein.

In some embodiments, the genetic modification is carried out ex vivo. For example, a T lymphocyte, a stem cell, or an NK cell (or cell described herein) is obtained from an individual; and the cell obtained from the individual is genetically modified to express a polypeptide of the disclosure. In some cases, the genetically modified cell is activated ex vivo (i.e., a target antigen is contacted with the cells ex vivo). In other cases, the genetically modified cell is introduced into an individual (e.g., the individual from whom the cell was obtained); and the genetically modified cell is activated in vivo (i.e., by endogenously produced target antigen).

In some embodiments, the methods further comprise the administration of additional therapeutic agents, such as bi-specific T cell engagers (BITE). Such therapeutic agents may be administered in peptide form to the patient or expressed in cells of the disclosure, such as those that that comprise the IL-6Rα binding protein. The BITE may have antigen specificity for a cancer antigen/cancer molecule known in the art and/or described herein and may also have antigen specificity for a T cell molecule such as CD3.

In some embodiments, the methods relate to administration of the cells or peptides described herein for the treatment of a cancer or administration to a person with a cancer. In some embodiments the cancer is adrenal cancer, anal cancer, bile duct cancer, bladder cancer, bone cancer, brain/ CNS tumors in children or adults, breast cancer, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestation trophoblastic disease, hodgkin disease, kaposi sarcoma, kidney cancer, laryngeal and hypopharyngeal cancer, leukemia, acute lymphocytic leuckemia, acute myeloid leukemia, chronic lymphocytic leukemia, chronic myeloid leukemia, chronic myelomonocytic leukemia, liver cancer, lung cancer, non-small cell lung cancer, small cell lung cancer, lung carcinoid tumor, lymphoma, malignant mesothelioma, multiple myeloma, myelodysplastic syndrome, nasal cavity and paranasal sinum cancer, nasopharyngeal cancer, neuroblastoma, non-hodgkin lymphoma, oral cavity or oropharyngeal cancer, osteosarcoa, ovarian cancer, pancreatic cancer, penile cancer, pituitary tumors, prostate cancer, retinoblastoma, rhabdomyosarcoma, salivary gland cancer, skin cancer, sarcoma, basal skin cancer, squamous cell skin cancer, melanoma, merkel cell skin cancer, small intestine cancer, stomach cancer, testicular cancer, thymus cancer, thyroid cancer, uterine sarcoma, vaginal cancer, vulvar cancer, waldenstrom macroglobulinemia, or wilms tumor.

Embodiments can be used to treat or ameliorate a number of immune-mediated, inflammatory, or autoimmune-inflammatory diseases, e.g., allergies, asthma, diabetes (e.g. type 1 diabetes), graft rejection, etc. Examples of such diseases or disorders also include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen *nitidus*, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus *foliaceus*, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes *dorsalis*, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aserniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

In some embodiments, the patient is one that does not have a particular indication described above. For example, in some embodiments, the patient does not have and/or has not been diagnosed with rheumatoid arthritis. In some embodiments, the patient does not have a chronic autoimmune condition. The term chronic refers to an illness that is persisting for a long time or constantly recurring.

VI. PHARMACEUTICAL COMPOSITIONS

The present disclosure includes methods for modulating immune responses in a subject in need thereof. The disclosure includes cells and proteins that may be in the form of a pharmaceutical composition that can be used to induce or modify an immune response.

Administration of the compositions according to the current disclosure will typically be via any common route. This includes, but is not limited to parenteral, orthotopic, intradermal, subcutaneous, intramuscular, intraperitoneal, intranasal, or intravenous injection.

Typically, compositions of the invention are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of pharmaceutical compositions comprising cellular components are applicable. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2-day to 12-week intervals, more usually from one to two week intervals. The course of the administrations may be followed by assays for alloreactive immune responses and T cell activity.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. The pharmaceutical compositions of the current disclosure are pharmaceutically acceptable compositions.

The compositions of the disclosure can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol. It also should be stable under the conditions of manufacture and storage and must be preserved against the contaminating action of microorganisms, such as bacteria and fungi.

Sterile injectable solutions are prepared by incorporating the active ingredients (i.e. cells of the disclosure) in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

An effective amount of a composition is determined based on the intended goal. The term "unit dose" or "dosage" refers to physically discrete units suitable for use in a subject, each unit containing a predetermined quantity of the composition calculated to produce the desired responses discussed herein in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

VII. EXAMPLES

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Anti-IL-6Rα scFv Constructs Inhibit IL-6 Signaling

This disclosure describes single-chain variable fragments (scFvs) that bind to IL-6Rα. In this Example, two different anti-IL-6Rα scFv constructs are used: a $V_H V_L$ construct (SEQ ID NO:2) and a $V_L V_H$ construct (SEQ ID NO:1). These constructs differ only in that the positions of the $V_H$ and $V_L$ sequences are switched.

IL-6 is a cytokine that has pro-inflammatory effects. IL-6 signals through IL-6Rα, which is the ligand-binding component of IL-6's cell surface receptor. IL-6 signaling through IL-6Rα plays a role in a pro-inflammatory cytokine signaling processes, including in cytokine release syndrome. IL-6 also stimulates the inflammatory and auto-immune processes in many diseases, including diabetes, atherosclerosis, depression, Alzheimer's Disease, systemic lupus erythematosus, multiple myeloma, prostate cancer, Behget's disease, and rheumatoid arthritis.

Both of the anti-IL-6Rα scFvs are effective at inhibiting IL-6 signaling in HepG2 cells. HepG2 human hepatocarcinoma cells were seeded in a 12-well plate and incubated with 1, 2, or 5 μg of scFv for 3 hours. Some of the wells, as indicated in FIG. 1, were subsequently treated with 4 ng/ml of IL-6 and incubated for another 30 minutes before cell harvest. The presence of phosphorylated STAT3 (pSTAT3), a major signaling molecule in the IL-6 signaling pathway, was probed by western blot. The results in FIG. 1 indicate that scFvs with either $V_L$-$V_H$ (SEQ ID NO:1) or $V_H$-$V_L$ (SEQ ID NO:2) orientations are able to inhibit IL-6 signaling in a dose-dependent manner, as higher concentrations of the scFvs resulted in lower levels of pSTAT3 expression in response to IL-6. Subsequent experiments were performed using the $V_L$-$V_H$ scFv (SEQ ID NO:1).

Figure 2:
FIG. 2. Anti-IL-6Rα scFv inhibits IL-6 signaling in primary human T cells. Primary human CD4+ and CD8+ T cells were seeded in a 12-well plate and treated as described for FIG. 1. The $V_L$-$V_H$ scFv (SEQ ID NO:1) was added in the indicated amounts, and IL-6 was added to the indicated wells. pSTAT3 and GAPDH (loading control) were detected by western blot.

To determine whether anti-IL-6Rα scFv inhibits IL-6 signaling in primary human T cells, primary human CD4$^+$ and CD8$^+$ T cells were seeded in a 12-well plate and treated as described for the HepG2 cells in FIG. 1. The $V_L$-$V_H$ scFv (SEQ ID NO:1) was added to the wells in the concentrations indicated in FIG. 2, along with IL-6 in the indicated wells. The presence of pSTAT3 was once again probed by western blot. The results in FIG. 2 indicate that the anti-IL-6Rα scFv inhibits IL-6 signaling in a dose-dependent manner in both CD4$^+$ and CD8$^+$ primary human T cells.

These results indicate that administering effective amounts of anti-IL-6Rα scFv to a subject would treat inflammatory conditions such as CRS and autoimmune and other diseases in which IL-6 signaling is involved.

Example 2

Expression of Anti-IL-6Rα scFv Constructs by T Cells

Preparation of primary human CD4$^+$ and CD8$^+$ cells expressing an anti-CD19 chimeric antigen receptor (CAR)

and anti-IL-6Rα scFv: Human primary T cells were isolated and stimulated with CD3/CD28 dynabeads on the day of isolation. Two days after isolation, T cells were transduced with lentivirus or retrovirus vectors encoding anti-CD19 CAR (SEQ ID NO:88) and IL-6Rα scFv constructs encoding SEQ ID NO:1 or SEQ ID NO:2 (or no IL-6Rα scFv for controls). Dynabeads were removed on day 9 post isolation. Cells were sorted by magnetic cell separation based on the HA-tag on anti-CD19 CAR. On day 21 of CD4 T cells and day 14 of CD8 T cells, primary T cells were expanded by a Rapid Expansion Protocol, in which $0.5 \times 10^6$ of T cells are mixed with $3.5 \times 10^6$ irradiated TM-LCL, 50 U/ml rhIL-2 and 1 ng/ml rhIL-15 in 25 ml of complete RPMI media in a T25 flask. Cytokines are replenished every 2 days. Cells are used for experiments after day 9 of the REP.

Figure 3:
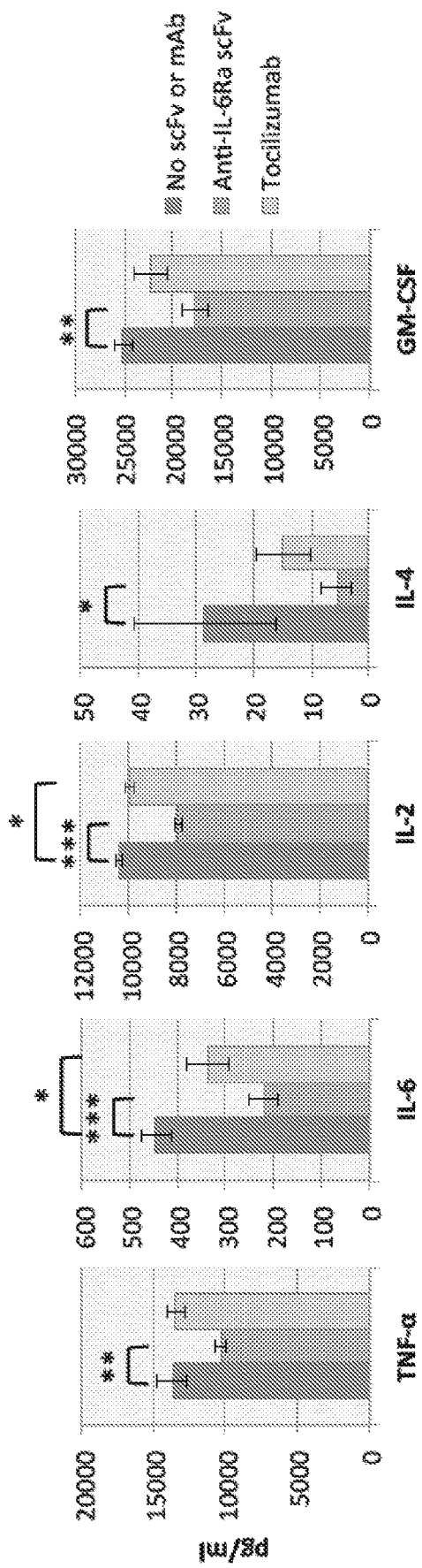
FIG. 3. Constitutive expression of anti-IL-6Rα scFv significantly reduces the production of inflammatory cytokines by primary human T cells. Primary human CD4+ T cells expressing an anti-CD19 chimeric antigen receptor (CAR) with ("anti-IL-6Rα scFv," middle bars) or without ("No scFv or mAb"; left bars) constitutive expression of the anti-IL-6Rα scFv were co-incubated with peripheral blood mononuclear cells (PBMCs) from the same donor plus wild-type (CD19+) Raji lymphoma cells at a 1:1:1 ratio for 12 hours. Non-scFv-expressing CD19 CAR-T cells treated with 90 µg/ml of the monoclonal antibody tocilizumab were included as control samples ("Tocilizumab"; right bars). Cytokine levels in culture media were quantified by a cytometric bead-based assay. Values shown are the means of three technical replicates with error bars indicating ±1 standard deviation. Statistical significance was evaluated by two-tailed, equal-variance Student's t-test; * p<0.05;  p<0.01; * p<0.001. The results shown are representative of two independent experiments using cells from two different healthy blood donors.

The inventors tested the effect of expressing the anti-IL-6Rα scFv in T cells. Primary human CD4$^+$ T cells expressing the anti-CD19 chimeric antigen receptor (CAR) with or without constitutive expression of the anti-IL-6Rα scFv were co-incubated with peripheral blood mononuclear cells (PBMCs) from the same donor as the CD4$^+$ T cells plus wild-type (CD19$^+$) Raji lymphoma cells at a 1:1:1 ratio for 12 hours. Non-scFv-expressing CD19 CAR-T cells with 90 µg/ml of the monoclonal antibody tocilizumab were included as control samples. Levels of the cytokines in culture media as indicated in FIG. 3 were quantified by a cytometric bead-based assay. Values shown in FIG. 3 are the means of three technical replicates with error bars indicating ±1 standard deviation. Statistical significance was evaluated by two-tailed, equal-variance Student's t-test; * $p<0.05$;  $p<0.01$; * $p<0.001$. The results shown are representative of two independent experiments using cells from two different healthy blood donors. The results in FIG. 3 show that constitutive expression by primary human T cells of anti-IL-6Rα scFv significantly reduces the production of inflammatory cytokines by the T cells. This indicates that the incidence of CRS in adoptive T cell therapy could be reduced by using T cells expressing an anti-IL-6Rα scFv.

Figure 4:
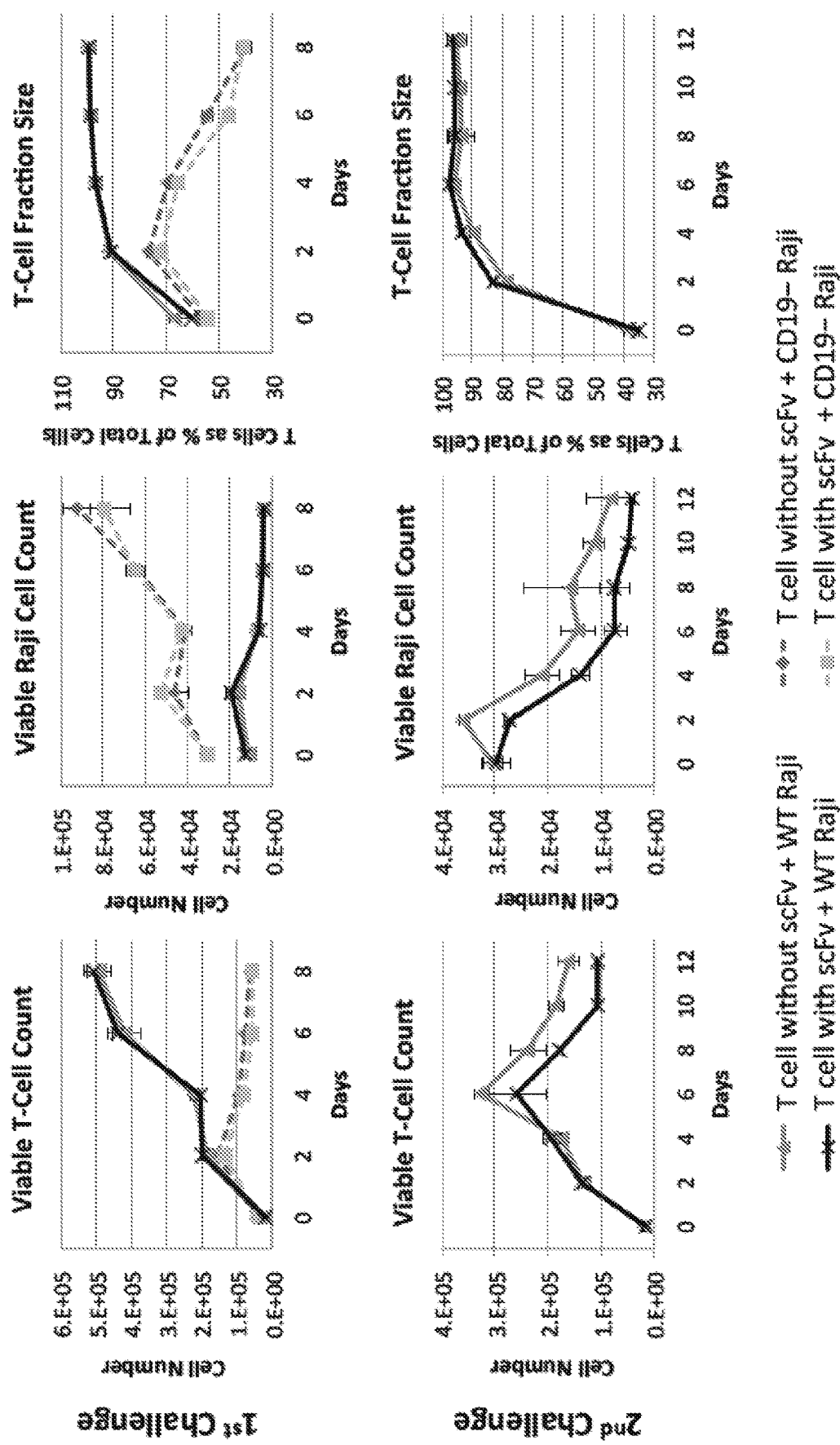
FIG. 4. Constitutive expression of anti-IL-6Rα scFv does not inhibit T-cell proliferation or cytotoxicity in CD4+ T cells. Primary human CD4+ T cells constitutively expressing the anti-CD19 CAR with or without the anti-IL-6Rα scFv were co-incubated with wild-type (WT; CD19+) or CD19− mutant Raji lymphoma cells at a 2:1 effector-to-target (E:T) ratio. Viable T-cell and Raji-cell counts were obtained by flow cytometry every two days. Both Raji cell lines stably express EGFP to enable separation from T cells during flow-cytometry analysis. After cell counting on day 8, T cells co-incubated with WT Raji were harvested and re-challenged with fresh WT Raji cells at a 2:1 E:T ratio. Viable cell counts were monitored for another 12 days during the second challenge. Values shown are the means of three technical replicates with error bars indicating ±1 standard deviation. The results shown are representative of four independent experiments using cells from two different healthy blood donors.
Figure 6:
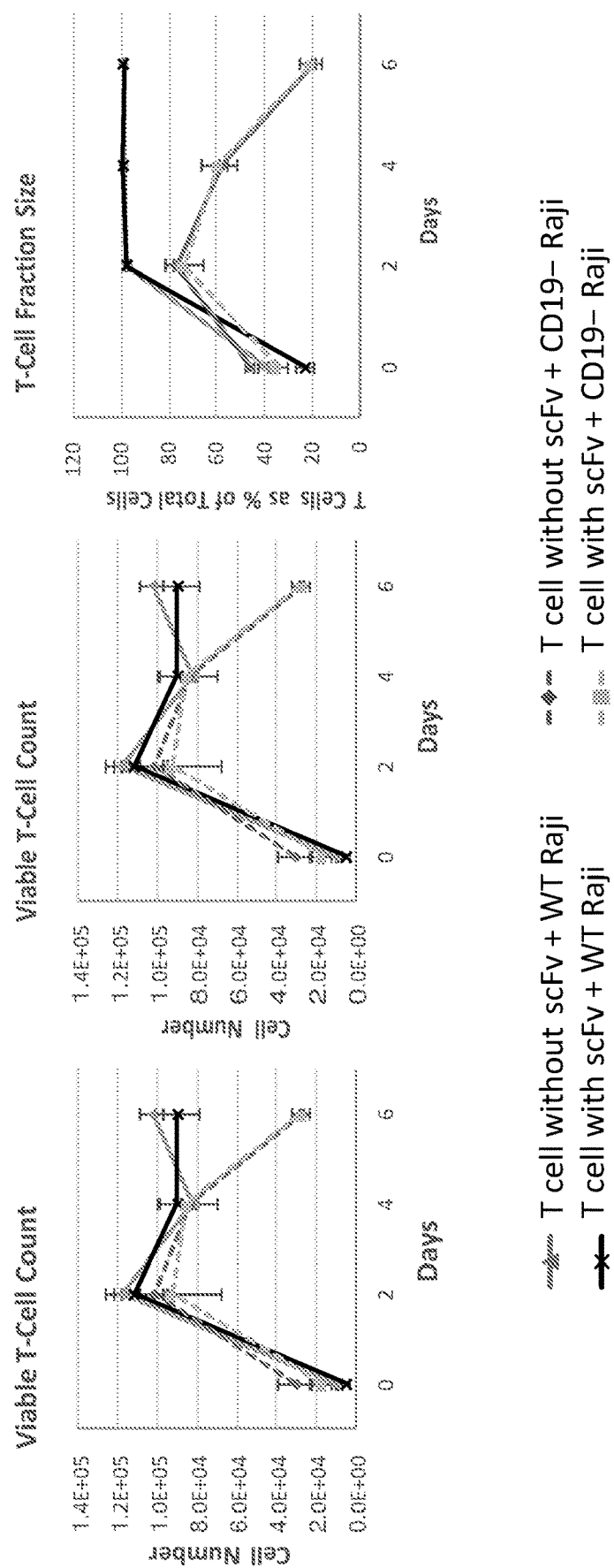
FIG. 6. Constitutive expression of anti-IL-6Rα scFv does not inhibit T-cell proliferation or cytotoxicity in CD8+ T cells. Primary human CD8+ T cells constitutively expressing the anti-CD19 CAR with or without the anti-IL-6Rα scFv were co-incubated with wild-type (WT; CD19+) or CD19− mutant Raji lymphoma cells at a 2:1 effector-to-target (E:T) ratio. Viable T-cell and Raji-cell counts were obtained by flow cytometry every two days. Both Raji cell lines stably express EGFP to enable separation from T cells during flow-cytometry analysis. Values shown are the means of three technical replicates with error bars indicating ±1 standard deviation. The results shown are representative of three independent experiments using cells from two different healthy blood donors.

The inventors next tested whether expression of anti-IL-6Rα scFv by T cells would inhibit their proliferation or cytotoxicity. Primary human CD4$^+$ and CD8$^+$ T cells constitutively expressing the anti-CD19 CAR with or without the anti-IL-6Rα scFv were co-incubated with wild-type (WT; CD19$^+$) or CD19– mutant Raji lymphoma cells at a 2:1 effector-to-target (E:T) ratio. Viable T-cell and Raji-cell counts were obtained by flow cytometry every two days. Both Raji cell lines stably express EGFP to enable separation from T cells during flow-cytometry analysis. After cell counting on day 8, CD4$^+$ T cells co-incubated with WT Raji were harvested and re-challenged with fresh WT Raji cells at a 2:1 E:T ratio. Viable cell counts were monitored for another 12 days during the second challenge. Values shown in FIGS. 4 and 6 are the means of three technical replicates with error bars indicating ±1 standard deviation. The results shown in FIG. 4 are representative of four independent experiments using cells from two different healthy blood donors, and the results in FIG. 6 are representative of three independent experiments using cells from two different healthy blood donors. The results in FIGS. 4 and 6 demonstrate that constitutive expression of anti-IL-6Rα scFv by T cells does not inhibit T-cell proliferation or cytotoxicity, which indicates that the efficacy of adoptive T cell therapy would not be diminished by using T cells that express an anti-IL-6Rα scFv.

Figure 5:
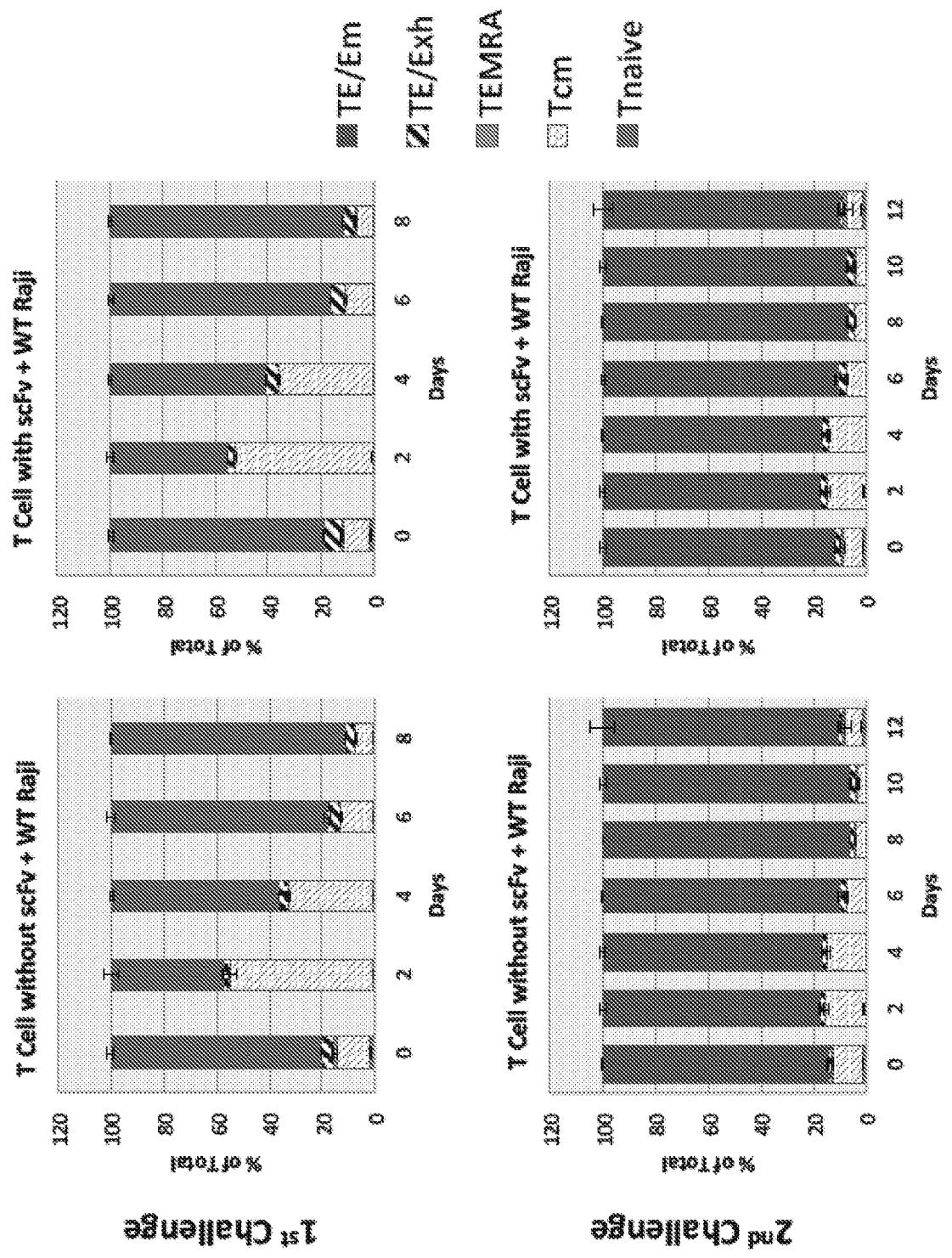
FIG. 5. Constitutive expression of anti-IL-6Rα scFv does not alter T-cell subtype differentiation upon antigen stimulation in CD4+ T cells. In the same experiment shown in FIG. 4, CD4+ primary human T cells were surface-stained with antibody for CCR7, CD45RA, and CD57 to determine the T-cell subtype. $T_{E/EM}$: CCR7−/CD45RA−/CD57−; $T_{E/Exh}$: CCR7−/CD45RA−/CD57+; $T_{EMRA}$: CCR7−/CD45RA+; $T_{cm}$: CCR7+/CD45RA−; $T_{naive}$: CCR7+/CD45RA+. Values shown are the means of three technical replicates with error bars indicating ±1 standard deviation. The results shown are representative of four independent experiments using cells from two different healthy blood donors.
Figure 7:
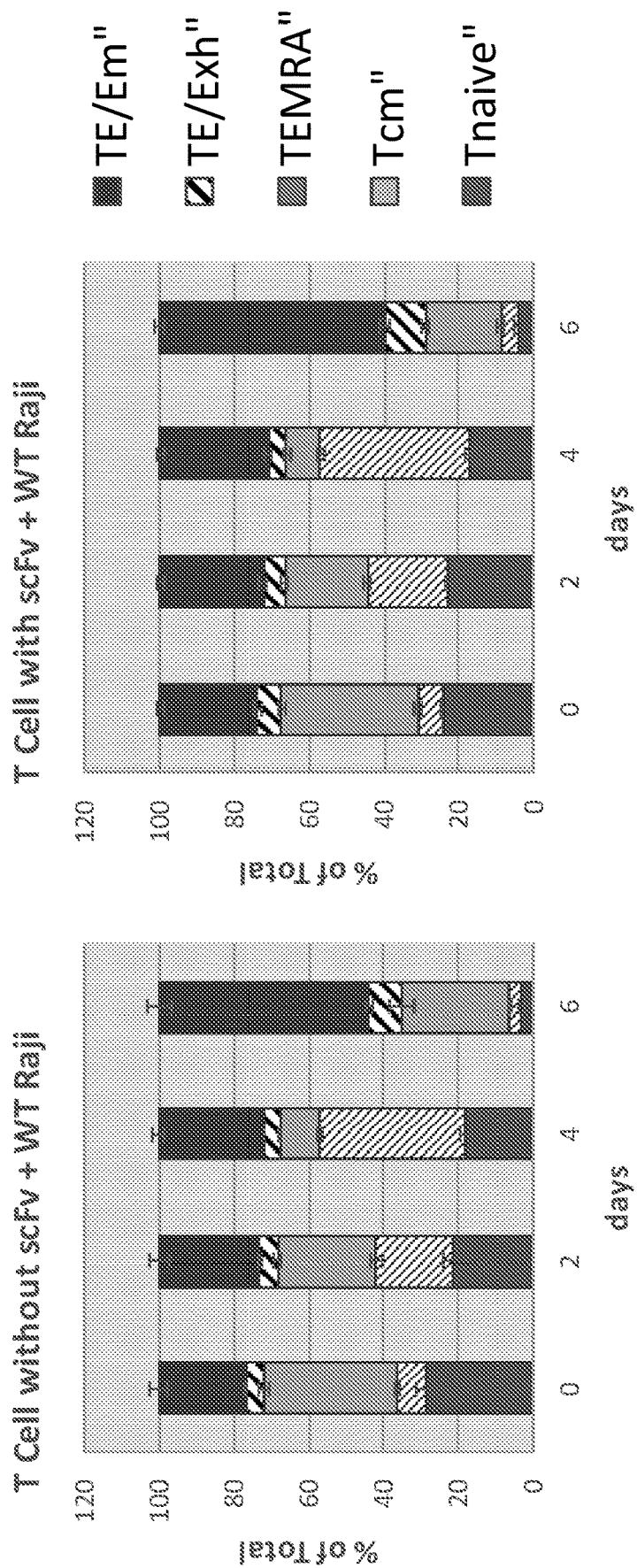
FIG. 7. Constitutive expression of anti-IL-6Rα scFv does not alter T-cell subtype differentiation upon antigen stimulation in CD8+ T cells. In the same experiment as described in FIG. 1, primary CD8+ human T cells were surface-stained with antibody for CCR7, CD45RA, and CD57 to determine the T-cell subtype. $T_E$/EM: CCR7−/CD45RA−/CD57−; $T_{E/Exh}$: CCR7−/CD45RA−/CD57+; $T_{EMRA}$: CCR7−/CD45RA+; $T_{cm}$: CCR7+/CD45RA−; $T_{naive}$: CCR7+/CD45RA+. Values shown are the means of three technical replicates with error bars indicating ±1 standard deviation. The results shown are representative of four independent experiments using cells from three different healthy blood donors.

To test whether expression an anti-IL-6Rα scFv alters the T-cell subtype differentiation upon antigen stimulation, the T cells in the experiment described in the preceding paragraph were surface-stained with antibody for CCR7, CD45RA, and CD57 to determine the T-cell subtype. Subtype $T_{E/EM}$: CCR7–/CD45RA–/CD57–; subtype $T_{E/EX}$h: CCR7–/CD45RA–/CD57$^+$; subtype $T_{EMRA}$: CCR7–/CD45RA+; subtype $T_{cm}$: CCR7$^+$/CD45RA–; subtype $T_{naive}$: CCR7$^+$/CD45RA+. Values shown in FIGS. 5 and 7 are the means of three technical replicates with error bars indicating ±1 standard deviation. The results shown in FIG. 5 are representative of four independent experiments using cells from two different healthy blood donors, and the results in FIG. 7 are representative of four independent experiments using cells from three different healthy blood donors. As can be seen from FIGS. 5 and 7, there were very few $T_{EMRA}$ or $T_{naive}$ cells in any of the samples. The results in FIGS. 5-7 show that constitutive expression of anti-IL-6Rα scFv does not alter T cell subtype differentiation upon antigen stimulation, further confirming that the efficacy of adoptive T cell therapy would not be diminished by using T cells that express an anti-IL-6Rα scFv.

Figure 8:
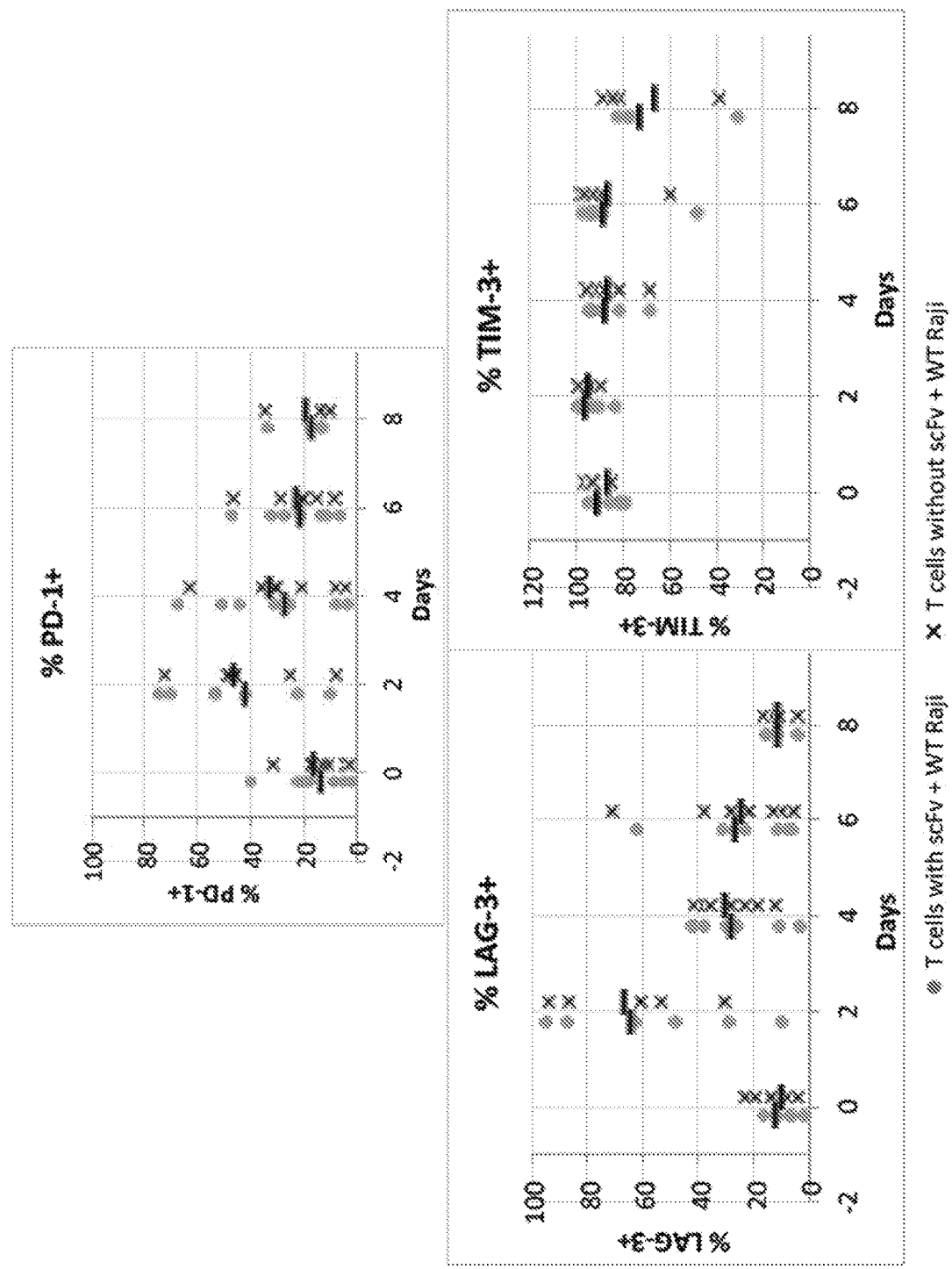
FIG. 8. Constitutive expression of anti-IL-6Rα scFv does not alter exhaustion marker expression in primary human T cells upon antigen stimulation. Primary human T cells constitutively expressing the anti-CD19 CAR with or without anti-IL-6Rα scFv were co-incubated with WT Raji cells at a 2:1 E:T ratio. PD-1, TIM-3, and LAG-3 expression levels were quantified by surface antibody staining and flow cytometry every two days. Three trials were performed with CD8+ T cells and four trials were performed with CD4+ T cells for a total of seven independent experiments. Each trial included three technical replicates per condition. Each data point in the plots represents the mean value of triplicates from one trial. The average value of seven trials for each time point is indicated by the black horizontal bar.

T cell exhaustion is a state of T cell dysfunction characterized by poor effector function, expression of inhibitory receptors, and a distinct transcriptional state. Exhaustion can limit the efficacy of T cells used in adoptive T cell therapy. Markers of exhaustion include PD-1, TIM-3, and LAG-3. To determine whether expression of an anti-IL-6Rα scFv would affect T cell exhaustion, primary human T cells constitutively expressing the anti-CD19 CAR with or without anti-IL-6Rα scFv were co-incubated with WT Raji cells at a 2:1 E:T ratio. PD-1, TIM-3, and LAG-3 expression levels were quantified by surface antibody staining and flow cytometry every two days. Three trials were performed with CD8$^+$ T cells and four trials were performed with CD4$^+$ T cells for a total of seven independent experiments. Each trial included three technical replicates per condition. Each data point in the plots in FIG. 8 represents the mean value of triplicates from one trial. The average value of seven trials for each time point is indicated by the black horizontal bars in FIG. 8. The results in FIG. 8 show that constitutive expression of anti-IL-6Rα scFv does not alter exhaustion marker expression in primary human T cells upon antigen stimulation, further confirming that expression of an anti-IL-6Rα scFv would not diminish the efficacy of adoptive T cell therapy.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All references, cited literature articles, patent publications, and sequences associated with any recited GenBank accession numbers are specifically incorporated herein by reference in their entirety for all purposes.

REFERENCES

The following references, to the extent that they provide exemplary procedural or other details supplementary to those set forth herein, are specifically incorporated herein by reference.

U.S. Pat. No. 4,684,611
U.S. Pat. No. 4,879,236

U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,543,293
U.S. Pat. No. 5,550,318
U.S. Pat. No. 5,563,055
U.S. Pat. No. 5,580,737
U.S. Pat. No. 5,580,859
U.S. Pat. No. 5,589,466
U.S. Pat. No. 5,591,616
U.S. Pat. No. 5,610,042
U.S. Pat. No. 5,631,146
U.S. Pat. No. 5,656,610
U.S. Pat. No. 5,670,373
U.S. Pat. No. 5,677,425
U.S. Pat. No. 5,702,932
U.S. Pat. No. 5,714,350
U.S. Pat. No. 5,736,524
U.S. Pat. No. 5,780,448
U.S. Pat. No. 5,786,462
U.S. Pat. No. 5,789,215
U.S. Pat. No. 5,871,986
U.S. Pat. No. 5,945,100
U.S. Pat. No. 5,981,274
U.S. Pat. No. 5,994,624
U.S. Pat. No. 6,350,861
U.S. Pat. No. 7,479,543
U.S. Pat. No. 8,580,264
U.S. Patent Pubin 2005/0106660
U.S. Patent Pubin 2006/0058510
U.S. Patent Pubin 2006/0088908
U.S. Patent Pubin 2010/0285564
Ahmad (2012) Clinical and Developmental Immunology Article ID 980250
Burton (1985) *Molec. Immunol.*, 22: 161-206
Carbonelli et al., *FEMS Microbiol. Lett.*, 177(1):75-82, 1999.
Chandler et al., *Proc. Natl. Acad. Sci. USA*, 94(8):3596-601, 1997.
Chen and Okayama, *Mol. Cell Biol.*, 7(8):2745-2752, 1987.
Cocea, *Biotechniques*, 23(5):814-816, 1997.
Cumber et al., *J. Immunology*, 149B:120-126, 1992.
European Patent 0 154 316
European Patent 0 322 094
European Patent 0 401 384
European Patent 0 486 525
Fechheimer, et al., *Proc Natl. Acad. Sci. USA*, 84:8463-8467, 1987.
Fraley et al., *Proc. Natl. Acad. Sci. USA*, 76:3348-3352, 1979.
Gopal, *Mol. Cell Biol.*, 5:1188-1190, 1985.
Graham and Van Der Eb, *Virology*, 52:456-467, 1973.
Harland and Weintraub, *J. Cell Biol.*, 101(3):1094-1099, 1985.
Harlow et al., Antibodies: A Laboratory Manual, Cold Spring Harbor Laboratory, Cold Spring Harbor, N.Y., Chapter 8, 1988.Ausubel et al., 1996
Huck et al. (1986) *Nucl. Acids Res.*
Kaeppler et al., *Plant Cell Rep.*, 8:415-418, 1990.
Kaneda et al., *Science*, 243:375-378, 1989.
Kato et al, *J. Biol. Chem.*, 266:3361-3364, 1991.
Kohl et al., *Proc. Natl. Acad. Sci., USA*, 100(4):1700-1705, 2003.
Koyama 1994 *Chem. Abstr.* 120: 217262t
Levenson et al., *Hum. Gene Ther.*, 9(8):1233-1236, 1998.
Liu et al. *Cell Mol. Biol.*, 49(2):209-216, 2003.
Meares et al., 1984 *Anal. Biochem.* 142: 68-78
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-28, 1993.
Pack et al., *Biochem.*, 31:1579-1584, 1992.
PCT Appln WO 94/09699
PCT Appln WO 95/06128;
PCT Publn. WO 1992019759
PCT Publn. WO 2006/056464
Potrykus et al., *Mol. Gen. Genet.*, 199(2):169-177, 1985.
Quadri et al. 1993 *Nucl. Med. Biol.* 20: 559-570
Rippe, et al., *Mol. Cell Biol.*, 10:689-695, 1990.
Rodwell et al. 1986 *PNAS* USA 83: 2632-2636;
Sambrook et al., In: *Molecular cloning*, Cold Spring Harbor Laboratory Press, Cold Spring Harbor, N.Y., 2001.Skerra, *J. Mol. Recogn.*, 13:167-187, 2000.
Skerra, *J. Biotechnol.*, 74(4):257-75, 2001.
Tan et al. (1990) *Proc. Natl. Acad. Sci. USA* 87: 162;
Wong et al., *Gene*, 10:87-94, 1980.

The invention claimed is:

1. A method for reducing the risk of cytokine release syndrome in a patient receiving an immunotherapy, the method comprising administering to the patient T cells comprising a heterologous nucleic acid molecule encoding an anti-IL-6Rα single chain antibody variable fragment (scFv) comprising a heavy chain variable region comprising CDR1 (SEQ ID NO:5), CDR2 (SEQ ID NO:6), and CDR3 (SEQ ID NO:7) attached by a heterologous linker to a light chain variable region comprising CDR4 (SEQ ID NO:8), CDR5 (SEQ ID NO:9), and CDR6 (SEQ ID NO:10), wherein the heterologous nucleic acid is expressed in the T cells.

2. The method of claim 1, wherein the T cells further express a chimeric antigen receptor.

3. The method of claim 2, wherein the patient has cancer.

4. The method of claim 2, wherein the patient has or will receive adoptive T-cell therapy.

5. The method of claim 2, wherein the patient has or will receive lymphodepletion.

6. The method of claim 1, wherein the T cells are autologous.

7. The method of claim 2, further comprising administering to the patient an antihistamine, a corticosteroid, a steroid, acetaminophen, furosemide, and/or intravenous fluids.

8. The method of claim 1, wherein the patient has one or more symptoms of cytokine release syndrome.

9. The method of claim 1, wherein the heavy chain variable region is on the N-terminal side of the light chain variable region.

10. The method of claim 1, wherein the light chain variable region is on the N-terminal side of the heavy chain variable region.

11. The method of claim 1, wherein the linker comprises the amino acid sequence GSTSGSGKPGSGEGSTKG (SEQ ID NO:11).

12. The method of claim 1, wherein the heterologous nucleic acid molecule is encoded on an expression construct.

13. The method of claim 12, wherein the expression construct comprises a cytokine-responsive promoter or promoter that increases expression when T cells are activated.

14. The method of claim 13, wherein the promoter responds positively to one or more of the following: NFAT-1, NF-κB, IL-6, TNF-α, IFN-γ, IL-1β, IL-2, IL-8, and IL-10.

15. The method of claim 1, wherein the heterologous nucleic acid further encodes for a signal peptide.

16. The method of claim 1, wherein the expression construct further comprises a constitutive promoter that controls the expression of the anti-IL-6RαscFv.

17. The method of claim 1, wherein the patient has an autoimmune disease.

18. The method of claim 12, wherein the expression construct is further defined as a viral vector.

19. The method of claim 12, wherein the expression construct is further defined as a plasmid.

* * * * *